United States Patent
Hanson et al.

(10) Patent No.: US 10,385,093 B2
(45) Date of Patent: Aug. 20, 2019

(54) ESTROGEN RECEPTOR IMAGING AGENTS

(71) Applicant: Northeastern University, Boston, MA (US)

(72) Inventors: Robert N. Hanson, Newton, MA (US); Kinh-Luan Dao, Randolph, MA (US)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 14/649,702

(22) PCT Filed: Dec. 10, 2013

(86) PCT No.: PCT/US2013/074183
§ 371 (c)(1),
(2) Date: Jun. 4, 2015

(87) PCT Pub. No.: WO2014/093378
PCT Pub. Date: Jun. 19, 2014

(65) Prior Publication Data
US 2015/0344518 A1 Dec. 3, 2015

Related U.S. Application Data

(60) Provisional application No. 61/735,184, filed on Dec. 10, 2012.

(51) Int. Cl.
C07J 43/00 (2006.01)
C07J 41/00 (2006.01)
C07J 21/00 (2006.01)
C07J 1/00 (2006.01)
C07J 71/00 (2006.01)

(52) U.S. Cl.
CPC ............ *C07J 41/0072* (2013.01); *C07J 41/00* (2013.01); *C07J 43/003* (2013.01); *C07B 2200/05* (2013.01); *C07J 1/0059* (2013.01); *C07J 21/006* (2013.01); *C07J 71/0015* (2013.01)

(58) Field of Classification Search
CPC ........ C07J 1/0059; C07J 21/006; C07J 41/00; C07J 41/0072; C07J 43/003; C07B 2200/05
USPC .......... 540/108; 552/626; 424/1.45, 9.1, 9.4; 514/176, 182
See application file for complete search history.

(56) References Cited

U.S. PATENT DOCUMENTS

2004/0171595 A1 9/2004 Benedetti et al.
2004/0229853 A1 11/2004 Prat et al.

FOREIGN PATENT DOCUMENTS

WO 2010/085747 A1 7/2010

OTHER PUBLICATIONS

Bennink, R. J., et al., "Estrogen receptor status in primary breast cancer: Iodine 123-labeled cis-11β-Methoxy-17α-iodovinyl Estradiol Scintigraphy", Radiology (2001), vol. 220, No. 3., pp. 774-779.
Cummins, C. H., "Radiolabeled steroidal estrogens in cancer research", Steroids (1993), vol. 58, pp. 245-259.
Dao, K.-L., et al., "Design, Synthesis, and Initial Biological Evaluation of a Steroidal Anti-Estrogen-Doxorubicin Bioconjugate for Targeting Estrogen Receptor-Positive Breast Cancer Cells", Bioconjugate Chemistry (2012), vol. 23, pp. 785-795.
De Vries, E. F. J., et al., "Nuclear Imaging of Hormonal Receptor Status in Breast Cancer: A Tool for Guiding Endocrine Treatment and Drug Development", Current Cancer Drug Targets (2007), vol. 7, pp. 510-519.
Gemignani, M.L, et al., "Feasibility and Predictability of Perioperative PET and Estrogen Receptor Ligand in Patients with Invasive Breast Cancer", J. Nucl. Med. (2013), vol. 54, No. 10, pp. 1697-1702.
Hanson, R.N., et al., "Convergent synthesis of a steroidal antiestrogen-mitomycin C hybrid using "click" chemistry", Org. Biomol. Chem. (2012), vol. 10, 2012, pp. 8501-8508.
Hanson, R. N., "Synthesis and evaluation of 11β-(4-Substituted phenyl) estradiol analogs: Transition from estrogen receptor agonists to antagonists", Bioorg. Met Chem. (2012), vol. 20, No. 12, pp. 3768-3780.
Hendricks, J.A., et al., "Synthesis of a spin-labeled anti-estrogen as a dynamic motion probe for the estrogen receptor ligand binding domain", Bioorganic & Medicinal Chemistry Letters (2012), vol. 22, pp. 1743-1746.
Jonson, S.D., et al., "Comparative Breast Tumor Imaging and Comparative in Vitro Metabolism of 16α-[18F]-Fluoroestradiol and 16β-[18F]Fluoromoxestrol in Isolated Hepatocytes", Nuclear Medicine and Biology (1999), vol. 26, pp. 123-130.
Kiesewetter, D.O., et al., "Synthesis of 16-Fluoroestrogens by Unusually Facile Fluoride Ion Displacement Reactions: Prospects for the Preparation of Fluorine-18 Labeled Estrogens", J. Org. Chem. (1984), vol. 49, pp. 4900-4905.
Kiesewetter, D.O., et al., "Preparation of Four Fluorine-18-Labeled Estrogens and Their Selective Uptakes in Target Tissues of Immature Rats", J. Nucl. Med. (1984), vol. 25, pp. 1212-1221.
Knott, K. E., et al., "Simplified and automatic one-pot synthesis of 16α-[18F]fluoroestradiol without high-performance liquid chromatography purification", Journal of Labelled Compounds and Radiopharmaceuticals (2011), vol. 54, pp. 149-753.
Kurland, B. F., et al., "Between-Patient and Within-Patient (Site-to-Site) Variability in Estrogen Receptor Binding, Measured in Vivo by 18F-Fluoroestradiol PET", J. Nucl. Med. (2011), vol. 52, No. 10, pp. 1541-1549.
Lim, J. L., "The Use of 3-Methoxymethyl-16β,17β-Epiestriol-O-Cyclic Sulfone as the Precursor in the Synthesis of F-18 16α-Fluoroestradiol", Nuclear Medicine and Biology (1996), vol. 23, No. 7, pp. 911-915.
Mathias, C.J., et al., "Characterization of the Uptake of 16 α-([18F]fluoro)-17β-Estradiol in DMBA-induced Mammary Tumors", Int. J. Rad. Appl. Instrum. (1987), vol. 14, No. 1, pp. 15-25.

(Continued)

Primary Examiner — Barbara P Badio
(74) Attorney, Agent, or Firm — Arent Fox LLP

(57) ABSTRACT

Compounds useful for molecular imaging of cells expressing estrogen receptors are provided. Also provided are intermediates for making the compounds and methods of making the compounds using a modular convergent strategy. Further, methods of making the intermediates are described, as well as methods of diagnosing disease in a subject by using the compounds as imaging agents.

12 Claims, 42 Drawing Sheets

(56) References Cited

OTHER PUBLICATIONS

Oh, S.J., et al., "The automatic production of 16α-[18F]fluoroestradiol using a conventional [18F]FDG module with a disposable cassette system", Applied Radiation and Isotopes (2007), vol. 65, pp. 676-681.

Pavlik, E. J., et al., "Characterization of High Specific Activity [16α-123I]Iodo-17β-estradiol as an Estrogen Receptor-specific Radioligand Capable of Imaging Estrogen Receptor-positive Tumors", Cancer Research (1990), vol. 50, pp. 7799-7805.

Pomper, M.G., et al., "11β-Methoxy-, 11β-Ethyl, and 17α-Ethynyl-Substituted 16α-Fluoroestradiols: Receptor-Based Imaging Agents with Enhanced Uptake Efficiency and Selectivity", J. Med. Chem. (1990), vol. 33, pp 3143-3155.

Ribeiro-Barras, et al. "Estrogen Receptor Imaging with 17α-[123I]Iodovinyl-11β-methoxyestradiol (MIVE2)—Part II. Preliminary Results in Patients with Breast Carcinoma", Int. J. Rad. Appl. Instrum. Part B (1992), vol. 19, No. 3, pp. 263-267.

Rijks, L.J., et al., "The Z-isomer of 11β-methoxy-17α-[123I]iodovinylestradiol is a Promising Radioligand for Estrogen Receptor Imaging in Human Breast Cancer", Nuclear Medicine and Biology (1997), vol. 24, 65-75.

Romer J. et al., "Automated Production of 16α-[18F]Fluoroestradiol for Breast Cancer Imaging", Nuclear Medicine & Biology (1999), vol. 26, pp. 473-479.

Seimbille, Y., et al., 18F-labeled difluoroestradiols: preparation and preclinical evaluation as estrogen receptor-binding radiopharmaceuticals, Steroids (2002), vol. 67, pp. 765-775.

VanBrocklin, H.F., et al., "16β-([18F]Fluoro) Estrogens: Systematic Investigation of a New Series of Fluorine-18-Labeled Estrogens as Potential Imaging Agents for Estrogen-Receptor-Positive Breast Tumors", J. Med. Chem. (1993), vol. 36, pp. 1619-1629.

VanBrocklin, H. F., et al., "The synthesis of 7α-methyl-substituted estrogens labeled with fluorine-18: potential breast tumor imaging agents", Steroids (1994), vol. 59, pp. 34-45.

16α[¹⁸F]-ES; (ref) Katzanellabogen et al

4-Me[¹⁸F]-ES; (ref) van Lier et al

17αethynyl-16α[¹⁸F]-ES; (ref) VanBrocklin et al

16β[¹⁸F]-ES; (ref) Welch et al

7α substituted[¹⁸F]-ES; (ref) van Lier et al

11β methoxy-16α[¹⁸F]-ES; (ref) Pomper et al

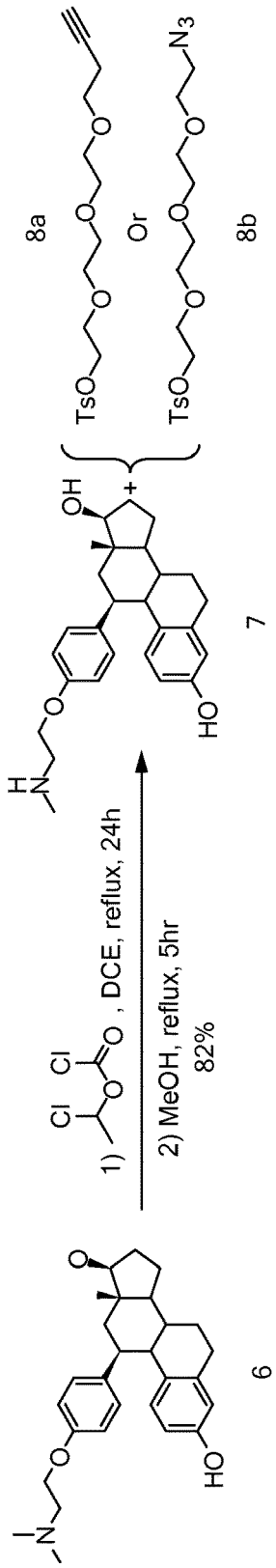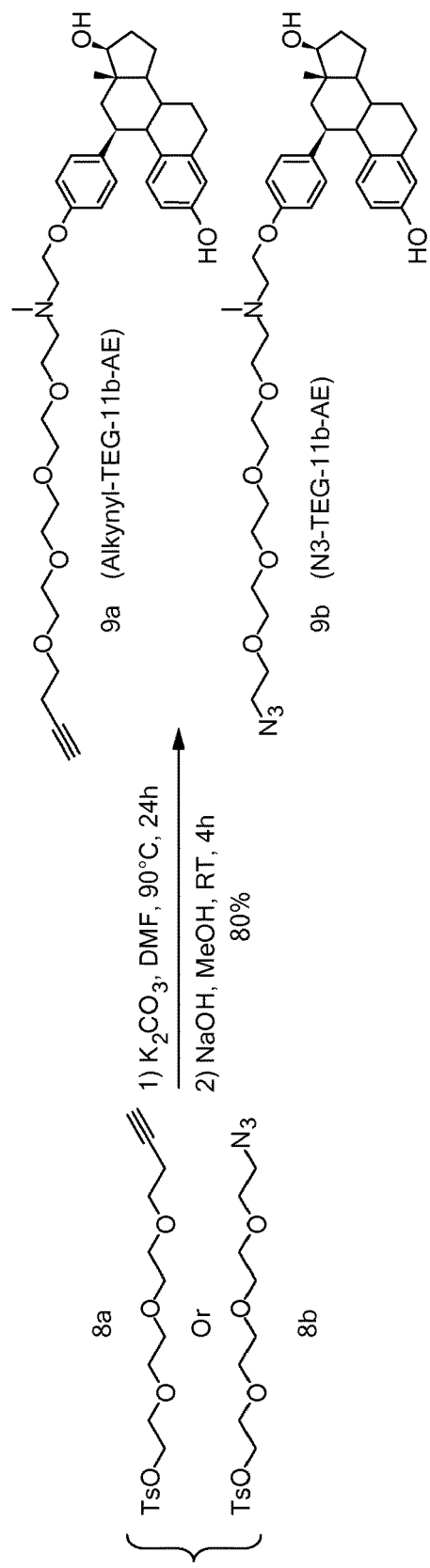
FIG. 2C
FIG. 2D

| Condition | Cu$^{+2}$ 80mM | ASC 200mM | BPDS 80mM | Cu$^+$ 80mM | 11βAE 1mM | $^{18}$FN3 | DMSO/H$_2$O | Temp °C | Time min | Rxn vol (μl) | Yield % |
|---|---|---|---|---|---|---|---|---|---|---|---|
| 1 | 10 | 30 | 20 |  | 20 | 5 | 100 | 60 | 5 | 185 | 0 |
| 2 |  |  | 20 | 20 | 20 | 10 | 50 | 60 | 5 | 120 | 30 |
| 3 |  |  | 20 | 20 |  | 10 | 50 | 60 | 5 | 120 | 30 |
| 4 |  |  | 40 | 40 | 40 | 10 |  | 60 | 5 | 130 | 95 |
| 5 |  |  |  | 40 | 40 | 10 | DMF (μL) 40 | 60 | 5 | 130 | 80 |
| 6 |  |  |  | 60 | 40 | 10 | 20 | 60 | 5 | 130 | 36 |
| 7 |  |  |  | 60 | 40 | 10 | 20 | 60 | 10 | 130 | 94 |
| 8 |  |  | 40 | 40 | 40 | 100 9.73mCi |  | 60 | 5 | 220 | 95 |

| | Cu+2 (80mM) in H2O | ASC (200mM) in H2O | BPDS (80 mM) in H2O | Cu+ (80mM) in MeCN | Alkyne (1 mM) | 18F-PEG3N3 in DMF/H2O | mCi | Additional Solvent | Temp °C MW, 30 W | Time min | Rxn Vol | Yield % |
|---|---|---|---|---|---|---|---|---|---|---|---|---|
| 1 | 10 | 30 | 20 | - | 20 | 5 | 0.3 | 100 | 60 | 5 | 185 | 0 |
| 2 | - | - | 20 | 20 | 20 | 10 | 0.5 | 50 | 60 | 5 | 120 | 30 |
| 3 | - | - | 40 | 40 | 20 | 10 | 0.3 | 10 | 60 | 5 | 120 | 52 |
| 4 | - | - | 40 | 40 | 40 | 10 | 0.3 | - | 60 | 5 | 130 | 95 |
| 5 | - | - | 20 | 20 | - | 10 | 0.4 | 70 | 60 | 5 | 120 | - |
| 6 | - | - | - | 40 | 40 | 10 | 0.6 | 40 | 60 | 5 | 130 | 80 |
| 7 | - | - | 20 | 40 | 40 | 80 | 1.9 | 20 | 60 | 5 | 200 | 36 |
| 8 | - | - | - | 40 | 40 | 5 | 0.6 | 40 | 60 | 5 | 125 | 85 |
| 9 | - | - | - | 40 | 40 | 50 | 5.1 | - | 60 | 5 | 130 | 31 |
| 10 | - | - | - | 40 | 40 | 50 | 3.8 | - | 60 | 10 | 130 | 67 |
| 11 | - | - | 20 | 40 | 40 | 40 | 7.1 | - | 60 | 10 | 130 | 65 |
| 12 | - | - | 40 | 40 | 40 | 40 | 6.0 | - | 60 | 5 | 140 | 78 |
| | - | - | - | - | - | - | - | - | - | - | 160 | 88 |

Cu+2 = CuSO4; Cu+1 = Cu(MeCN)4PF6; ASC = Sodium ascorbate; BPDS = Bathophenanthroline disulfonate, disodium salt

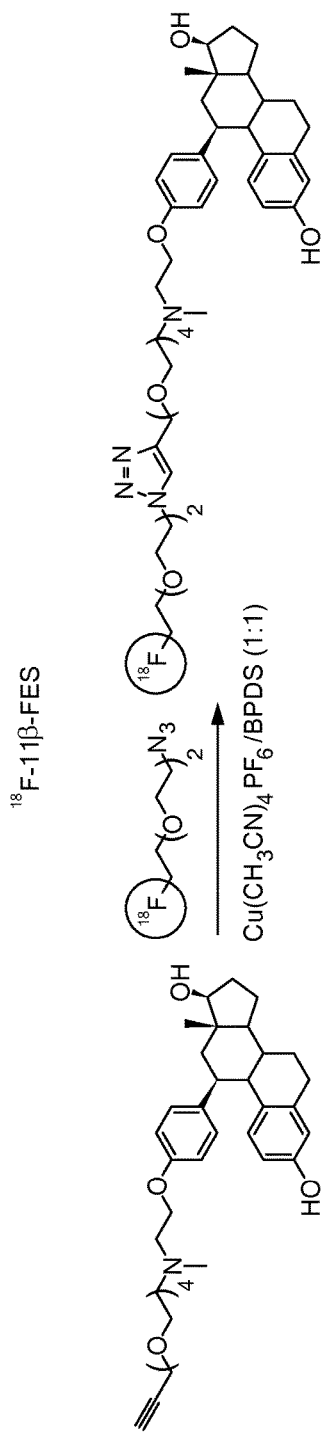
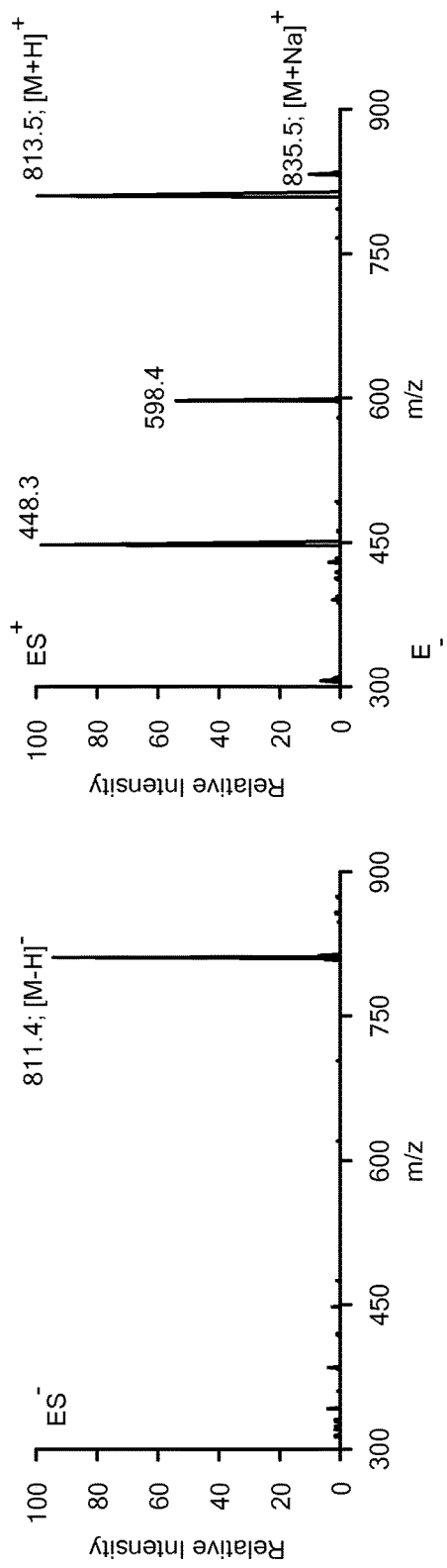
FIG. 27A
FIG. 27B

| | BPDS (80 mM) | Cu+ (80mM) | Alkyne (1 mM) | 18F-PEG3N3 | mCi | Temp °C | Time min | Rxn Vol | Yield % |
|---|---|---|---|---|---|---|---|---|---|
| | | | μL | | | | | | |
| 1 | 40 | 40 | 40 | 40 | 6.0 | 60 | 5 | 160 | 87.6 |
| 2 | 40 | 40 | 40 | 50 | 6.3 | 60 | 5 | 170 | 93.0 |
| 3 | 40 | 40 | 40 | 50 | 5.3 | 60 | 5 | 170 | 91.9 |
| 4 | 40 | 40 | 40 | 100 | 6.0 | 60 | 5 | 220 | 91.4 |
| 5 | 40 | 40 | 40 | 120 | 11.1 | 60 | 5 | 240 | 92.8 |
| 6 | 40 | 40 | 40 | 100 | 9.3 | 60 | 5 | 220 | 93.8 |
| 7 | 40 | 40 | 40 | 100 | 9.3 | 60 | 5 | 220 | 93.8 |
| 8 | 40 | 40 | 40 | 80 | 6.9 | 60 | 5 | 200 | 79.8 |
| 9 | 40 | 40 | 40 | 60 | 5.4 | 60 | 5 | 180 | 84.2 |

Average Conversion = 89.3 ± 5.0%, n = 9      7.6 ± 0.9 mCi isolated, 76% HPLC recovery, n = 2

$^{18}$F-11β-FES: Pharmacokinetics

| Co-solvent in Saline (0.9% NaCl) | Half-life (min) Slow | Half-life (min) Fast | Percent Fast (%) | Half-life Weighted (min) | Terminal % at 2 h |
|---|---|---|---|---|---|
| DMSO (5%) | 5.9 | 0.4 | 49.6 | 3.2 | 5.3 |
| 1:1 Solutol:DMA (4%) | 10.1 | 1.9 | 54.6 | 5.6 | 3.4 |
| Ethanol (8%) | 25.1 | 2.8 | 79.3 | 7.4 | 3.5 | n = 2 C57Bl/6 mice for each formulation; 36% reduction in terminal concentration using ethanol as co-solvent $^{18}$F-11β-FES: Biodistribution

| | Wild Type: C57BL/6 | | MCF7 Xenograft | |
|---|---|---|---|---|
| Organ | %ID/g Tissue | St Dev | %ID/g Tissue | St Dev |
| Feces | 5.549 | 4.492 | 4.303 | 0.324 |
| Uterus | 2.43 | 1.813 | 0.952 | 0.086 |
| Kidney | 1.807 | 0.590 | 2.229 | 0.115 |
| Liver | 1.669 | 0.097 | 0.924 | 0.045 |
| Blood | 1.280 | 0.050 | 1.313 | 0.489 |
| Bone | 1.136 | 0.118 | 1.710 | 0.317 |
| Pancreas | 0.977 | 0.284 | | |
| Int. (L) | 0.877 | 0.12 | | |
| Muscle | 0.810 | 0.092 | 0.509 | 0.035 |
| Int. (S) | 0.795 | 0.117 | | |
| Spleen | 0.764 | 0.138 | | |
| Skin | 0.658 | 0.344 | | |
| Stomach | 0.585 | 0.040 | | |
| Lung | 0.485 | 0.161 | 0.345 | 0.113 |
| Heart | 0.449 | 0.027 | 0.395 | 0.031 |
| Fat | 0.178 | 0.018 | 0.243 | 0.083 |
| Tumor | | | 1.036 | 0.426 |

*FIG. 30C*

ESTROGEN RECEPTOR IMAGING AGENTS

CROSS-REFERENCE TO RELATED APPLICATIONS

This application claims the priority of U.S. Provisional Application No. 61/735,184 filed Dec. 10, 2012 and entitled "RADIONUCLIDIC AND NONRADIONUCLIDIC MOLECULAR IMAGING AGENTS FOR THE ESTROGEN RECEPTOR BASED ON 11-BETA SUBSTITUTED STEROIDAL ANTIESTROGENS", which is hereby incorporated by reference in its entirety.

BACKGROUND

Molecular imaging (MI) enables integration of patient and disease-related information with anatomical imaging (Hanson, R. N., 2012). With MI one can visualize, characterize, and measure biological processes at the molecular level in a living organism (Kodibagkar, V. D et al., 2012; Koolen, B. B. et al., 2012; Misri, R. et al., 2012). Further, use of MI in the diagnosis of a disease results in improved clinical risk assessment, optimization of treatment and therapy, better patient outcome, and helps inter- and intra-subject comparisons. (Moss, J. A. et al., 2012; Vavere, A. L. et al., 2012; James, M. L. et al., 2012).

In medicine MI has evolved into two distinctive areas: anatomy-based or structural imaging, and nuclear medicine (Beyer, T. et al., 2009; Antoch, G., et al., 2009; Mawlawi, O. et al., 2009). Traditional imaging such as computed tomography (CT) and magnetic resonance imaging (MRI) are now primarily used for extracting anatomical and/or structural information. On the other hand nuclear medicine, using methods such as positron emission tomography (PET) and single photon emitted tomography (SPECT)), focusses on molecular events in living organisms, and thereby provides functional and/or physiological imaging. In oncology the information derived from PET and SPECT imaging is integrated with other patient specific disease information for diagnosis and treatment (Buck, A. K. et al., 2012; Morales-Avila, E. et al., 2011; Khalil, M. M. et al., 2011). Table 1 below summarizes the major differences among the various MI modalities.

X-ray computed tomography or computed tomography (CT scan) is a computer processed X-ray imaging technology that provides anatomical images of the body, which may be manipulated to obtain diagnostic information. CT inherently provides high-contrast and resolution, but exposes the patient to high radiation dose enhancing the risk of DNA or cellular damage. CT methods that provide high signal to noise ratio at lower radiation doses are currently being investigated (Buck, A. K. et al., 2012).

Optical imaging is another modality for molecular imaging, and is based on the detection of light photons and their interaction with the tissue. It has been used mostly in preclinical studies. Two major optical imaging methods are bioluminescence imaging (BLI) and fluorescence imaging (FI). BLI requires cellular expression of the enzyme luciferase, which is incorporated into the DNA of animals used for modeling of any given disease. BLI is most useful in vivo in small animal disease models, e.g., mouse models, since the depth sensitivity of the BLI is only 1-2 cm (Alhasan, M. K., et al. 2012). Fluorescent imaging (FI) is designed to look at the cell surface distribution of fluorescent signals. It is used in both live and fixed cells, and does not require any substrate. In this method fluorochromes are conjugated to peptides or antibodies, and binding of the conjugates to targets on the surface of cells provides information about target expression. Fluorescent imaging provides contrast sensitivity that is approximately comparable to radioactivity-based imaging. However, tissue penetration of FI signals is less than that of PET or SPECT. New methods of FI for improving relative sensitivity and resolution, preparation of newer imaging probes, and better signal-to-noise amplifiers are currently being developed (Kodibagkar, V. D. et al., 2012; Koolen, B. B. et al., 2012; Misri, R. et al., 2012).

Ultrasound imaging (UI) also a molecular imaging technique, and is currently being development as a nano-drug delivery system. UI is performed by utilizing microbubbles, liposomes, or perfluorocarbon emulsions as scaffolds functionalized with different targeting agents. UI offers high spatial resolution (<1 mm) and can provide detailed anatomical information for coregistration with other molecular imaging methods. Because of the relatively large size of

TABLE 1

Noninvasive in vivo molecular imaging modalities (Buck, A. K. et al., 2012)

| Imaging | Modality Energy used | Spatial Resolution (mm) Clinical | Spatial Resolution (mm) animal | Acquisition time/frame (s) | Probe mass (ng) | Sensitivity of detection (Mol/l) | Depth of penetration (mm) |
|---|---|---|---|---|---|---|---|
| PET | Annihilation | 3-8 | 1-3 | 1-300 | 1-100 | $10^{-11}$-$10^{-12}$ | >300 |
| SPECT | Y-photons | 5-12 | 1-4 | 60-2000 | 1-1000 | $10^{-10}$-$10^{-11}$ | >300 |
| CT | X-rays | 0.5-1 | 0.03-0.4 | 1-300 | — | — | >300 |
| MRI | Rf | 0.2-0.1 | 0.025-0.1 | 50-3000 | $10^3$-$10^6$ | $10^{-3}$-$10^{-5}$ | >300 |
| Ultrasound | High Rf | 0.1-1.0 | 0.05-0.1 | 0.1-100 | $10^3$-$10^6$ | — | 1-200 |
| BLI | IR | — | 3-10 | 10-300 | $10^3$-$10^6$ | $10^{-13}$-$10^{-16}$ | 1-10 |
| FLI | IR | — | 3-10 | 10-2000 | $10^3$-$10^6$ | $10^{-9}$-$10^{-11}$ | 1-20 |

Magnetic resonance imaging (MRI) primarily provides information about soft tissue. Although MRI provides high spatial resolution (<1 mm), and has the ability to visualize anatomical, physiological, and/or metabolic information in a single imaging session, it has low sensitivity for biological targets. Therefore, this method has not been tailored to visualize cancer or disease specific disorders (Misri, R. et al., 2012).

imaging reagents or particles (>250 nm) this technique has limited capacity for tissue penetration, and is used specifically for vascular imaging.

Molecular imaging of estrogen receptor expressing cells and tissues can provide the ability to detect tumors that overexpress the estrogen receptor (ER), having significant positive impact on diagnosis and therapy of ER-dependent cancer, such as breast cancer, in which over-expression of ER plays a major role (Dunn L. et al., 2009; Varghese C. et al., 2007; Schiff, R. et al., 2005). Among patients presenting with breast cancer, approximately 65-75% have primary tumors with elevated ER levels. Currently, receptor status of the tumor is determined via fine needle biopsy and, while minimally invasive, the technique requires removing tumor cells to be analyzed from the body (Higa, G. M. et al., 2009; Allred, D. C. et al., 2009). Because treatment protocols are dependent upon accurate characterization of the tissue sample, alternate methods that non-invasively characterize the entire body for potential distal metastases, and are quantitative, are of interest. MI agents that bind to specific biomarkers can provide important physiological and biochemical information regarding the disease leading to improved treatment plans and improved patient outcomes.

Several non-invasive modalities are currently used to image normal and cancerous breast tissue (Keune, J. D. et al., 2010; DeMartini, W. et al., 2008; van de Ven, S. M. W. Y. et al., 2008; Yu, E. Y. et al., 2007; Czernin, J. et al., 2010; Pantaleo, M. A. et al., 2008). Although many biomarkers associated with tumor sensitivity and invasiveness are being examined using experimental radiotracers, the expression of ER remains one of the most important diagnostic indicators for breast cancer (de Vries, E. F. J. et al., 2007; Schroeder, C. P. et al., 2007; Dittmann, H. et al., 2009). A radiotracer that binds with high affinity and selectivity to the estrogen receptor-alpha (ERα) would yield diagnostic data not provided by any other molecular agent or imaging modality as it would directly indicate the receptor status of suspected lesions. Whole body imaging would detect other ER-expressing tissues which may be secondary lesions. Imaging following chemotherapy (and/or surgery) would also demonstrate the presence or absence of recurrent ER-responsive disease, as well as the effectiveness of the intervention. Such information is crucial in providing individualized treatment.

Estradiol derivatives used for molecular imaging in clinical studies include radioiodinated molecules, e.g., isomers of 11β-methoxy-(17α,20E/Z)-[$^{123}$I]iodovinylestradiol. Among the isomers, the 20Z isomer yields better images of ER(+) human breast tumors than the 20E isomer. Although the diagnostic radioiodinated estradiols were selectively and sensitively detected in both primary and metastatic ER(+) breast cancer, extensive correlation between imaging and clinical outcome has not yet become available (Pysz, M. A. et al., 2010; Yager, J. D. et al., 2006; Benard, F. et al., 2005; Cummins, C. H., 1993).

Steroidal estrogen derivatives with the prosthetic $^{99m}$Tc chelates at different positions have been investigated also, although none have yet been clinically approved (Pavlik, E. J. et al., 1990).

Estradiol derivatives labeled with $^{18}$F have also been explored, and among the compounds evaluated (FIG. 1), 16α-[$^{18}$F]-estradiol ([$^{18}$F]-ES) is currently in clinical use. The 11β analog, 4-Fluoro-11β-methoxy-16α-[$^{18}$F]-flouroestradiol (4FMFES; FIG. 1) tracer also showed favorable biodistribution in small animal studies, and exhibited higher selectivity uptake ratios than that obtained by using [$^{18}$F]-ES. The compound 4FMFES is also being evaluated in studies for human biodistribution and dosimetry. Another compound, 7α-substituted [$^{18}$F]-ES, has also been prepared and evaluated as a possible tracer for ER(+) breast tumors. However, the biological data showed no significant improvement on target to non-target uptake ratios compared to other $^{18}$F-ES radiotracers (Cummins, C. H., 1993; Pavlik, E. J. et al., 1990; Ribeiro-Barras, M. J. et al., 1992; Rijks, L. J. M. et al., 1997; Bennink, R. J. et al., 2001).

Although [$^{18}$F]-16α-fluoroestradiol (FES) was developed in the 1980s, its use has been limited to fewer than a thousand patients (Kiesewetter, D. O. et al., 1984; Kiesewetter, D. O., Kilbourn, M. R. et al., 1984; Sundararajan, L. et al., 2007; Kurland, B. F. et al., 2011; Peterson, L. M. et al., 2011; Linden, H. M. et al., 2011; Dehdashti, F. et al., 2009; Gemignani, M. L., et al., 2013). FES is prepared from a simple precursor (2 mg/run) in an overall radiochemical yield of only approximately 30%. A careful chromatographic separation is required to remove several other radioactive by-products and non-radioactive materials. FES is typically obtained with a specific activity in the 200-1000 Ci/mmol range, appropriate for most clinical applications. This radiosynthetic procedure is not trivial, even with the use of automated methods (Lim, J. L. et al., 1996; Romer, J. et al., 1999; Oh, S. J. et al., 2007; Kumar, P. et al., 2007; Kumar, P. et al., 2012; Knott, K. E. et al., 2011). Biologically, FES is essentially a mimic for endogenous estradiol and undergoes comparable pharmacodynamic (PD) and pharmacokinetic (PK) processes (Mankoff, D A. et al., 1997; Jonson, S. D. et al., 1998; Bonasera, T. A. et al., 1997; Downer, J. B. et al., 2001; Benard, F. et al., 2001).

FES binds to steroid hormone binding globulin (SHBG) and as much as 45% of FES in circulating plasma is found complexed with SHBG. Therefore, although FES binds to ER in target tissues with a relative binding affinity (RBA) of 80%, it may largely not be accessible to target tissue, thereby impairing uptake of FES uptake in tumors. FES is rapidly cleared by the liver where it undergoes rapid and extensive metabolism such that less than 20% of radioactivity in plasma of patients is parent FES. The metabolites generated contribute to non-specific tissue distribution and accumulation in the liver and gut, and results in high background signal that compromises detection of lesions in adjacent tissues. Nevertheless, eleven completed or ongoing clinical studies are attempting to demonstrate the extent to which FES can contribute to the management of patients with breast cancer (see clinicaltrials.gov). A recent report shows that imaging with FES of patients with primary breast cancer in a preoperative setting can provide valuable information, but significant limitations still remain (Gemignani, M. L. et al., 2013). For example, the Gemignani, M. L. et al., report showed that although the standard uptake value of $^{18}$F-FES PET correlated with ER immunohistochemistry expression, it did not correlate with gene expression patients with early breast cancer.

Imaging of estrogen receptor (ER) in vivo using ER binding radiopharmaceuticals can be used for determining the ER expression status during tumor staging. Fluorine-18, Iodine-123 and other cyclotron-produced radionuclides have been used to label ER binding ligands to develop such in vivo radioimaging probes (Pomper, M. G. et L., 1990; Kiesewetter, D. O. et al., 1984; VanBrocklin, H. F. et al., 1993; VanBrocklin, H. F. et al., 1994; Landvatter, S. W. et al., 1983; French, A. N. et al., 1993; French, A. N., Wilson, S. R. et al., 1993; LaFrate, A. L. et al., 2009; Bergmann, K. E. et al., 1994; Hostetler, E. D. et al., 1999).

Some of these radioligands, for example 16α-$^{18}$F-17β-estradiol ($^{18}$F-FES), have been evaluated clinically for the imaging of hormone dependent breast tumor and predicting the responsiveness of the tumor to antiestrogen drugs (Seimbille, Y. et al., 2002; Mortimer, J. E. et al., 1996). So far, none of the established ligands has been approved for routine clinical use as a breast cancer diagnostic reagent. Estrogen imaging agents with the radionuclide $^{99m}$Tc for SPECT have also been reported (Bigott, H. M. et al., 2005; Luyt, L. G. et al., 2003; Skaddan, M. B.; Wust, F. R.; Jonson, S. et al., 2000). However, most of the reported compounds have displayed suboptimal target tissue selectivity, possibly due to their lipophilicity, or rapid metabolism. In addition, these radioligands were synthesized by inefficient linear approaches, leading to products that were difficult to purify, leading to suboptimal yield and purity (Huang, L. et al., 2010; Nayak, T. K. et al., 2008).

Because many of the radioligands that have been developed still exhibit low receptor (estrogen receptors ERα, ERβ) binding affinity and non-ER regulated uptake, there is a need to develop ER-targeted radioligands having high specific activity (radioactivity per unit mass of the radioligand >1 Ci/mmol, high specific receptor binding affinity, low non-specific binding), and appropriate metabolic and clearance characteristics, both to characterize the tumors and to predict or determine their response to anti-hormonal therapy.

SUMMARY OF THE INVENTION

Provided herein are compounds useful for molecular imaging of cells expressing estrogen receptor, intermediates for making the compounds, methods of making the compounds and intermediates, and methods of diagnosing, prognosing, or treating a disease in a subject by administering the compounds.

One aspect of the invention is a compound according to formula (I),

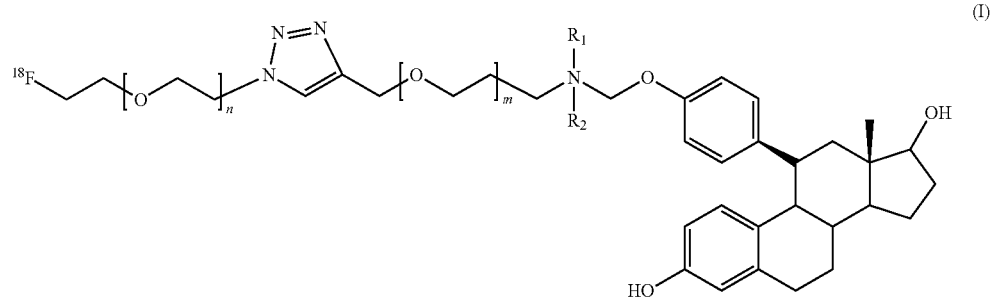

where n is a number in the range of 1-10; m is a number in the range of 4-10; $R^1$ is H or a $C_{1-3}$ alkyl group; and $R^2$ is either absent, or selected from a group consisting of H and a $C_{1-3}$ alkyl group. As used herein, a "number" in a chemical formula refers to a whole number, unless otherwise specified.

Another aspect of the invention is a compound according to formula (II),

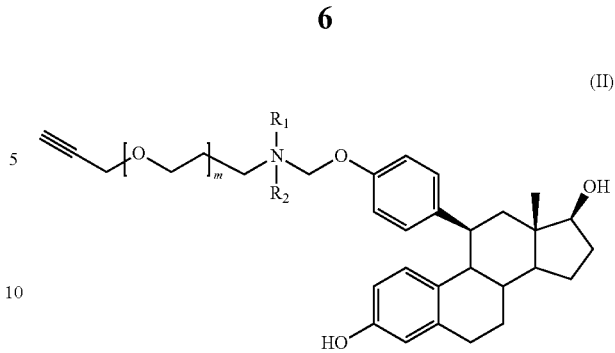

where m is a number in the range of 4-10; $R^1$ is H or a $C_{1-3}$ alkyl group; and $R^2$ is either absent, or selected from a group consisting of H and a $C_{1-3}$ alkyl group.

Another aspect of the invention is a compound according to formula (III),

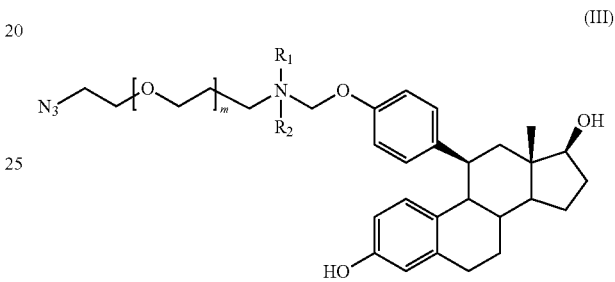

where m is a number in the range of 4-10; $R^1$ is H or a $C_{1-3}$ alkyl group; and $R^2$ is either absent, or selected from a group consisting of H and a $C_{1-3}$ alkyl group.

Another embodiment of the invention is a process for the preparation of a compound according to formula (I), including the step of reacting a compound according to formula (II) with a compound according to formula (IV) using a Huisgen [3+2] cycloaddition reaction,

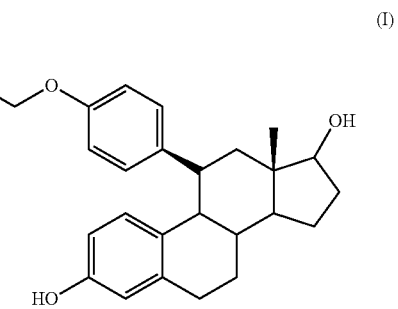

where x is a number in the range of 1-10.

Yet another embodiment of the invention is a compound according to formula (V)

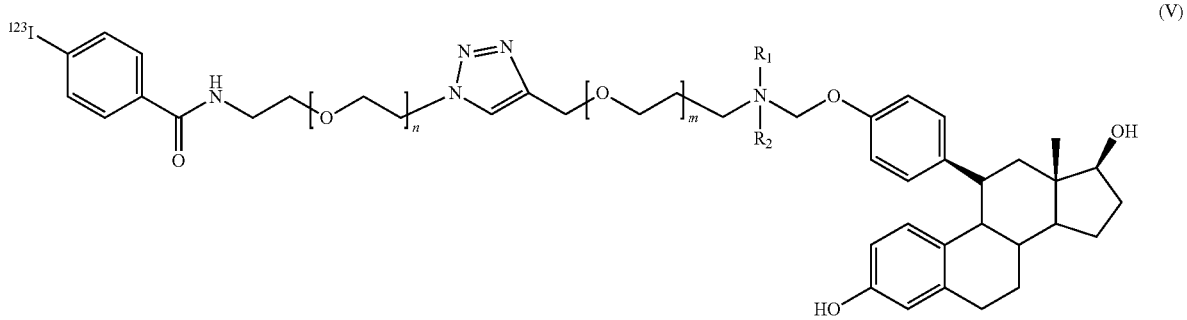
(V)

where n is a number in the range of 1-10; m is any number in the range of 4-10; $R^1$ is H or a $C_{1-3}$ alkyl group; and $R^2$ is either absent, or selected from a group consisting of H and a $C_{1-3}$ alkyl group.

A related embodiment of the invention is a process for the preparation of a compound according to formula (V) including the step of reacting a compound according to formula (II) with a compound according to formula (VI) using a Huisgen [3+2] cycloaddition reaction,

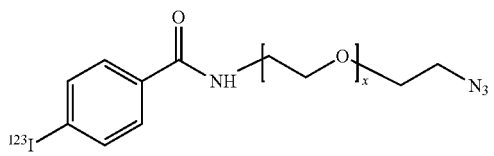
(VI)

where x is a number in the range of 1-10.

Another aspect the invention is a compound according to formula (VII),

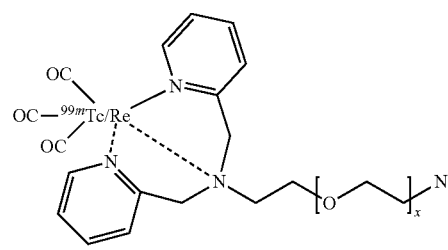
(VIII)

where x is a number in the range of 1-10.

Another aspect of the invention is a pharmaceutical composition containing any of the compounds described above and a pharmaceutically effective carrier or diluent.

Another aspect of the invention is a method of diagnosing a disease in a subject including detecting a cell expressing estrogen receptors by contacting any of the compounds having the formula (I), (V), or (VII) to the cell, and imaging the cell with positron emission tomography (PET) or single photon emission computed tomography (SPECT). In a related embodiment the cell contains or expresses an estrogen receptor. For example, the disease can be breast cancer or endometrial cancer. In a further related embodiment the subject has received anti-cancer treatment, and the method is used for determining the effectiveness of the treatment or the progress of the disease.

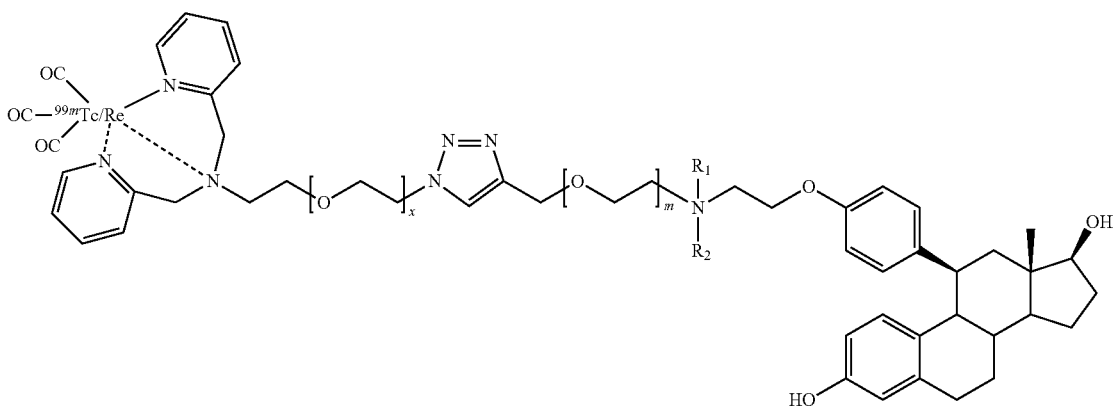
(VII)

where x is a number in the range of 1-10; m is a number in the range of 4-10; $R^1$ is H or a $C_{1-3}$ alkyl group; and $R^2$ is either absent, or selected from a group consisting of H and a $C_{1-3}$ alkyl group.

A related embodiment of the invention is a process for the preparation of a compound according to formula (VII) including the step of reacting a compound according to formula (II) with a compound according to formula (VIII) using a Huisgen [3+2] cycloaddition reaction, Another aspect of the invention is a compound according to formula (IX),

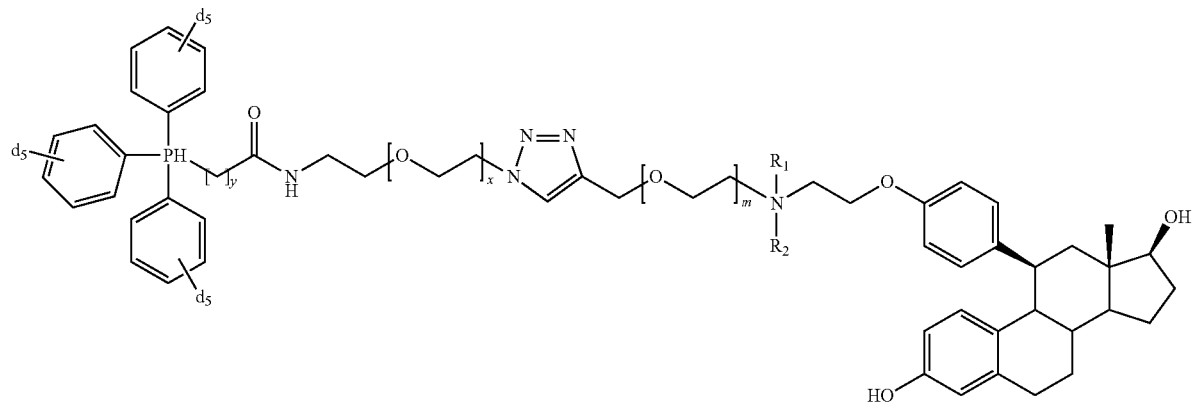

(IX)

where m is a number in the range of 4-10; each of x and y is independently a number in the range of 1-10; $R^1$ is H or a $C_{1-3}$ alkyl group; d is deuterium; and $R^2$ is either absent, or selected from a group consisting of H and a $C_{1-3}$ alkyl group.

A related aspect of the invention is a process for the preparation of a compound according to formula (IX) including the step of reacting a compound according to formula (II) with a compound according to formula (X),

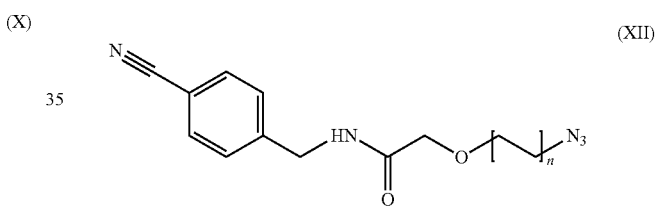

(X)

using a Huisgen [3+2] cycloaddition reaction, where each of x and y is independently a number in the range 1-10, and d is deuterium.

According to another aspect the invention is a compound according to formula (XI), where n is a number in the range of 1-10; m is a number in the range of 4-10; $R^1$ is H or a $C_{1-3}$ alkyl group; and $R^2$ is either absent or selected from the group consisting of H and a $C_{1-3}$ alkyl group.

A related aspect of the invention is a process for the preparation of a compound according to formula (XI) including the step of reacting a compound according to formula (III) with a compound according to formula (XII), n being a number in the range of 1-10, (XII)

using a Huisgen [3+2] cycloaddition reaction.

A related aspect of the invention is a pharmaceutical composition including any of the compounds (IX) or (XI) and a pharmaceutically effective carrier or diluent.

Another related aspect of the invention is a method of diagnosing a disease in a subject including detecting a cell by contacting any of the compounds (IX) or (XI), and imaging the cell in vitro with Raman spectroscopy. For example, the disease is breast cancer or endometrial cancer. In related embodiments the cell comprises an estrogen

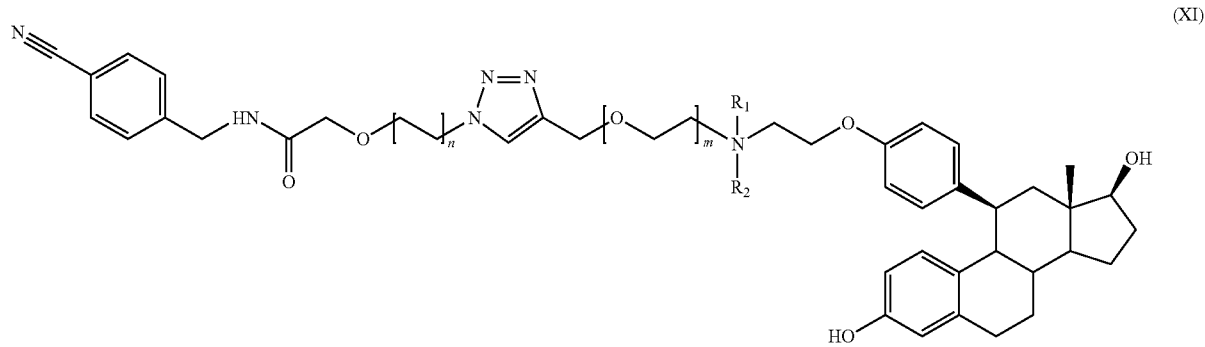

(XI)

receptor. For example, the subject has received anti-cancer treatment, and the method is used for determining effectiveness of the treatment.

A further embodiment of the invention is a compound according to the formula (XIV), (XIV)

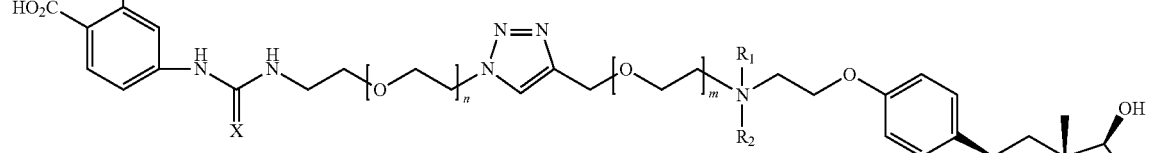

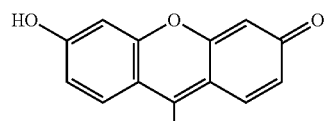
or similar fluorophore

X = O/S where n is a number in the range of 1-10; m is a number in the range of 4-10; X is O or S $R^1$ is H or a $C_{1-3}$ alkyl group; and $R^2$ is either absent or selected from a group consisting of H and a $C_{1-3}$ alkyl group.

An aspect of the invention is a process for the preparation of a compound according to formula (XIV) including the step of reacting a compound according to formula (II) with a compound according to formula (XV), (XV)

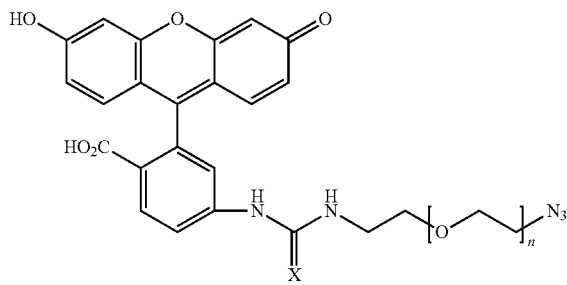

using the Huisgen [3+2] cycloaddition reaction, wherein $R^1$ is either absent, or selected from a group consisting of H and a $C_{1-3}$ alkyl group, X is O or S, and n is a number in the range of 1-10.

A related aspect of the invention is a method of diagnosing a disease in a subject including detecting a cell in vitro by contacting the compound (XIV) and imaging the cell with fluorescence spectroscopy. For example, the cell contains or expresses an estrogen receptor. For example, the disease can be breast cancer or endometrial cancer.

Another aspect of the invention is a process for the preparation of a compound according to formula (XVIII)

(XVIII)

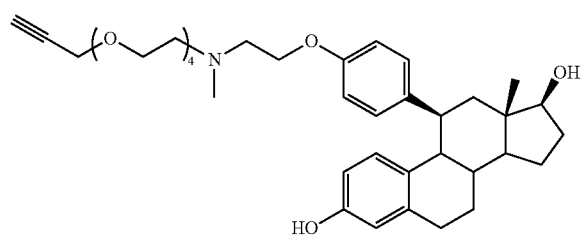

including the steps of transforming estra-5(10),9(11)-diene-3,17-dione 3-ethylenedioxy ketal (1) into 11β-(4-Hydroxyphenyl)-estra-4,9-diene-3,17-dione (3) by reacting (1) initially with a peroxide reagent to give an epoxide, and treating the product obtained with the Grignard reagent derived from trimethylsilyloxyphenyl bromide to obtain compound (3), alkylating (3) with dimethylaminoethyl chloride to obtain compound (4), aromatizing (4) with acetyl bromide and acetic anhydride to obtain compound (5), reducing and saponifying (5) to obtain compound (6), demethylating (6) with alpha chloroethyl chloroformate to obtain compound (7), and reacting (7) with reagent (8a),

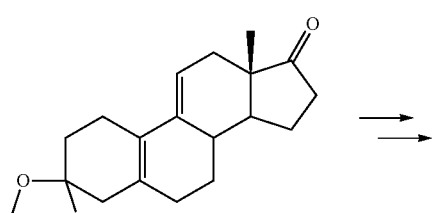

1

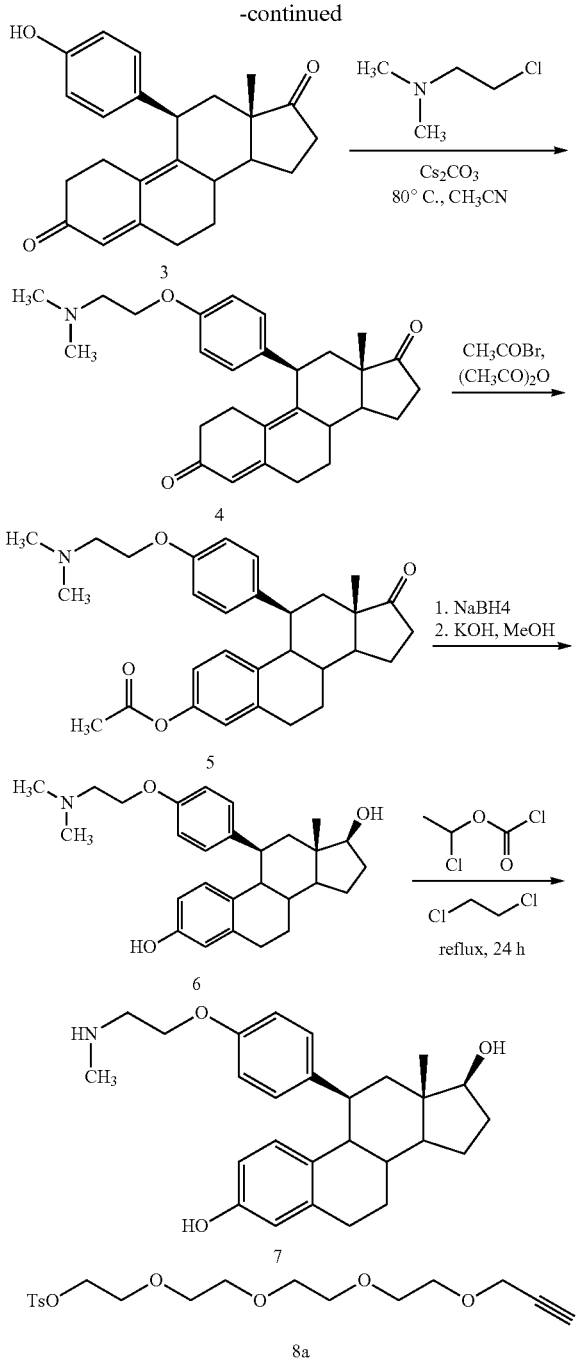

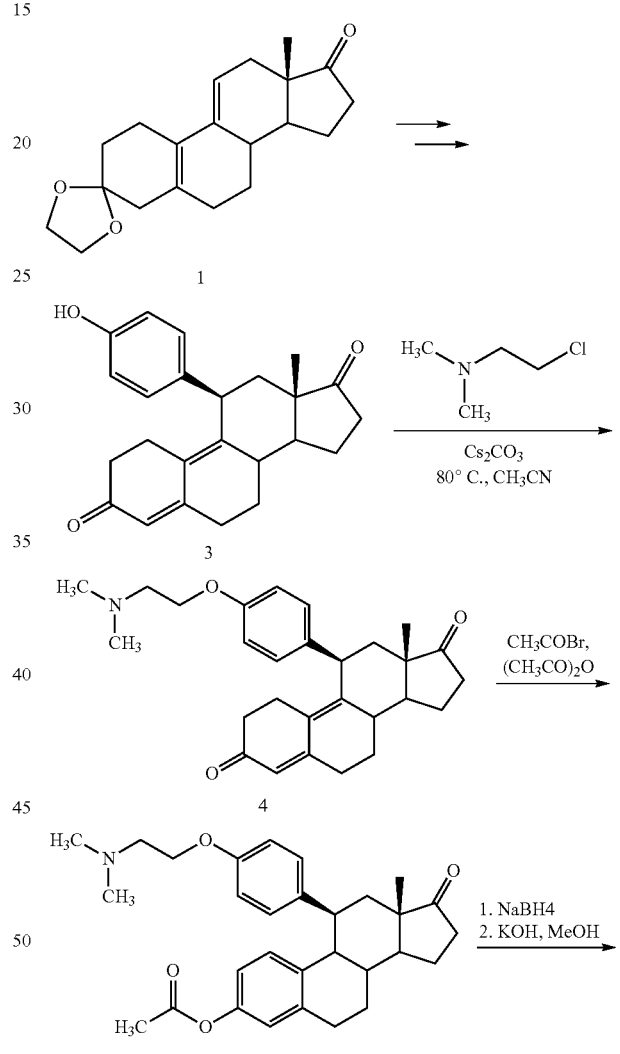

including the steps of transforming estra-5(10),9(11)-diene-3,17-dione 3-ethylenedioxy ketal (1) into 11β-(4-Hydroxyphenyl)-estra-4,9-diene-3,17-dione (3), by reacting (1) initially with a peroxide reagent to give an epoxide, and treating the product obtained with the Grignard reagent derived from trimethylsilyloxyphenyl bromide to obtain compound (3), alkylating (3) with dimethylaminoethyl chloride to obtain compound (4), aromatizing (4) with acetyl bromide and acetic anhydride to obtain compound (5), reducing and saponifying (5) to obtain compound (6), demethylating (6) with alpha chloroethyl chloroformate to obtain compound (7), and reacting (7) with reagent (8b)

thereby obtaining the compound according to formula (XVIII). See FIG. 2.

Yet another aspect of the invention is a process for the preparation of a compound according to formula (XIX),

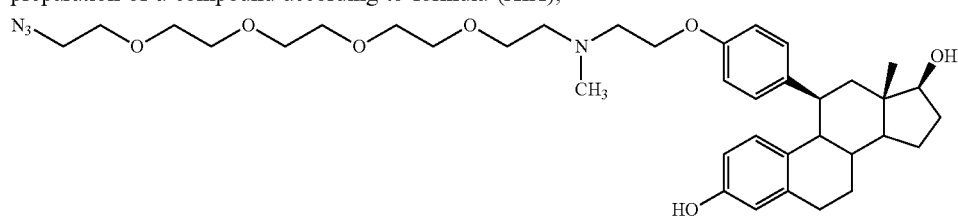

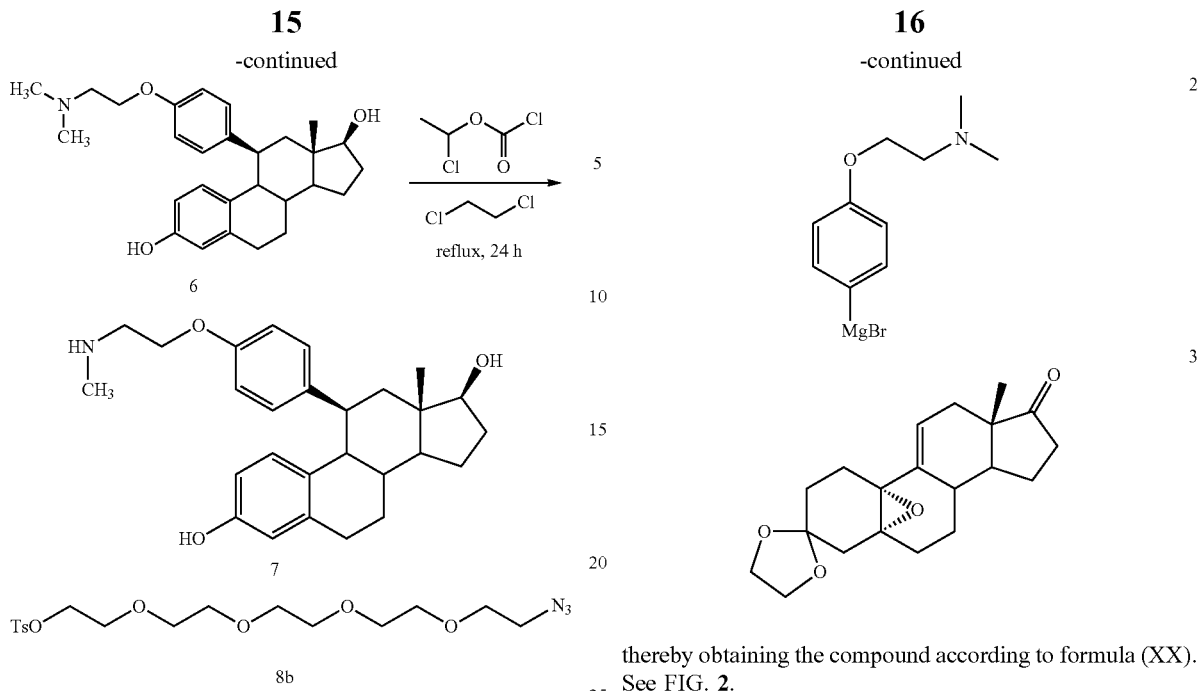

thereby obtaining the compound according to formula (XVIII). See FIG. 2.

Another aspect of the invention is a process for the preparation of a compound according to formula (XX)

including the steps of: preparing 2-(4-bromophenoxy)-N,N-dimethylethanamine (1) by reacting 4-bromophenol with 2-dimethylaminoethyl chloride, converting (1) to (4-(2-(dimethylamino)ethoxy)phenyl)magnesium bromide (2) by treating with reagents including Mg, and iodine, and reacting (2) with 3,3-Ethylenedioxy-5(10)-α-epoxy-estr-9-ene-17-one (3) in the presence of CuI and acetic acid thereby obtaining the compound according to formula (XX). See FIG. 2.

Yet another aspect of the invention is a kit for preparing a compound according to any of Formulas I, V, VI, VII, or VIII. The kit can include, for example a labeling moiety and instructions for reacting a compound according to any of Formulas II, III, or XI and the labeling moiety to provide a compound according to according to any of Formulas I, V, VI, VII, VIII, or IX. The labeling moiety can be, for example, a compound according to any of Formulas IV, VI, or VIII.

Still another aspect of the invention is the use of a compound according to any of Formulas I, V, VI, VII, VIII, or IX as an imaging agent for estrogen receptors in a cell, tissue, or a mammalian subject.

Another aspect of the invention is the use of a compound according to any of Formulas II, III, or XI to prepare an imaging agent for estrogen receptors.

BRIEF DESCRIPTION OF THE DRAWINGS

Figure 22:
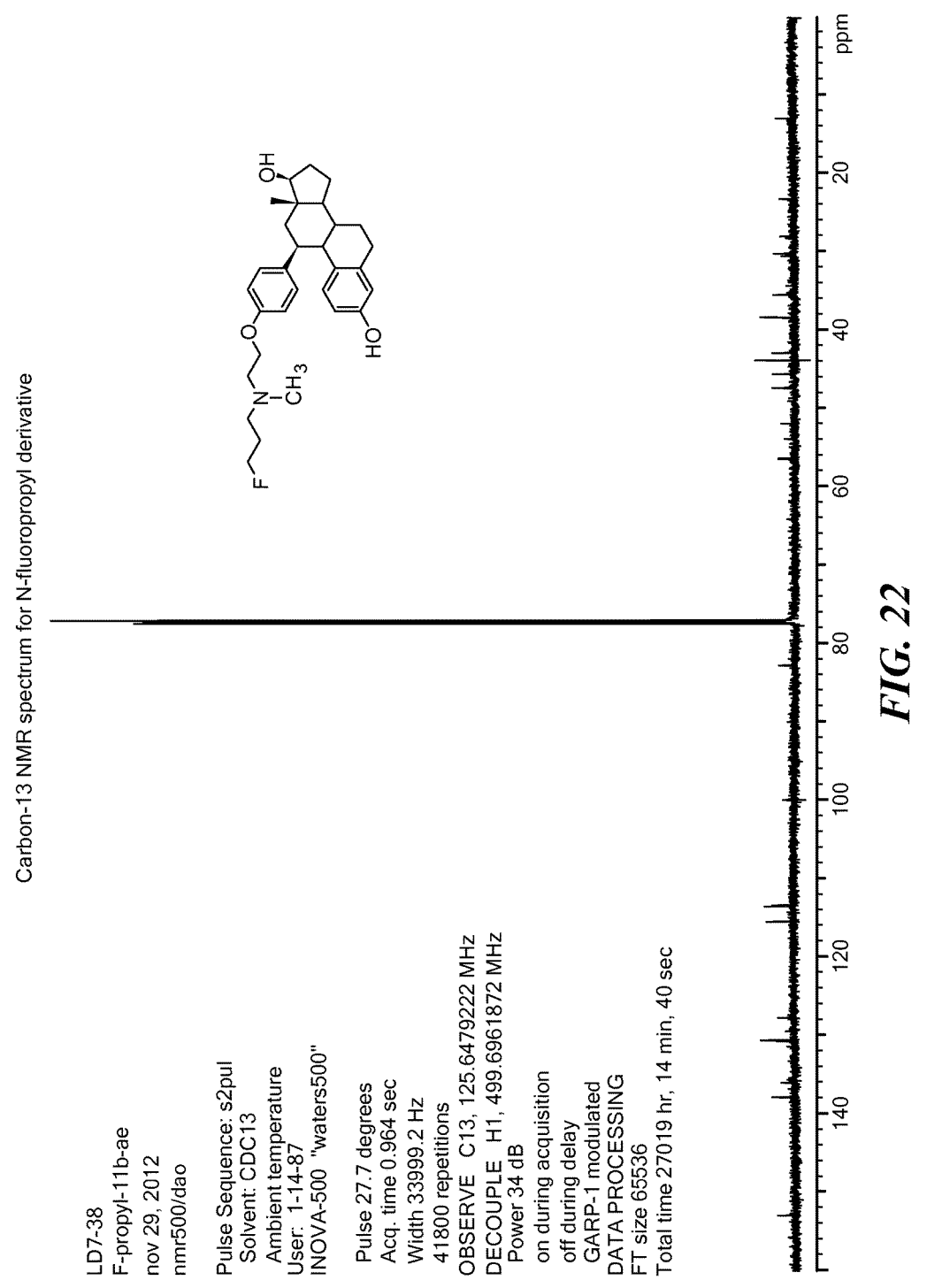

FIG. 22 is a carbon-13 NMR spectrum for the N-fluoropropyl derivative.

FIGS. 27A and 27B show mass spectra of the compounds depicted above the respective spectra.

FIG. 30C shows a summary of the data shown in FIG. 30B.

DETAILED DESCRIPTION OF THE INVENTION

Described herein are estrogen receptor (ER) targeted, 11β-aryl estradiol-based molecular imaging (MI) agents having high specific activity, high specific receptor binding affinity, and metabolic and clearance characteristics that render them useful as imaging agents for mammalian subject, including human subjects.

Previous structure activity relationship (SAR) studies of steroidal estrogens have indicated that small substituents at the 11β-position conferred agonist activity, usually with an increase of binding affinity (Dao et al., 2012, and Hanson, R. N.; Hua, E. et al., 2012, and references therein). Alkyl or heteroalkyl groups beyond 3-4 atoms in length have been shown to impart ER antagonist properties, often without a significant loss of binding affinity (Hanson, R. N.; Hua, E. et al., 2012, and references therein). Analysis of the properties of anti-estrogen-doxorubicin bioconjugates has shown that the 11β-aryl estradiol-based antiestrogens possessed several key features as potential candidates for MI for (ER+)-breast cancer (Dao et al., 2012). The 11β-aryl estradiol-based antiestrogens (AEs) retained high ER affinity, expressed ER antagonist properties, showed selectivity for ER-expressing cancer cells, and a linker between the steroid and doxorubicin improved pharmaceutical properties and allowed convergent attachment of different terminal groups.

The 11β-aryl group of the EAs of the present invention occupies a secondary pocket of the ER that extends to the surface. In the antagonist conformation, the 4'-position of the aryl group accesses the solvent-exposed space, thereby permitting further conjugation with the imaging moieties of the present invention without interference with receptor binding specificity.

The present invention employs a convergent strategy that allows the imaging tag component (imaging moiety), and the 11β-aryl estradiol-based antiestrogen component having a complementary linker at the 4'-position of the aryl group, to be prepared separately and then linked with an orthogonal ligation. Further, the preparation of labeled 11-β substituted estradiols described herein is modular. The imaging moiety and the 11-β substituted estradiol precursor are independently made with high yields and purity.

Figures 1, 7A:
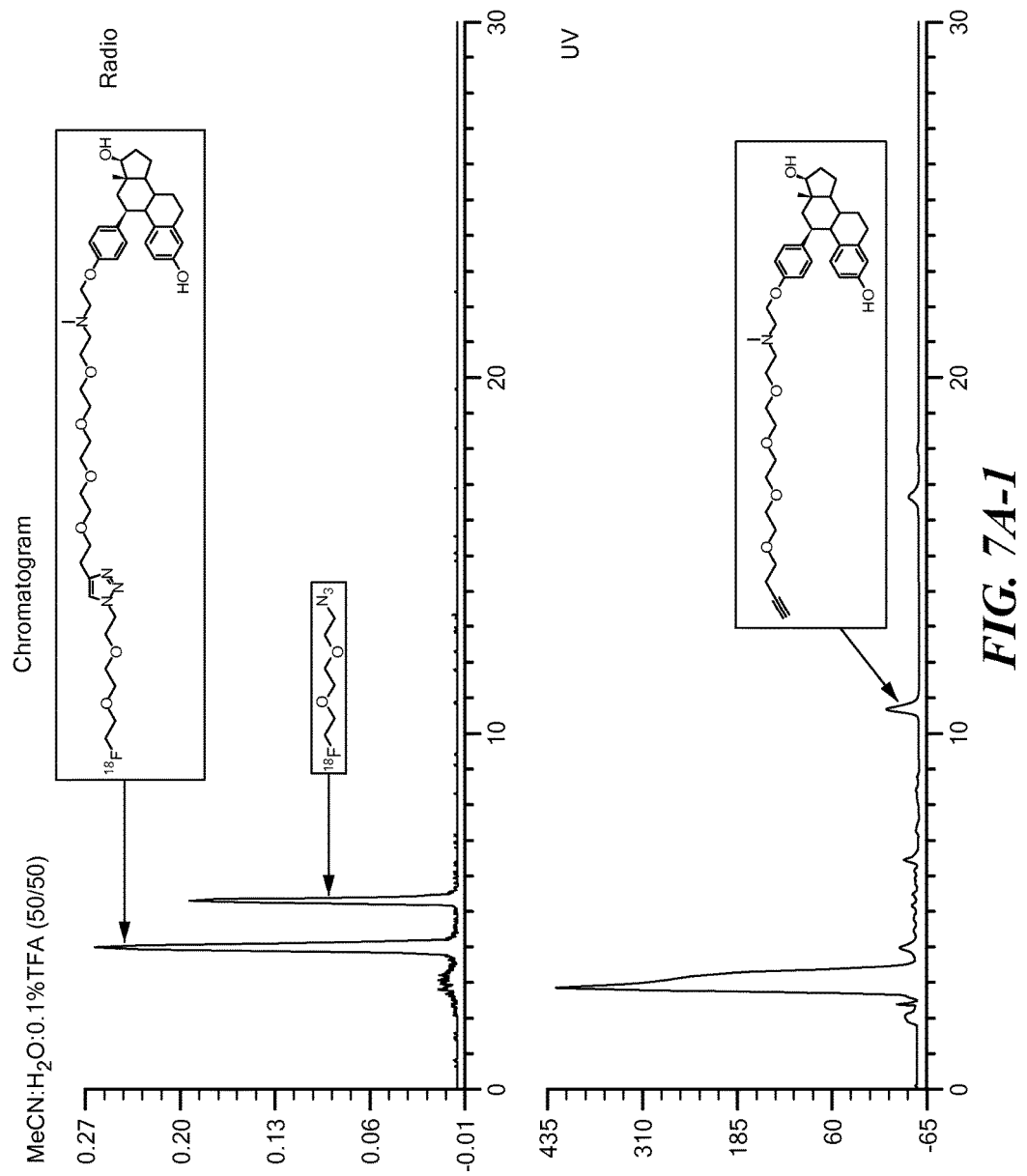
FIG. 7A shows preparative radio HPLC (high performance liquid chromatography) purification of the $^{18}$F radiolabeled 11β substituted estradiol product, under different chromatographic conditions. Peaks corresponding to the product and reactants are indicated by arrows.
Figures 2, 7A:
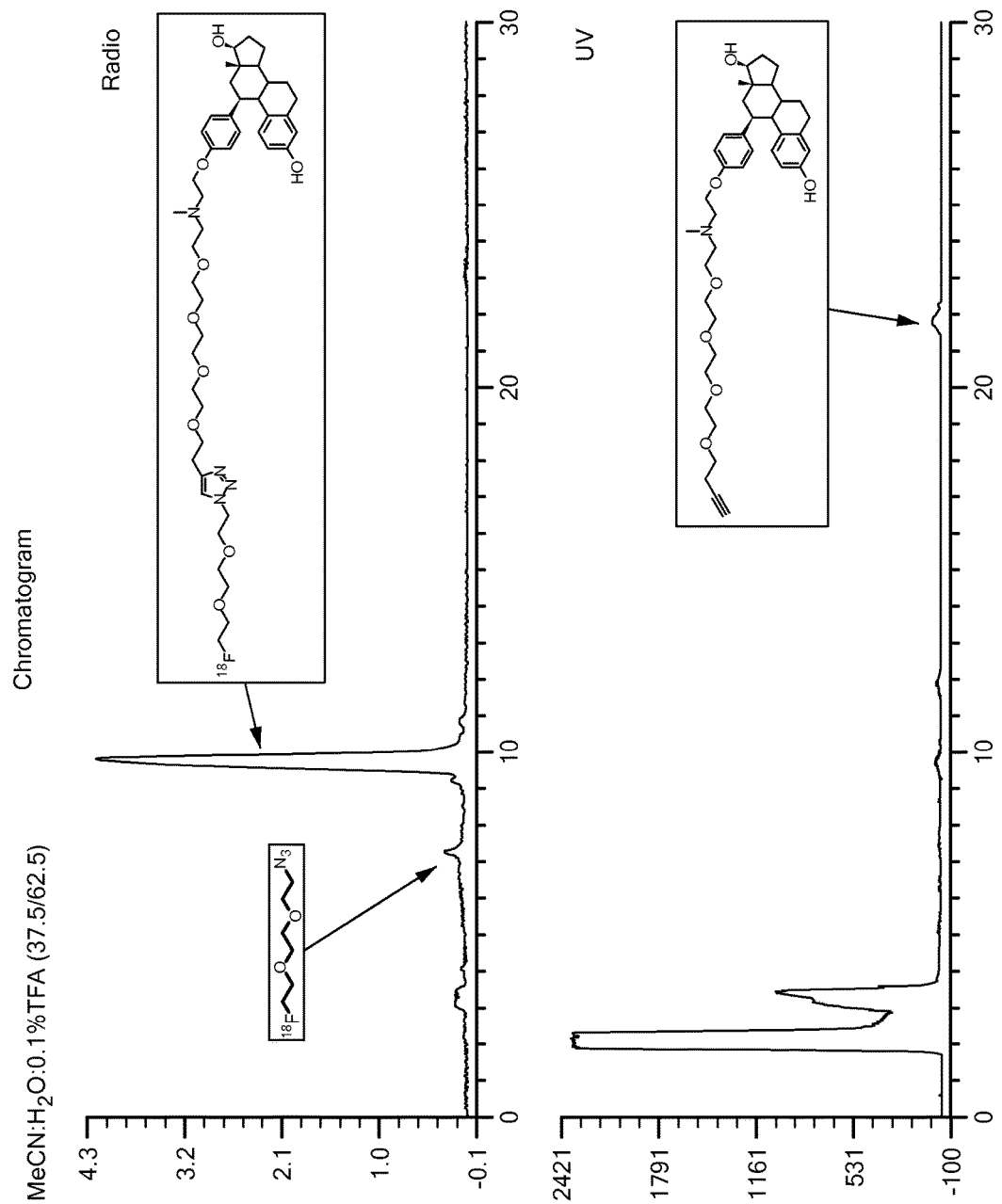
Figures 1, 7B:
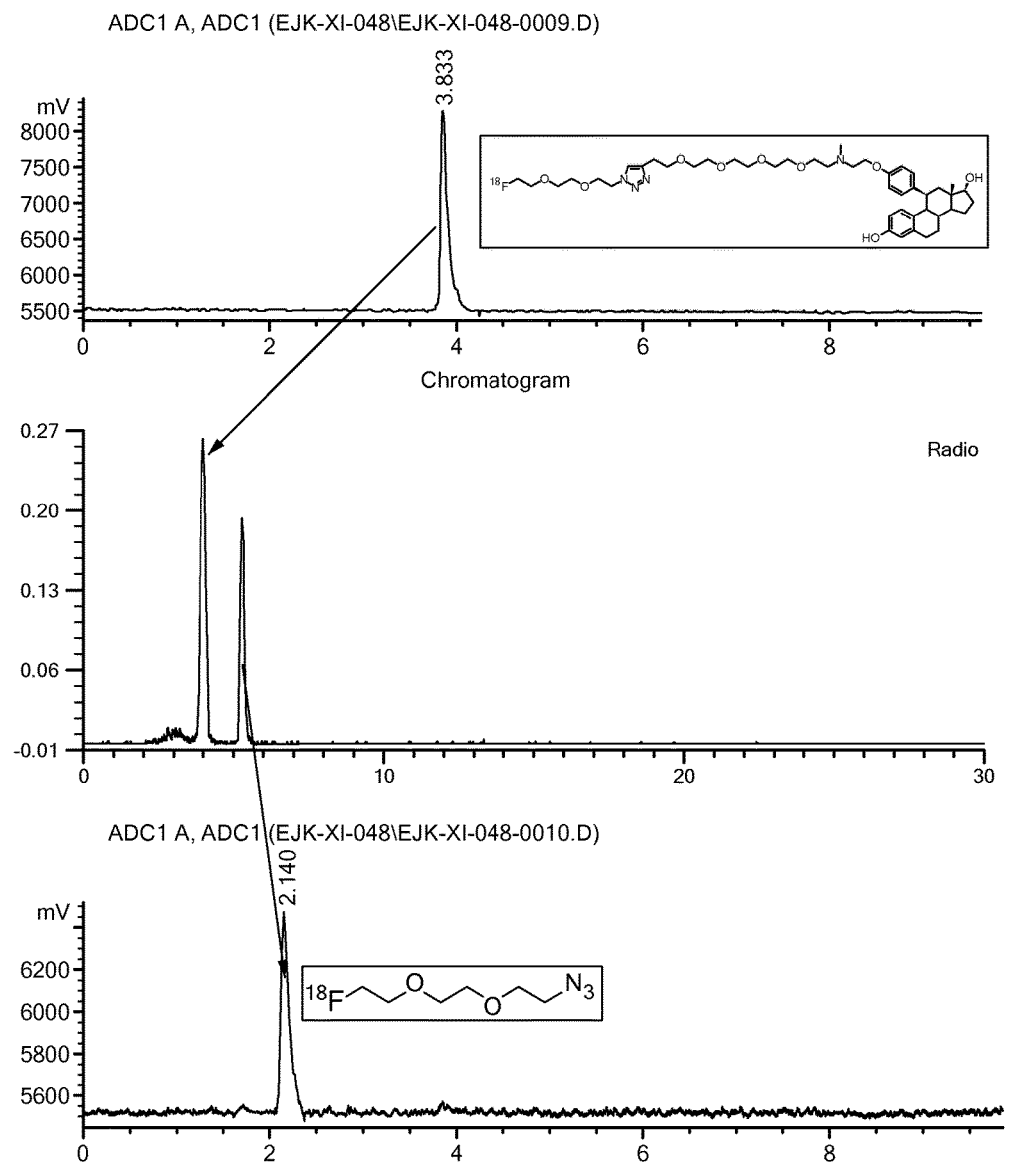
FIG. 7B shows radio HPLC traces confirming the assignment of peaks in the purification shown in FIG. 7A.
Figures 2, 7B:
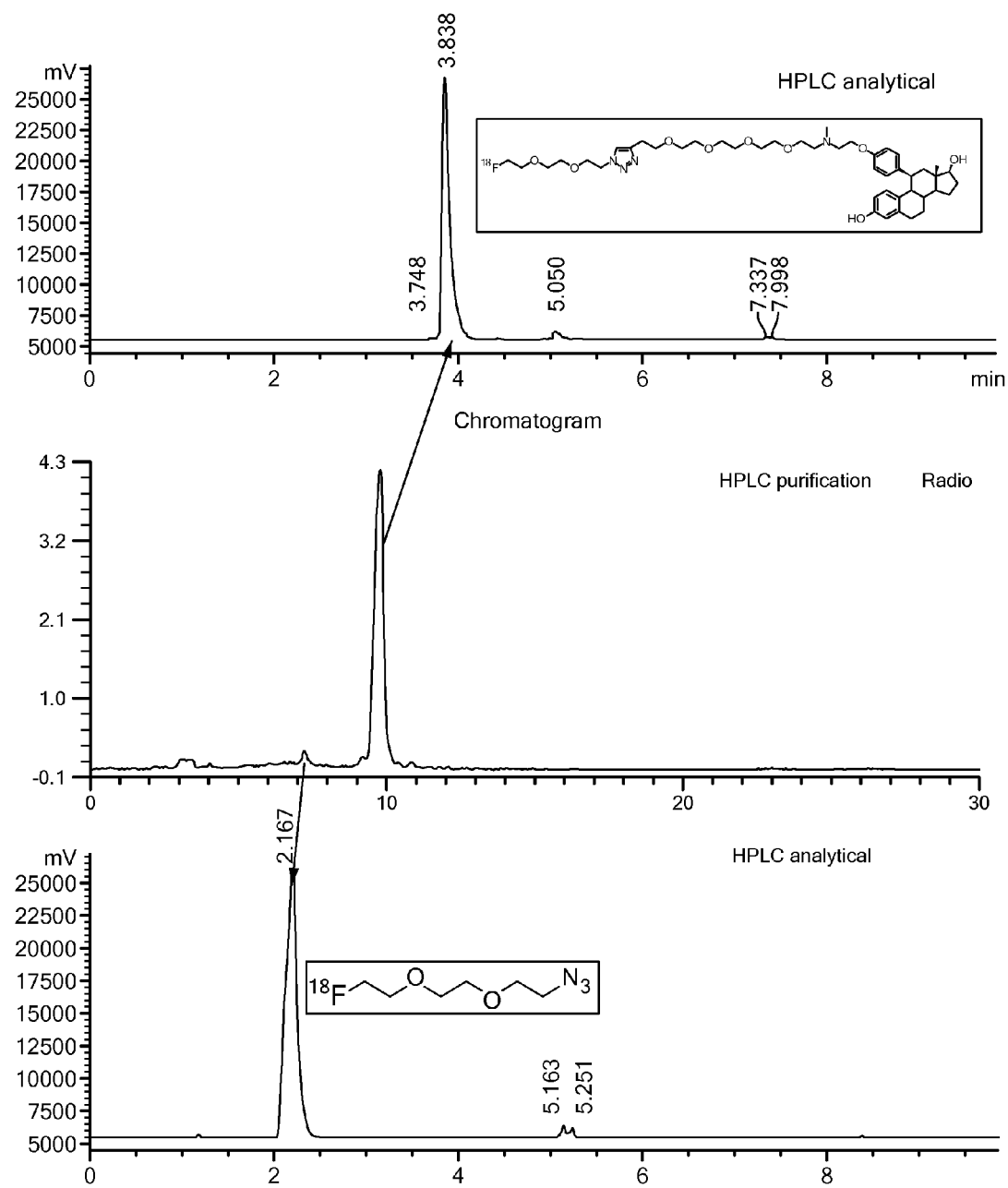

As a first step toward synthesis of 11β substituted estradiol-imaging conjugates having a radiohalogenated moiety, a high affinity alkynyl 11β-phenyl substituted estradiol component (9a) was prepared. Separately, an exemplary radio imaging label component, fluorinated triethylene azide (8b), was prepared. The compound, alkynyl 11β-phenyl substituted estradiol (9a), was prepared by two methods, both of which are shown in FIG. 2. The precursor was synthesized from estra-5(10),9(11)-diene-3,17-dione 3-ethylenedioxy ketal (1) and transformed into the key intermediate 11β-(4-Hydroxy-phenyl)-estra-4,9-diene-3,17-dione (3). An alkylation step was used to prepare the precursor 11β-[4-(2-dimethylamino-ethoxy)-phenyl]-estra-4,9-diene-3,17-dione (4).

Figure 1:
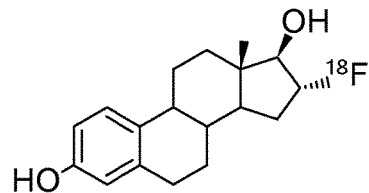
FIG. 1 shows the structures of a set of $^{18}$F-radiolabeled estradiols previously described (Bennink, R. J. et al., 2001; Pomper, M. G. et al., 1990; Kiesewetter, D. O. et al., 1984; VanBrocklin, H. F. et al., 1993; VanBrocklin, H. F., 1994; Seimbille, Y. et al., 2002).
Figure 1:
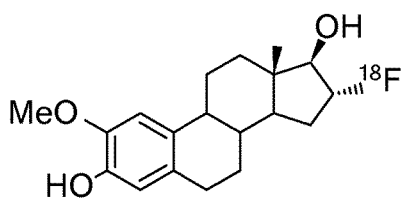
Figure 1:
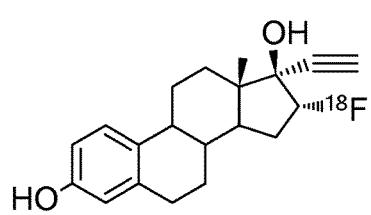
Figure 1:
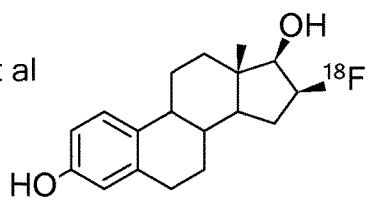
Figure 1:
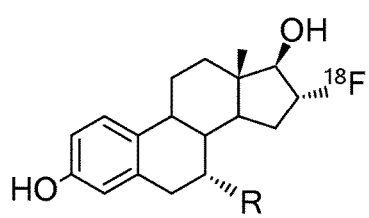
Figure 1:
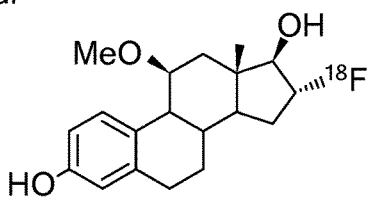
Figure 2A:
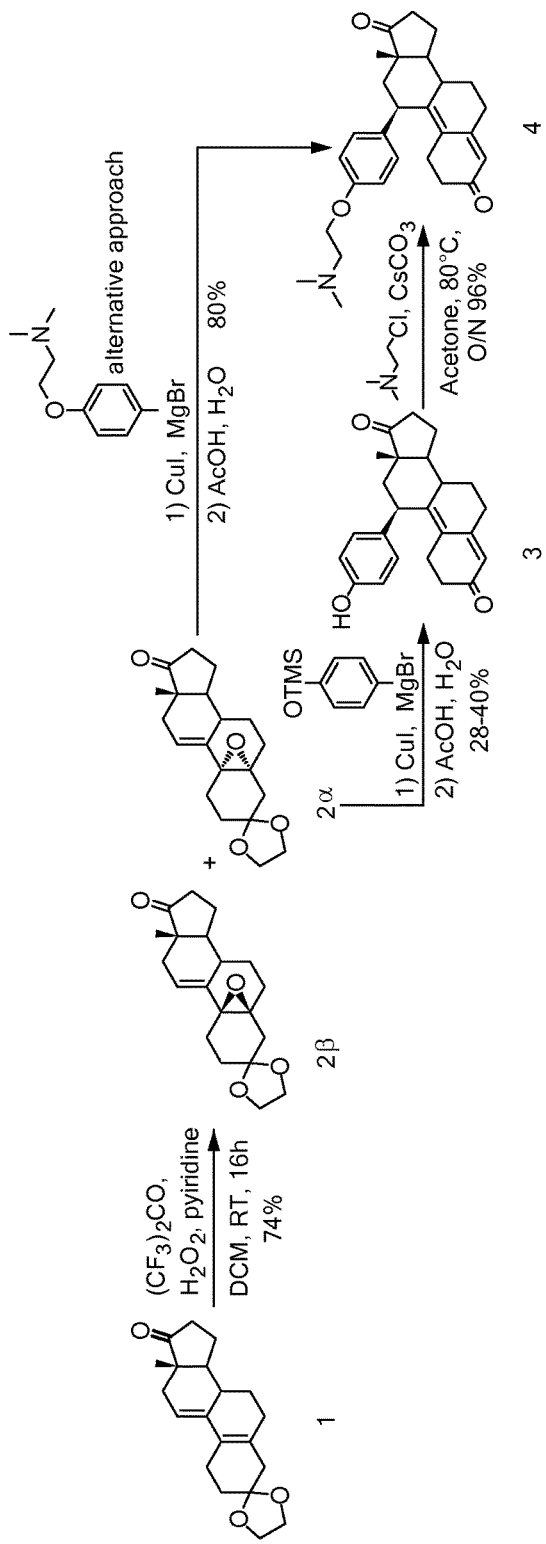
FIG. 2 is a diagram of a synthetic scheme for alkynyl and azido 11β-antiestrogen precursors.
Figure 2B:
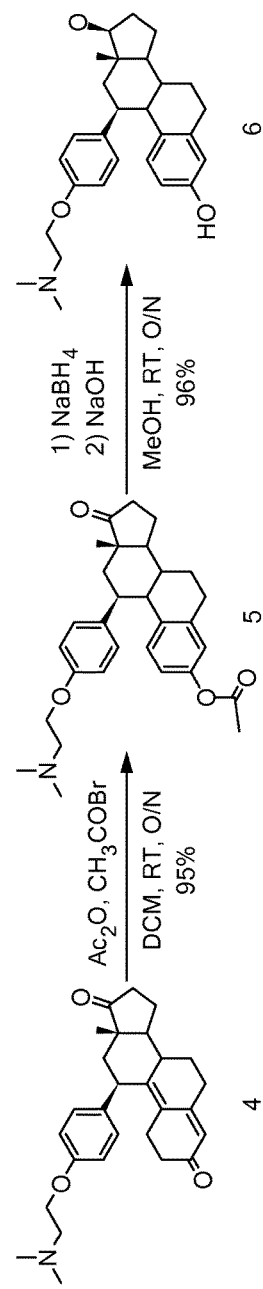
Figure 3:
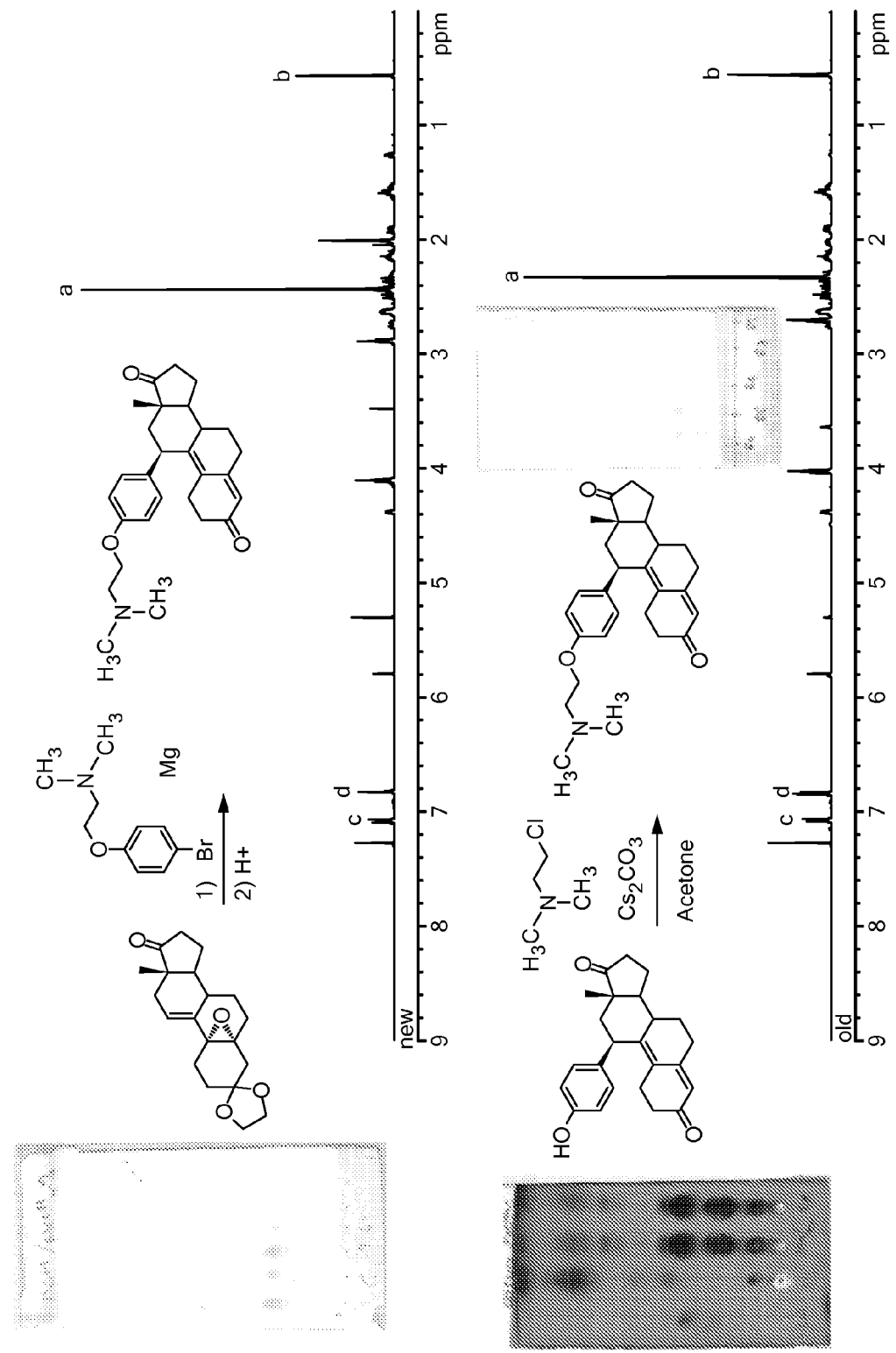
FIG. 3 is a comparison of NMR spectra and thin layer chromatograms associated with the syntheses of the intermediate 4 (FIG. 2) using a first approach (lower panel) and using a second (alternate) approach (upper panel).

Initially the dimethylaminoethoxy group was introduced after the 11β phenyl group to synthesize the intermediate (4). In an alternate approach the side chain was introduced prior to the Grignard reaction. In this route, 4-bromophenol was alkylated with dimethyl chloroethylamine to give 4-bromo-(2-dimethylaminoethoxy) benzene. The Grignard reaction was carried out as the next step to produce the intermediate (4). The alternate approach offered a number of advantages: the synthesis of the steroidal portion was shortened by one step; the yield of the product was higher, and the separation/isolation process was easier (FIG. 3). Further, the 4-bromo phenol starting material is significantly less expensive than the 1-bromo-(4-trimethysilyloxy) benzene, and reaction using the alternate approach was more reproducible than reaction according the initial scheme. Starting from the intermediate (4), the alkynyl antiestrogen was obtained as illustrated in the synthetic scheme shown in FIG. 2. The molecular imaging probe, such as an azido fluorinated ligand, can be attached using the "click" chemistry of azide-alkyne Husigen cycloaddition employing copper or ruthenium as a catalyst (FIG. 4, and Hanson, R. N. et al., 2012; Dao, K.-L. et al., 2012; Hanson, R. N.; Hua, E. et al., 2012; Adam, H. J. et al., 2012; Dao, K.-L. et al., 2013; Haddad, T. et al., 2012; Hanson, R. N.; Hua, E.; Adam, H. J. et al., 2012; Hanson, R. N.; Kirss, R. et al., 2012; Hanson, R. N.; McCaskill, E. et al., 2012; Olmsted, S. L. et al., 2012).

Figure 4:
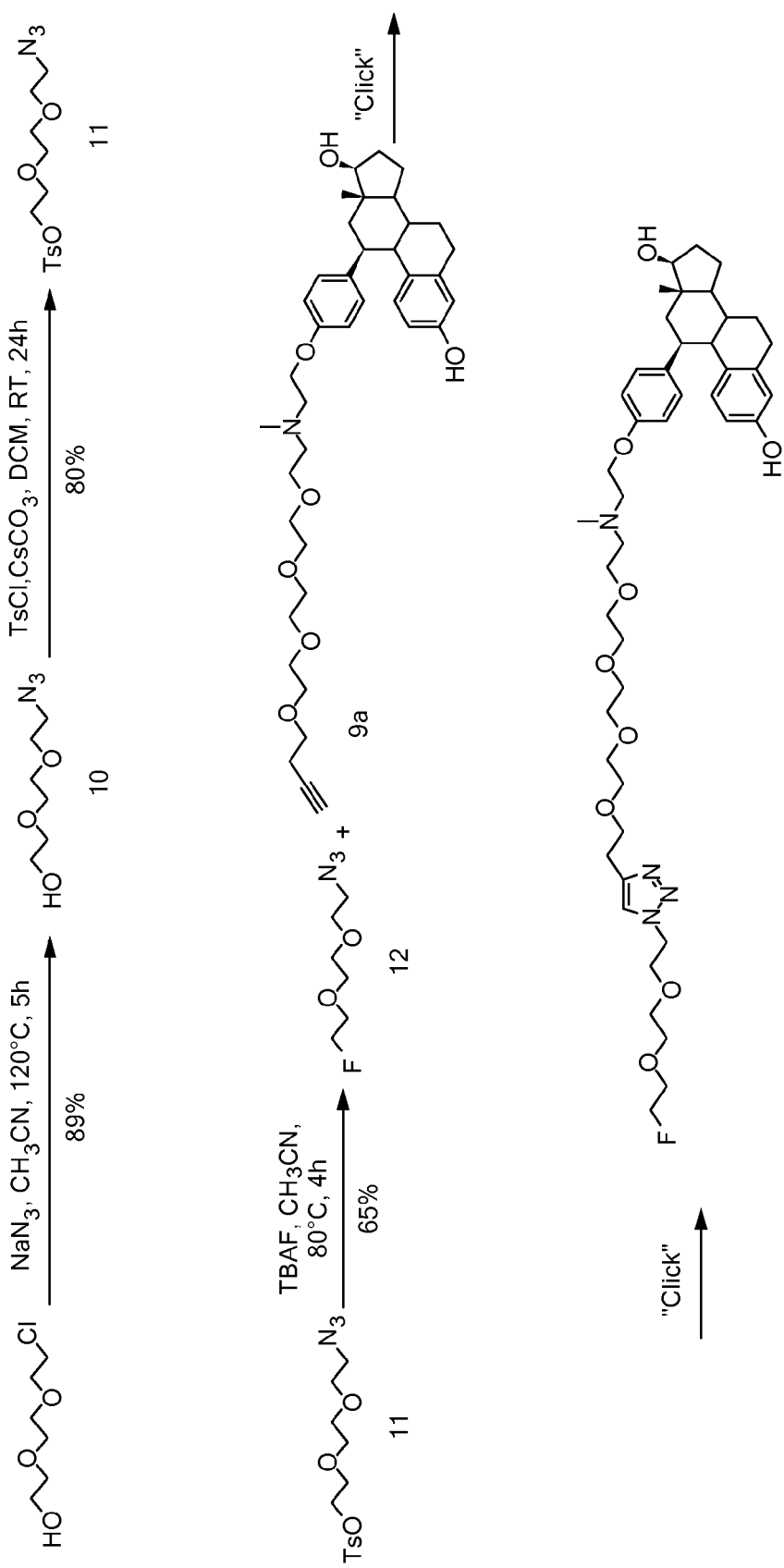
FIG. 4 is a diagram of a scheme for convergent synthesis of $^{18}$F-radiolabeling of 11β-substituted antiestrogen.

The preparation of the fluorinated component proceeded in good overall yield. The synthesis began with the ω-chloro triethylene glycol derivative which underwent displacement with sodium azide to give (10) (FIG. 4). Tosylation gave intermediate (11), which was treated with tetra-n-butylammonium fluoride (TBAF) to give the fluorinated precursor (12). Conversion to the final product 15 was achieved in good yields using classical "click" conditions. All of the intermediates and final products were characterized by IR, NMR, and LC-MS. The convergent modular approach proved to be a successful strategy for assembling the target anti-estrogen (AE).

Figure 5:
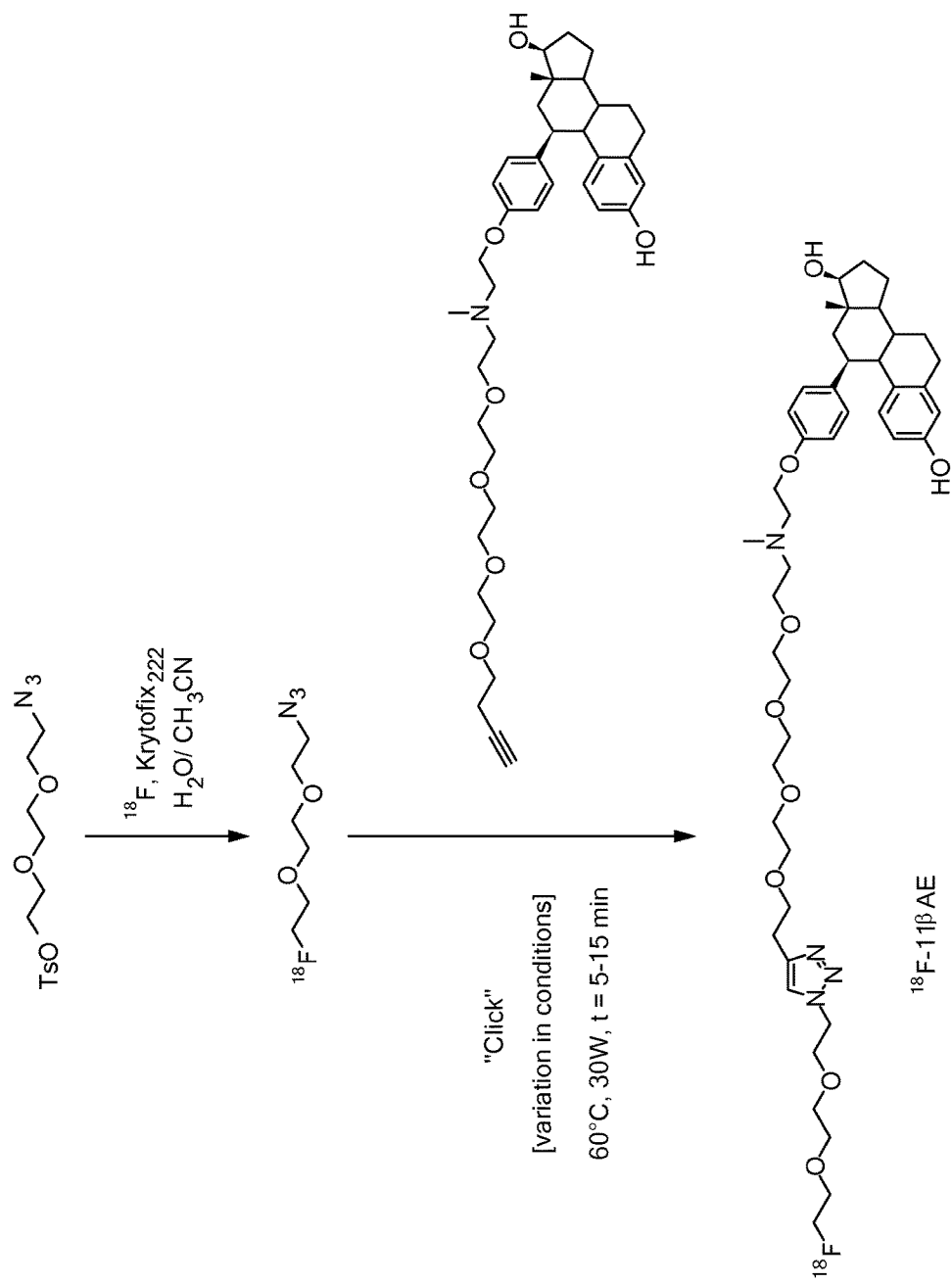
FIG. 5 is a diagram of a scheme for synthesis of $^{18}$F radiolabeled 11β substituted estradiol showing variation in "click" chemistry conditions.
Figure 6A:
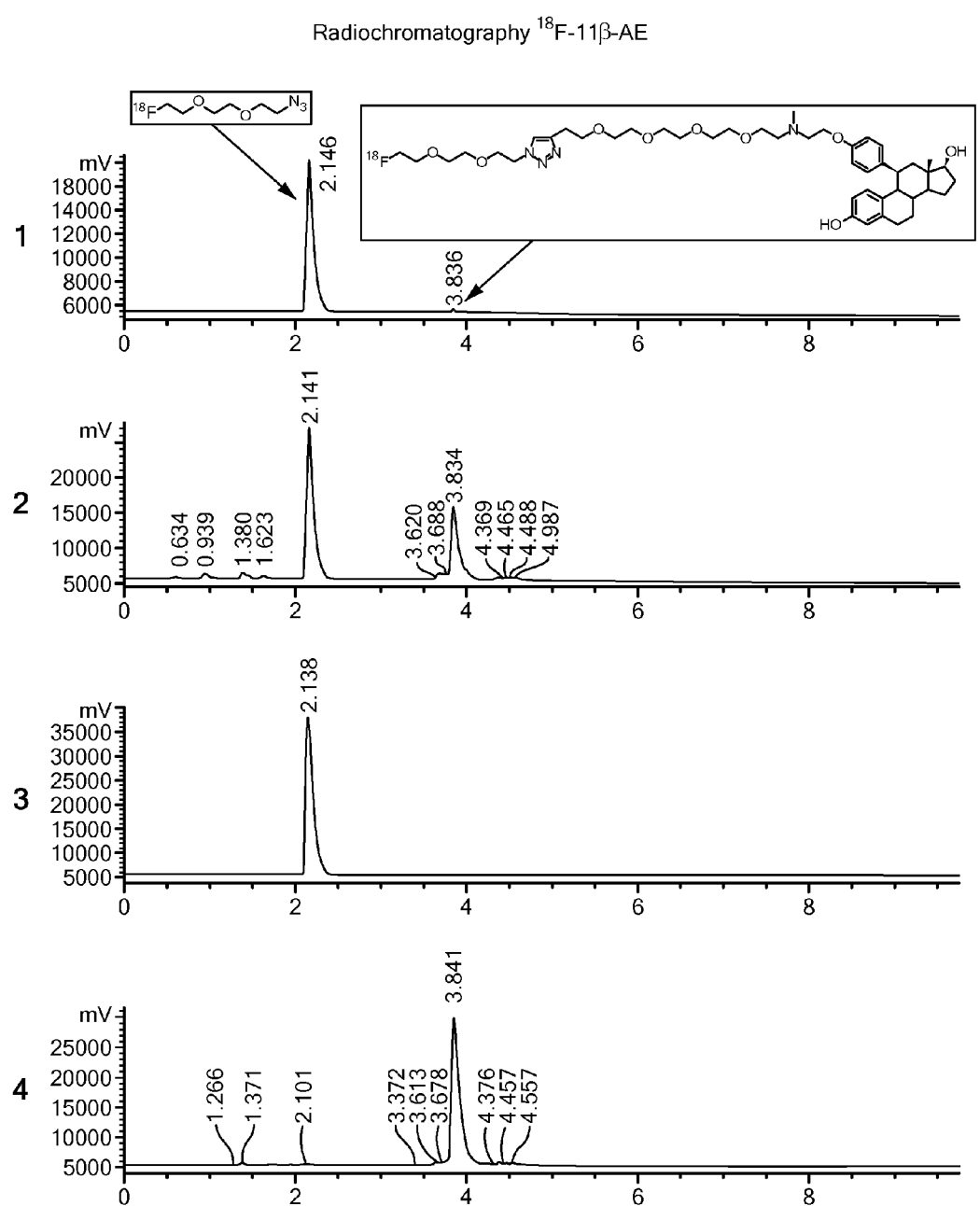
FIG. 6 is a diagram showing eight different "click" reactions (right) performed, and radiochromatographic purifications (left) for the synthesis of $^{18}$F radiolabeled 11β substituted estradiol.
Figure 6B:
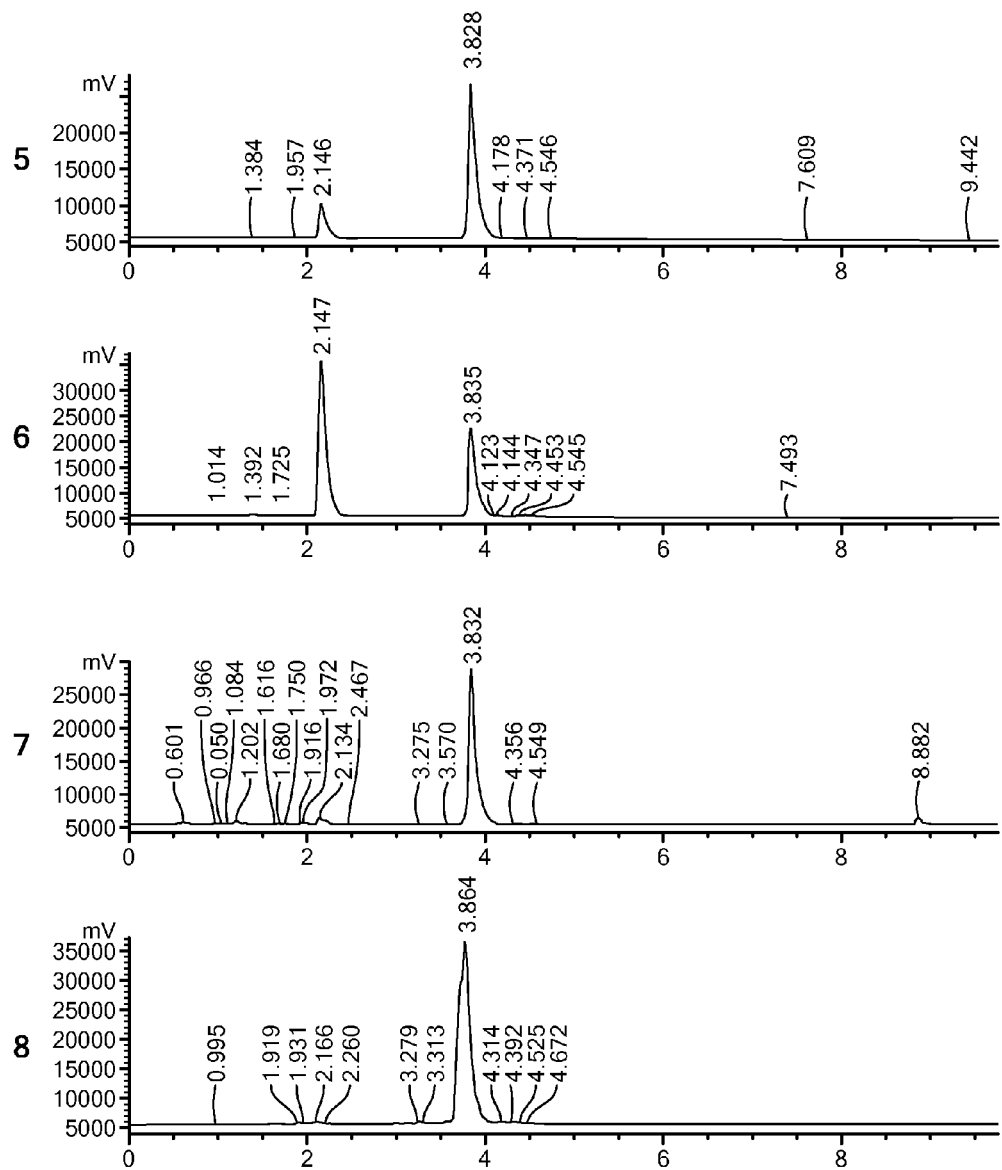

To synthesize 11β-AE radiolabeled with $^{18}$F as shown in the structure in FIG. 5, a variety of different "click" conditions were investigated to determine the best method to convert the alkynated AE precursor into the radiolabeled "click" products. Because of the short half-life of $^{18}$F radionuclide, it is necessary that the conversion method be fast and proceed in high yield. The Table in FIG. 6 summarizes the "click" reactions that were carried out with a pre-automated synthesizer (Center for Systems Biology, Mass General Hospital, Boston, Mass.). As the results in the radioHPLC trace (FIG. 5) indicate, the in situ "click" reaction in conditions 4, 7, and 8 gave the best radiochemical yields for the conversion of $^{18}$F-PEG-N$_3$ to the $^{18}$F-AE radioligand. However, method 4 involved an additional ligand, bathophenantrolinedisulfonic acid disodium salt (BPDS) in a mixture of DMSO/H$_2$O (50:50), potentially resulting in more impurities requiring HPLC purification. Although, the radiochemical yield for method 7 was lower, the reaction conditions are much simpler, and only one catalyst copper (I) tetrakis(acetonitrile)copper(I) hexafluorophosphate was used. In reaction 8, 40 μL of 80 mM BPDS was added to the scale up reaction to ensure that adequate amount of Cu$^{+1}$ was formed, and was available for catalyzing throughout the "click" reaction. Indeed, this method gave 95% conversion and produced isolated yields ranging from 9.73 mCi to 9.12 mCi. All the reactions in FIG. 5 used microwave synthesis conditions (temp 60° C., power 30 watts, and 5 minutes), except method 7 in which a 10 min irradiation time was used.

Use of MeCN:H$_2$O (50:50) with 0.1% TFA as the solvent for HPLC purification resulted in elution of the radiolabeled antiestrogen product at 5 minutes, followed closely by $^{18}$F-PEG-N$_3$ at about 6 minutes. Changing the eluting solvent to MeCN:H$_2$O (37.5:62.5) with 0.1% TFA resulted in improved separation, with the $^{18}$F-radiolabled 11β-substituted antiestrogen eluting at about 10 min, $^{18}$F-PEG-N$_3$ eluting at about 7.5 min, and the alkyne precursor eluting at 22 minutes (UV HPLC trace).

Results of preperative radioHPLC of the $^{18}$F labeling "click" product and radioHPLC analysis of the separated compounds demonstrated that 11β-AE described herein (9a; FIG. 4) can be radiolabeled with $^{18}$F radionuclide using click chemistry with the azido-PEG-$^{18}$F ligand (12). The method of synthesis gave a sustainable high activity conversion, and the HPLC purification scheme indicated that the labeling compound is 100% pure (FIG. 7) and is suitable for in vivo imaging.

Figure 8A:
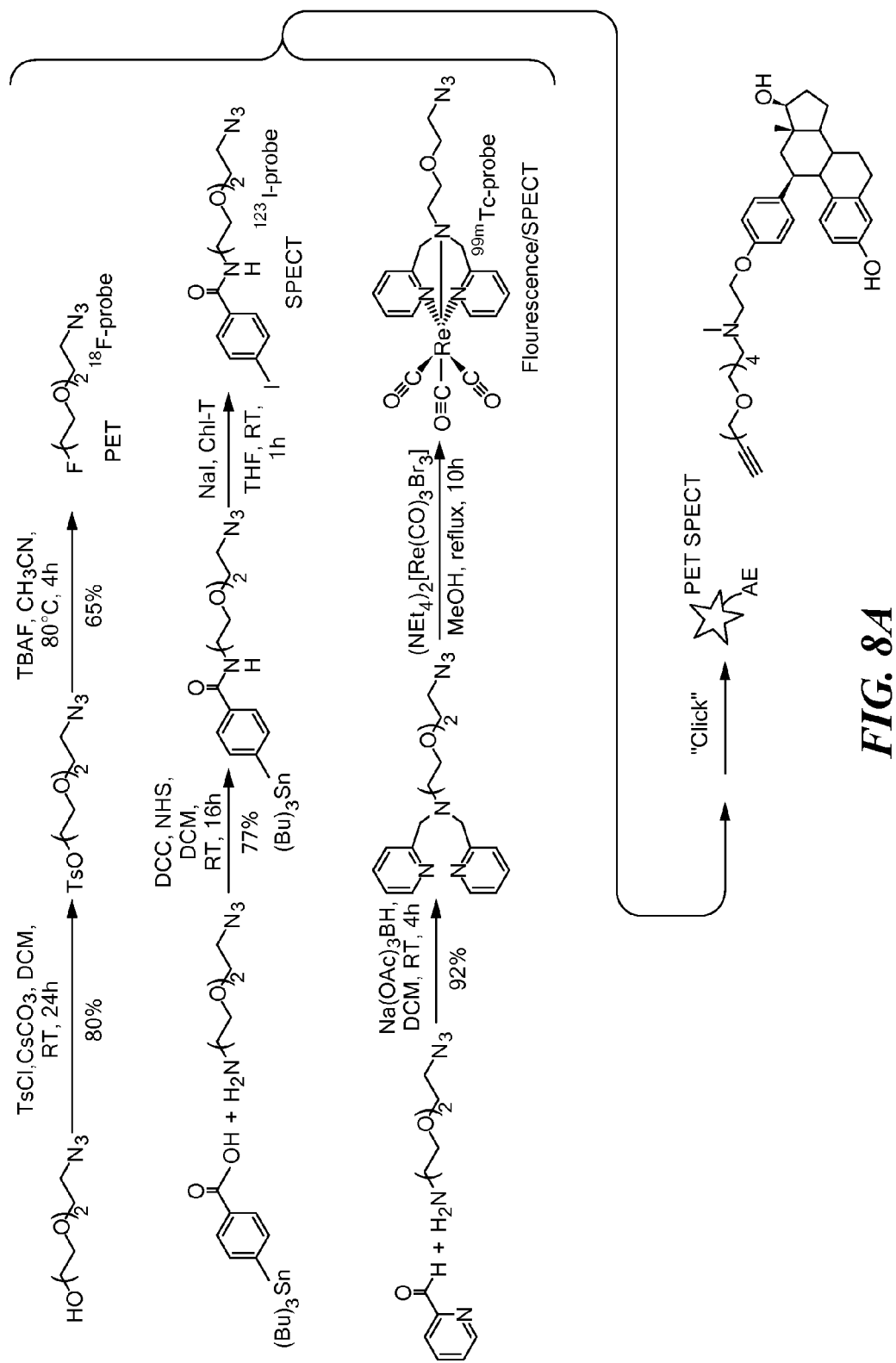
FIG. 8 is a diagram showing attachment of different imaging modalities to the alkynyl 11β-antiestrogen precursor of FIG. 2 using "click" chemistry.
Figure 8B:
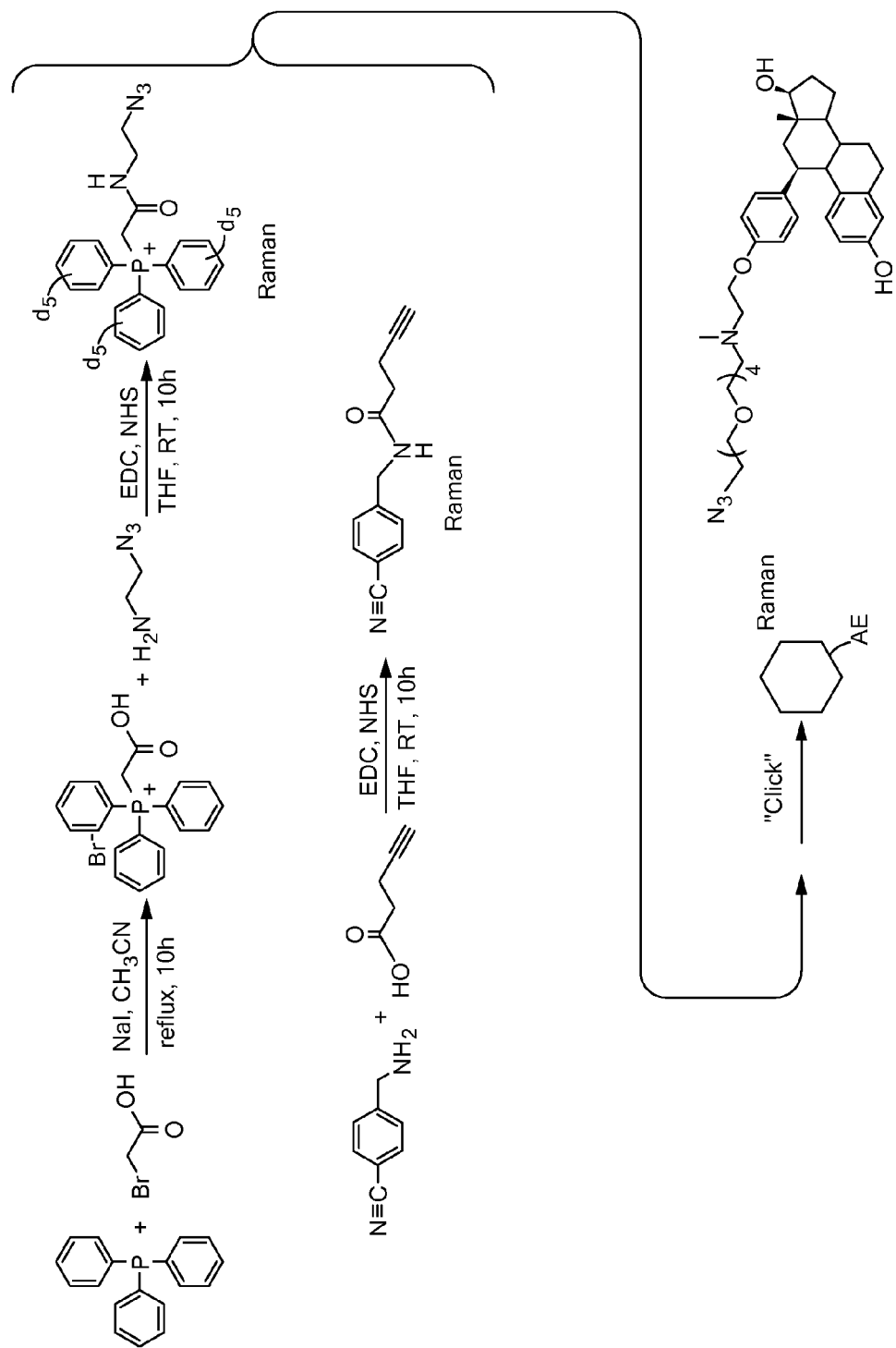
Figure 8C:
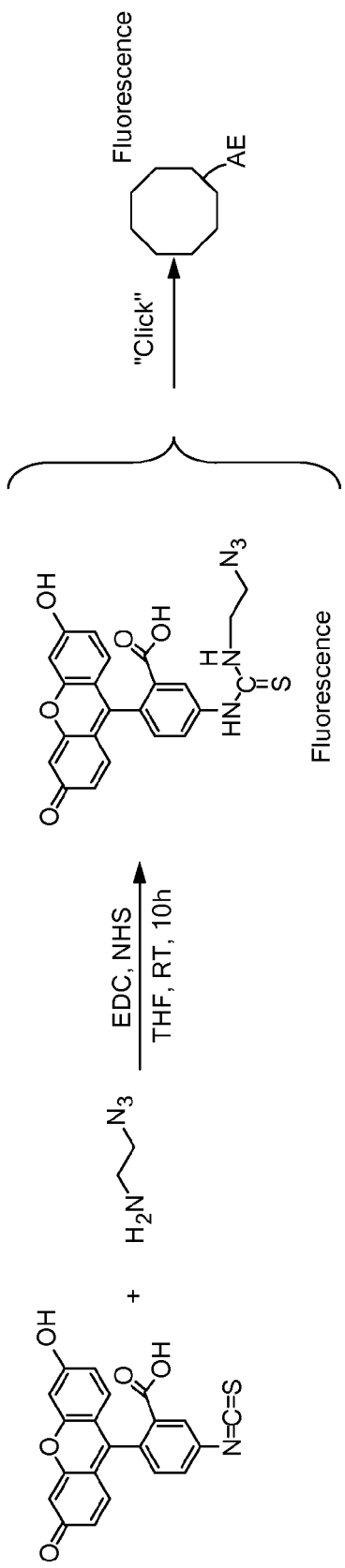
Figure 9:
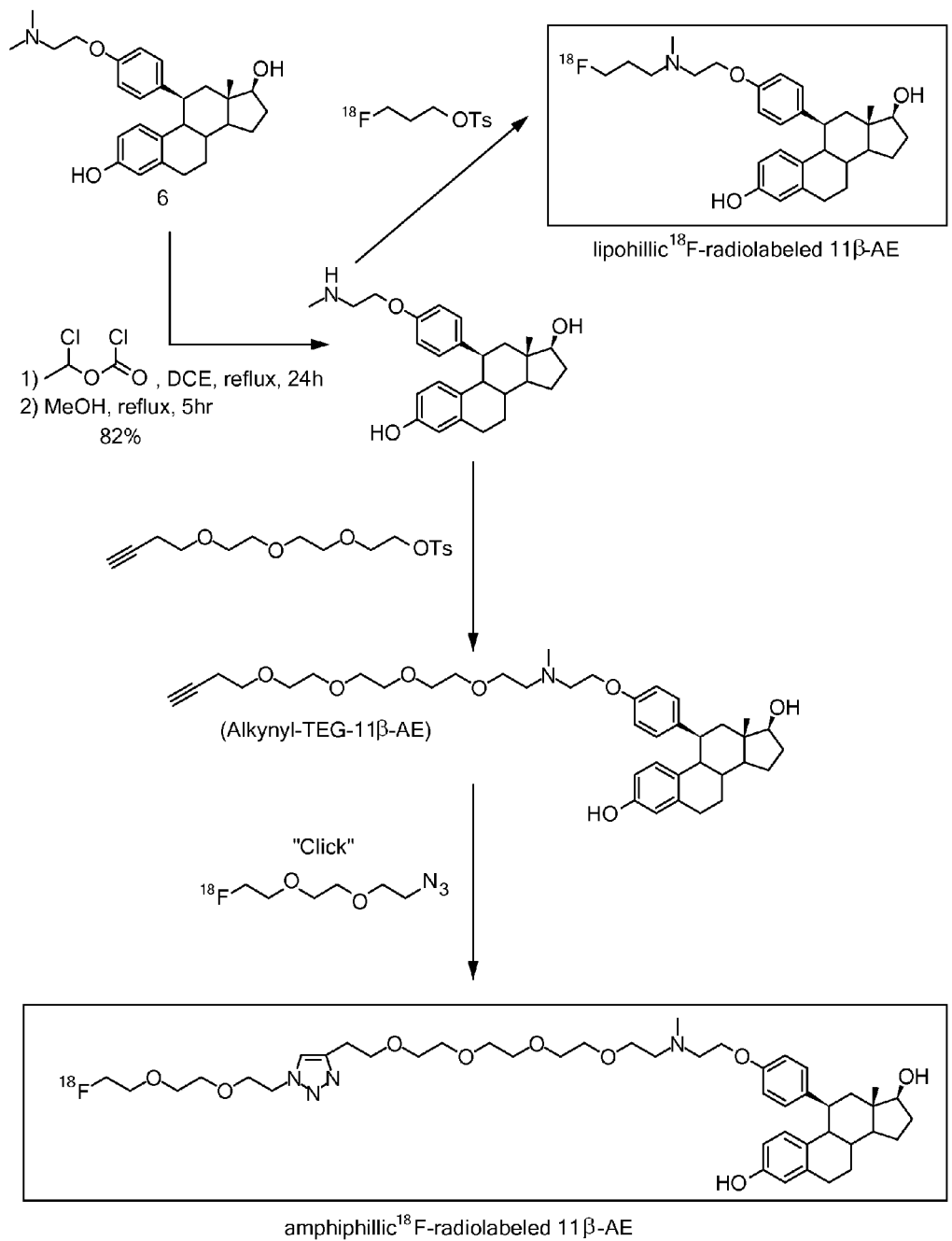
FIG. 9 is a diagram showing synthesis of a lipophilic $^{18}$F radiolabeled 11β antiestrogen in addition to an amphiphilic $^{18}$F radiolabeled 11β antiestrogen.
Figure 10:
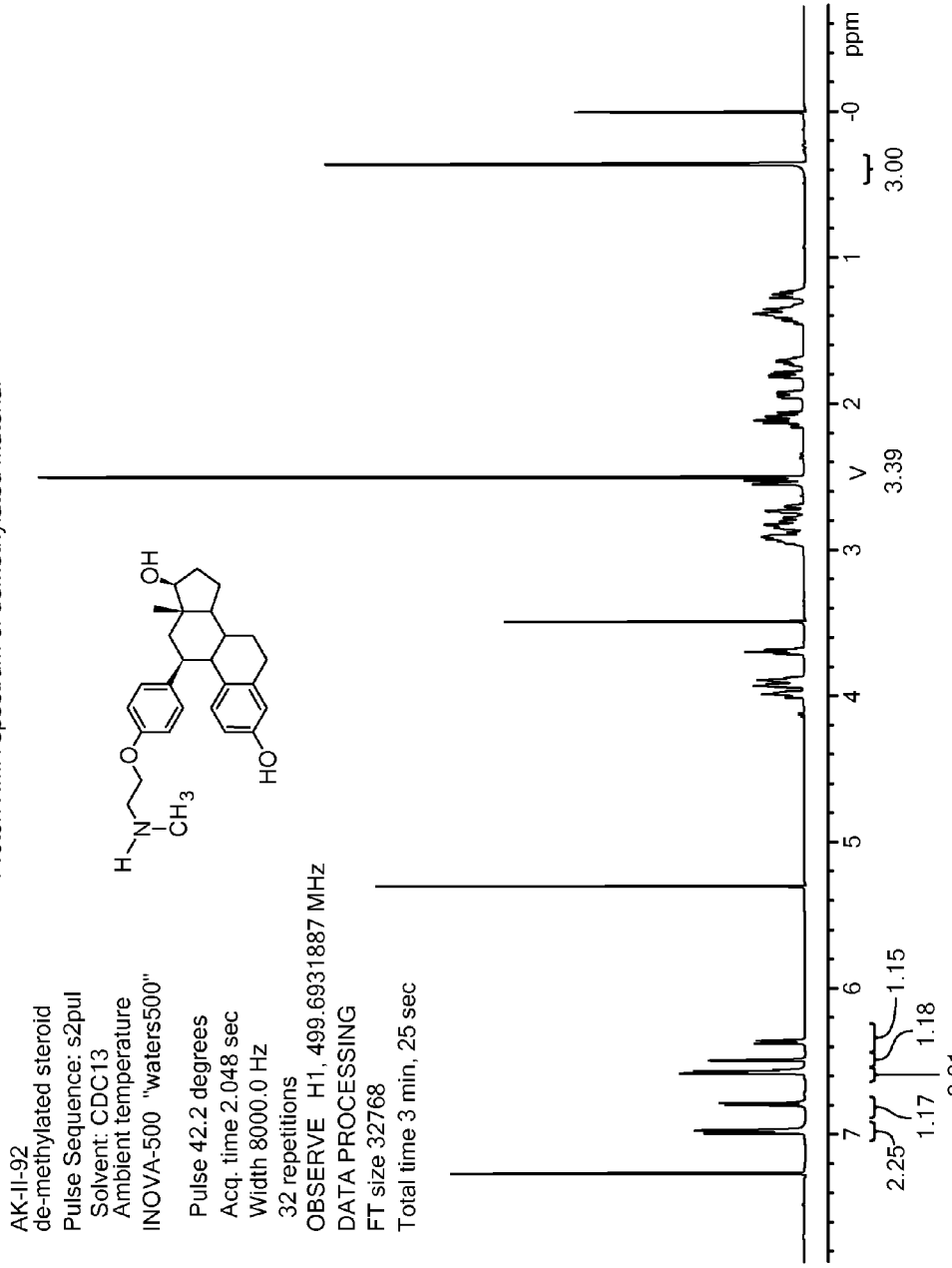
FIG. 10 is a proton NMR spectrum of demethylated material.
Figure 11:
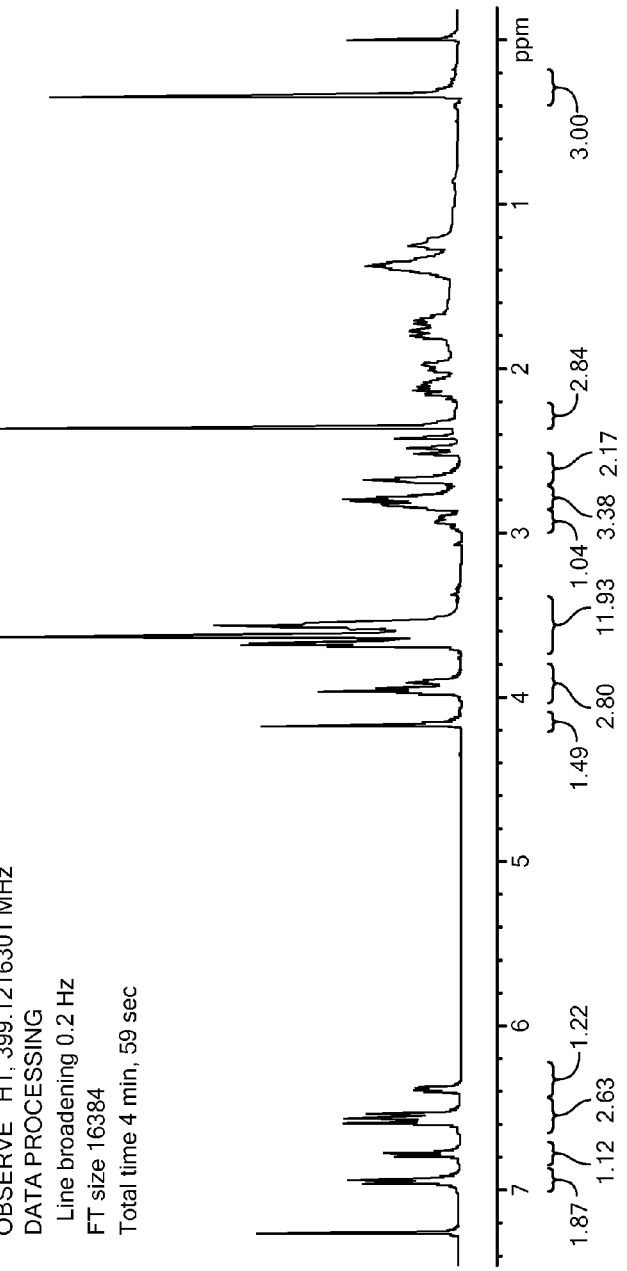
FIG. 11 is a proton NMR spectrum of material with propargyl tetraethylene glycol linker.
Figure 12:
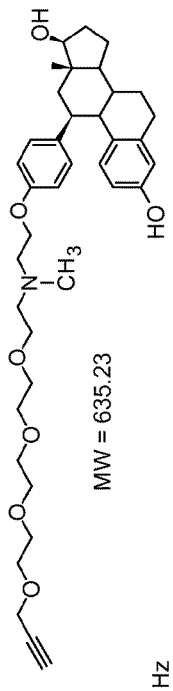
FIG. 12 is a carbon-13 NMR spectrum of material with propargyl tetraethylene glycol linker.
Figure 12:
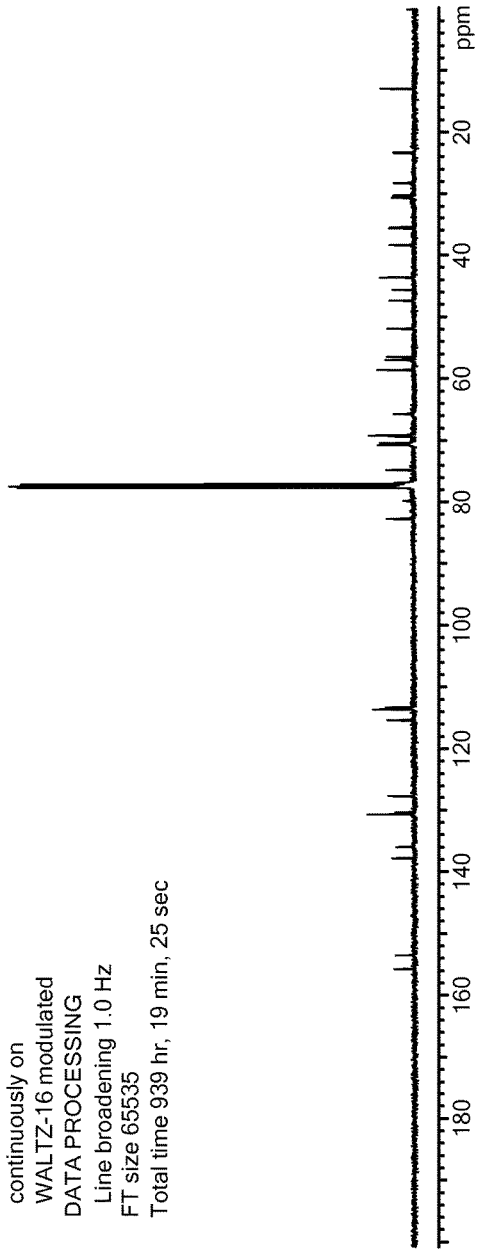
Figure 13:
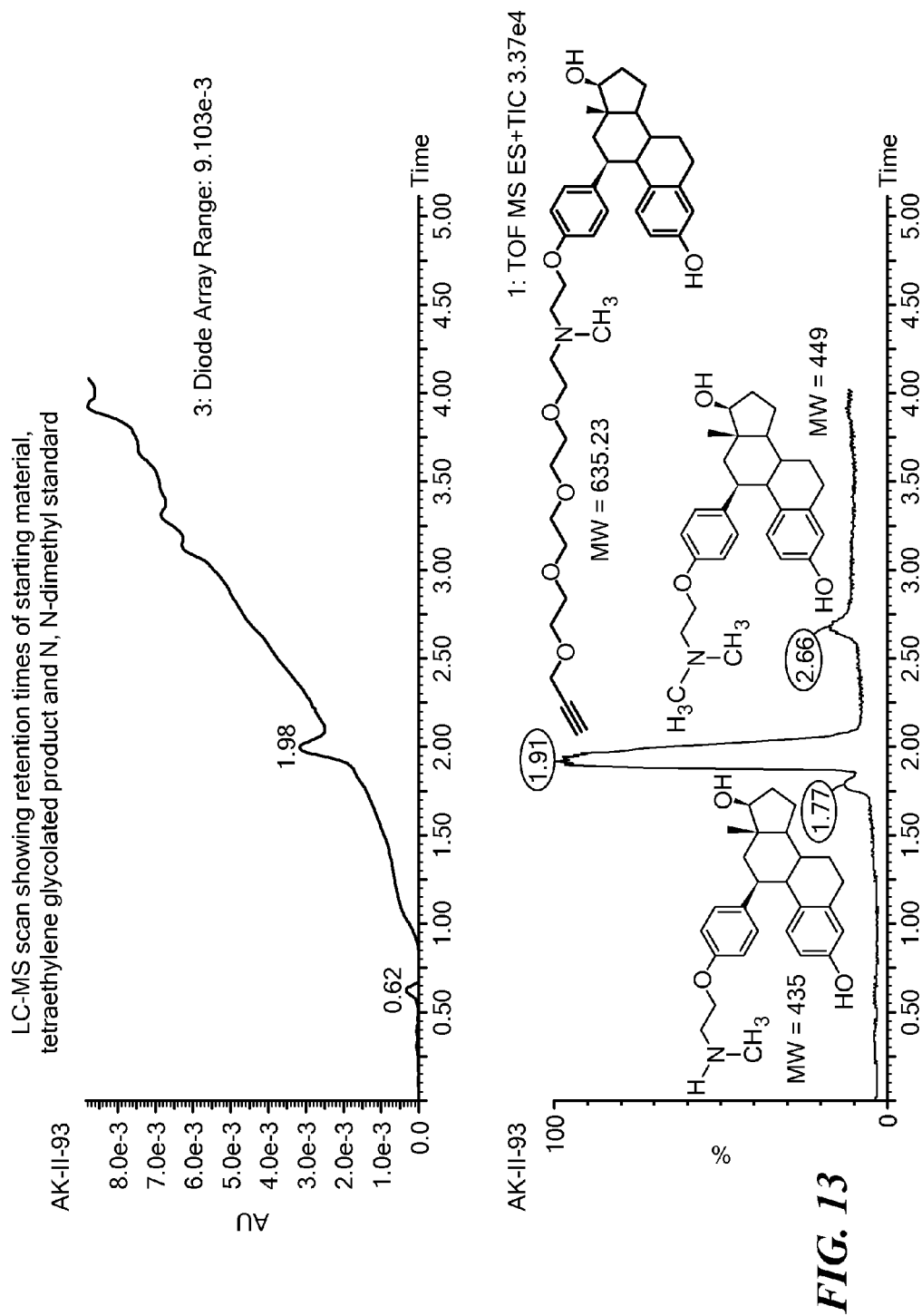
FIG. 13 shows an LC-MS scan showing retention times of starting material, tetraethylene glycolated product, and N,N-dimethyl standard.
Figure 14:
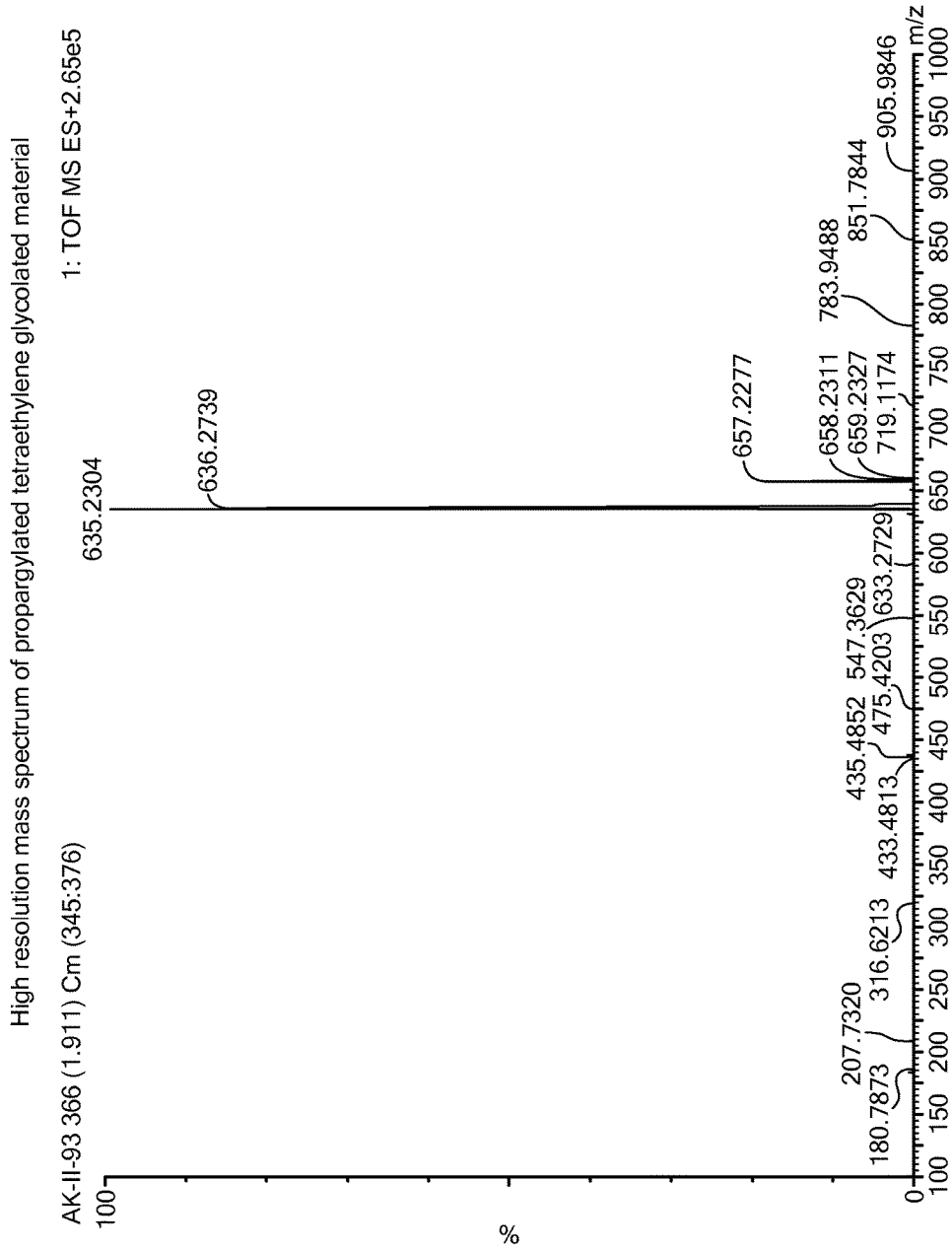
FIG. 14 is a high resolution mass spectrum of propargylated tetraethylene glycolated material.
Figure 15:
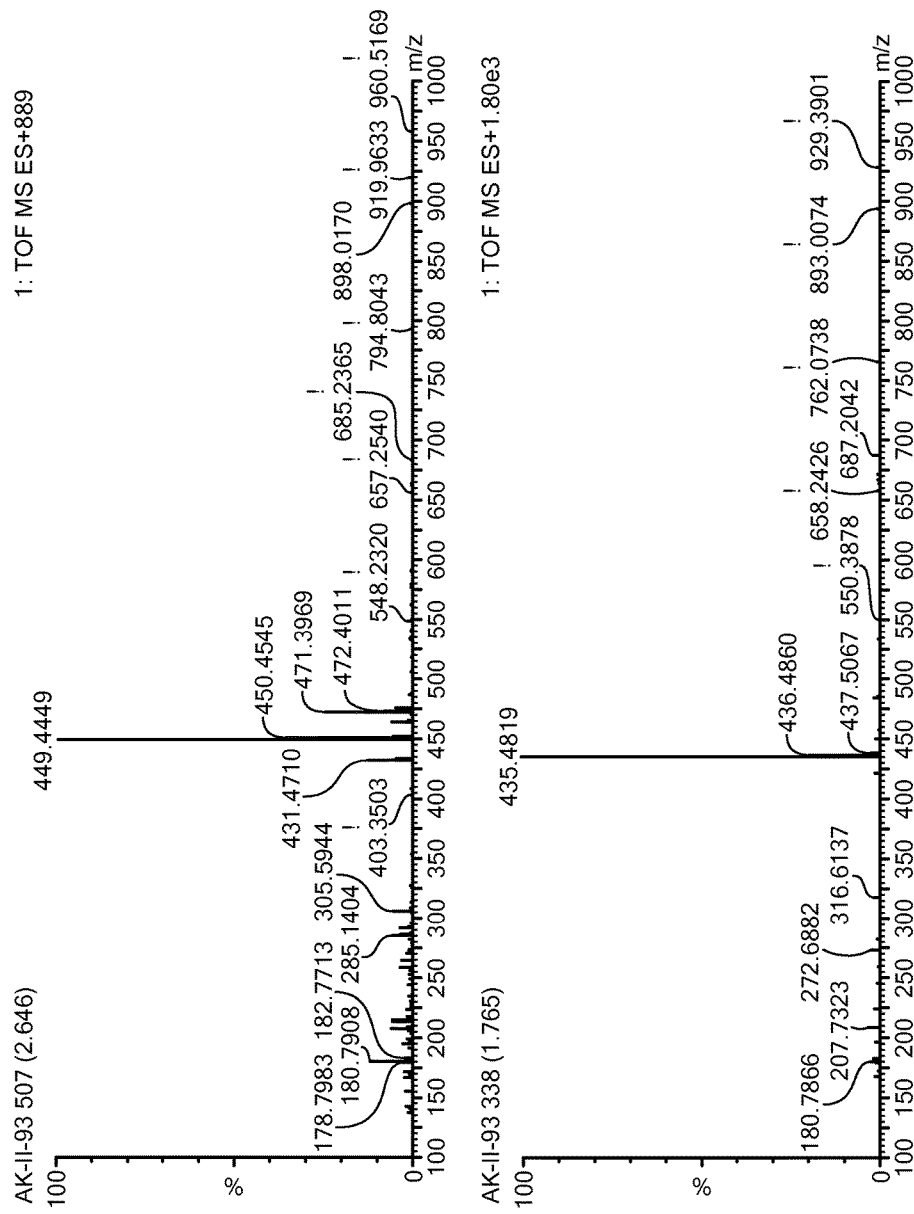
FIG. 15 shows high resolution mass spectra of N-demethylated material.
Figure 16:
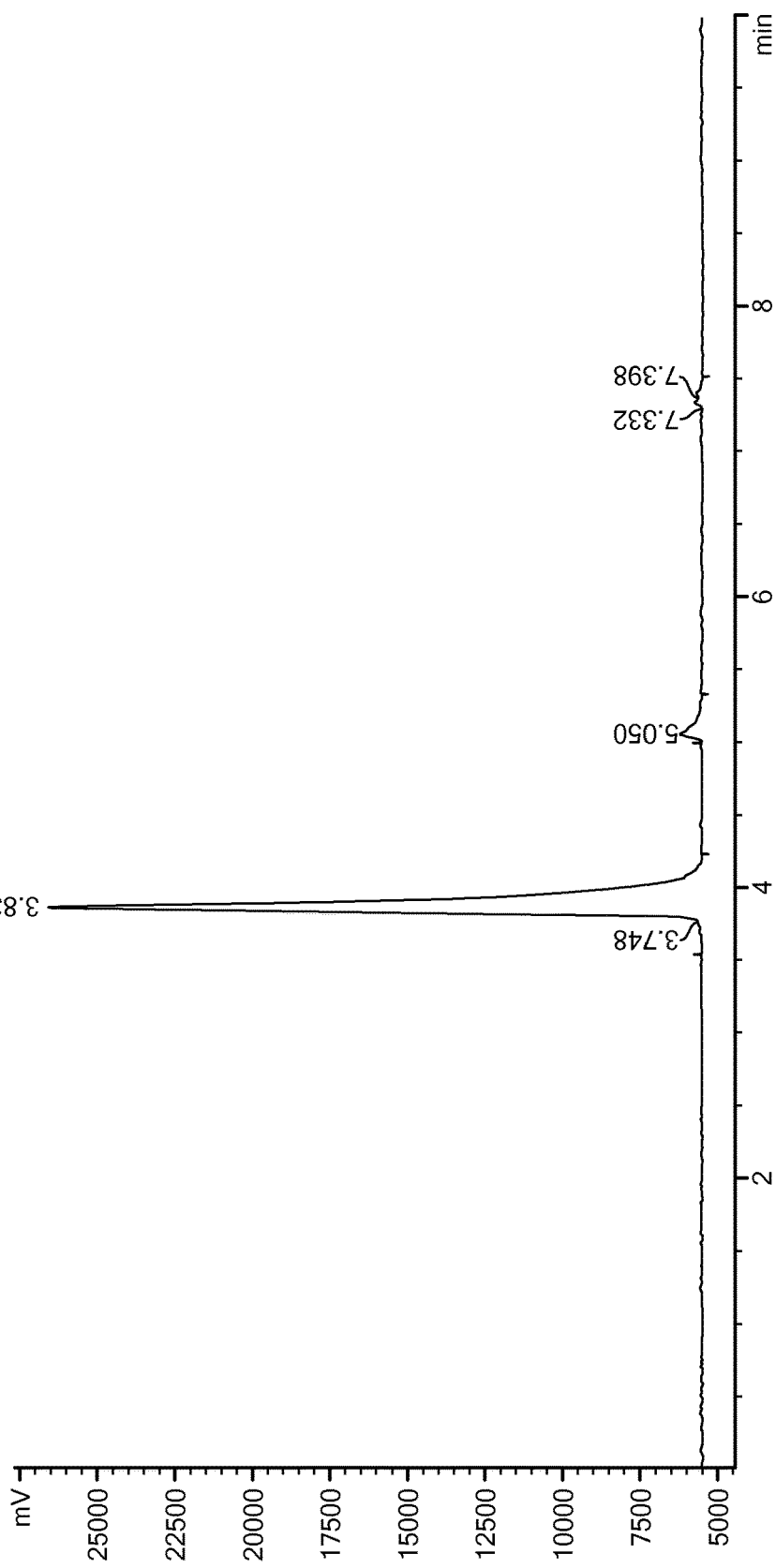
FIG. 16 shows an HPLC trace indicating the purity of propargyl tetraethylene glycolated material.
Figure 17:
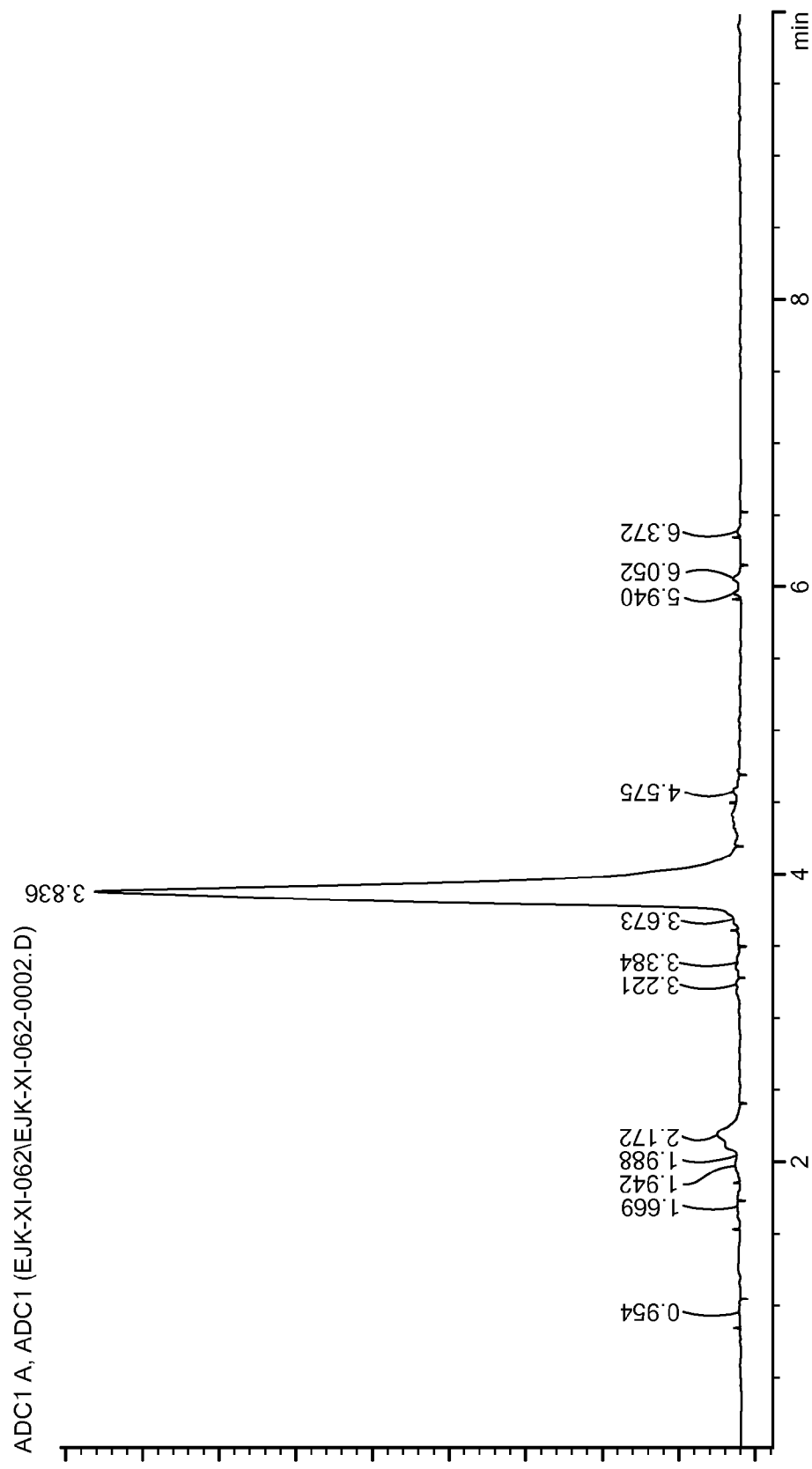
FIG. 17 shows an HPLC trace indicating the purity of propargyl tetraethylene glycolated material using a different solvent system than in FIG. 16 or FIG. 18.
Figure 18:
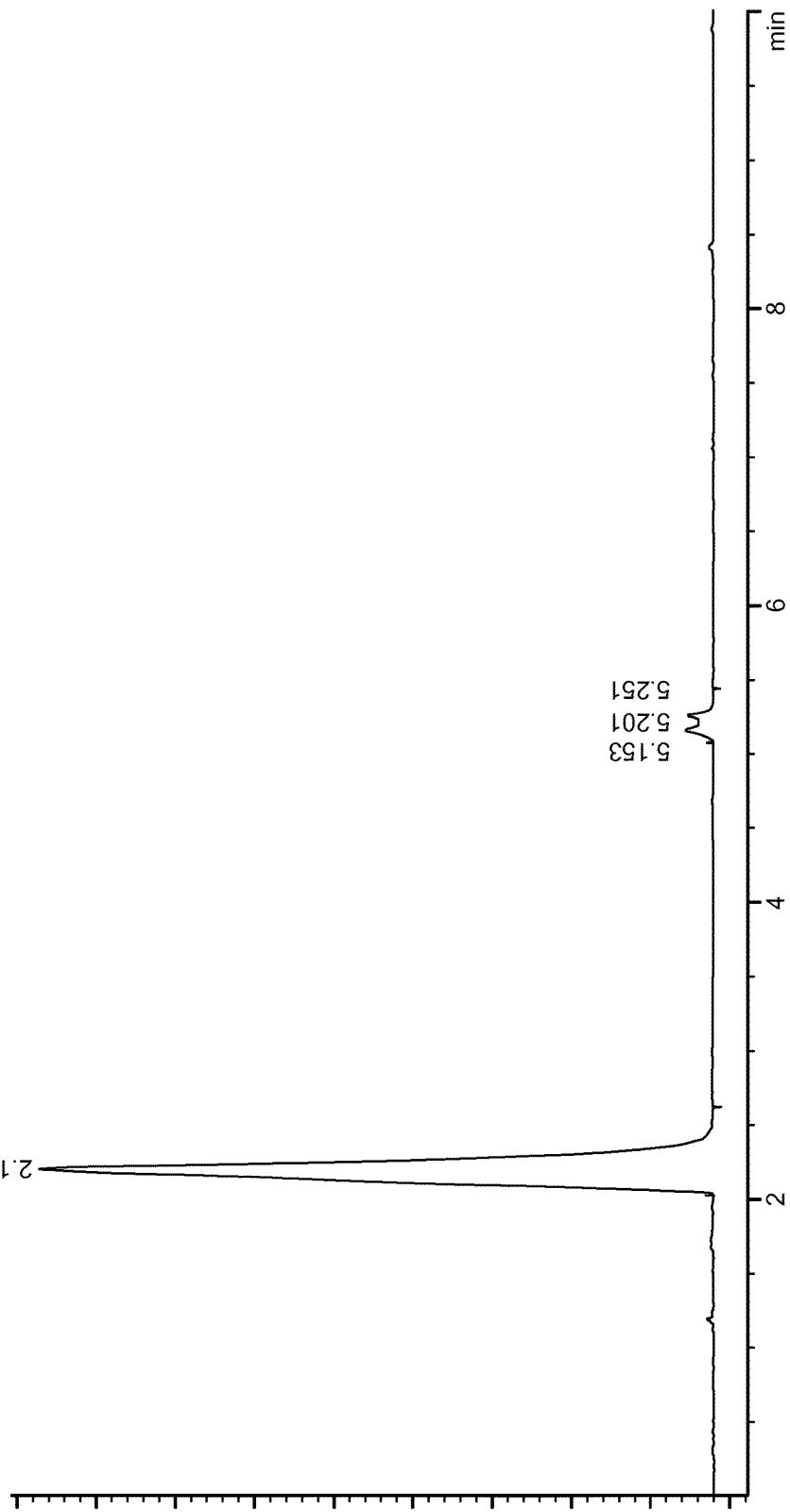
FIG. 18 shows an HPLC trace indicating the purity of propargyl tetraethylene glycolated material using a different solvent system than in FIG. 16 or FIG. 17.
Figure 19:
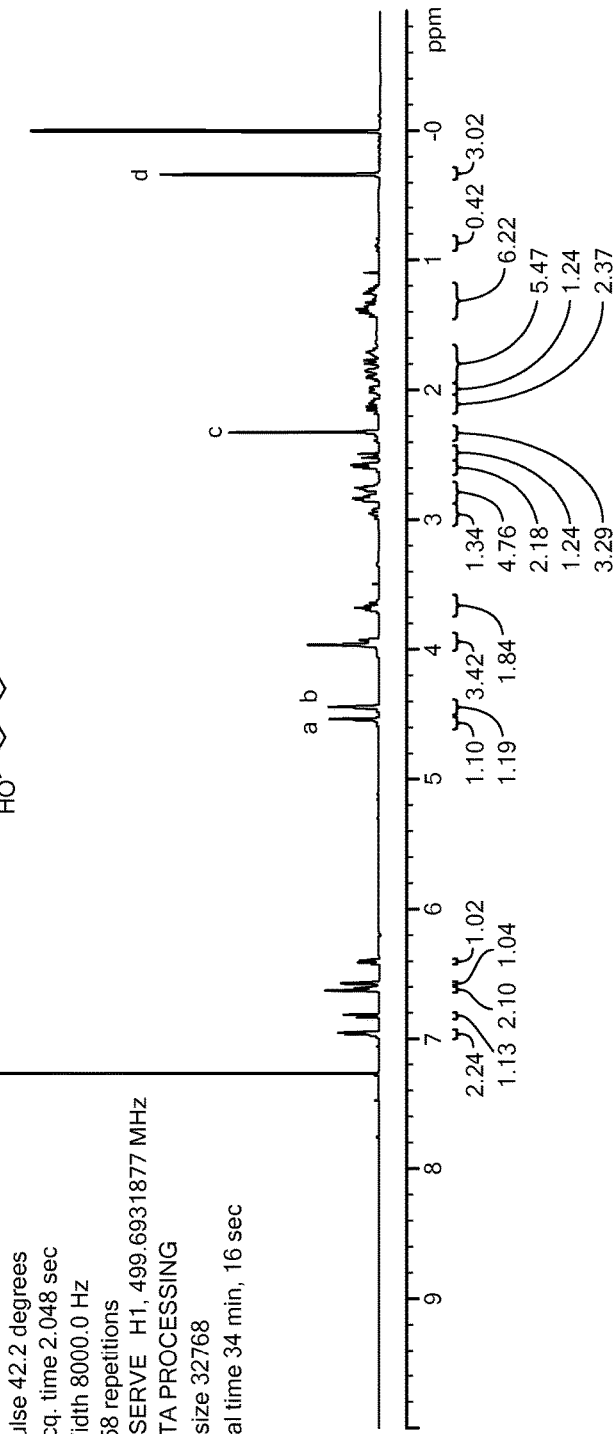
FIG. 19 is a proton NMR spectrum of the depicted N-fluoropropyl derivative.
Figure 20:
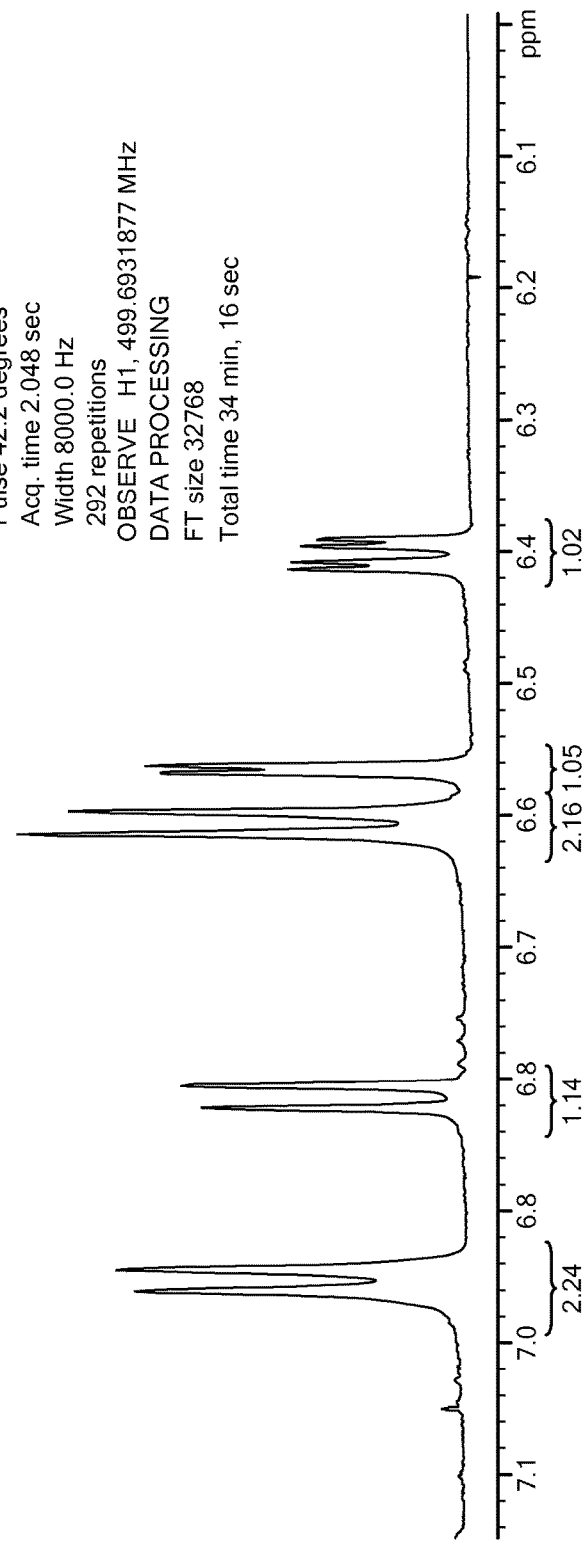
FIG. 20 shows an expanded proton NMR spectral region for the N-fluoropropyl derivative.
Figure 21:
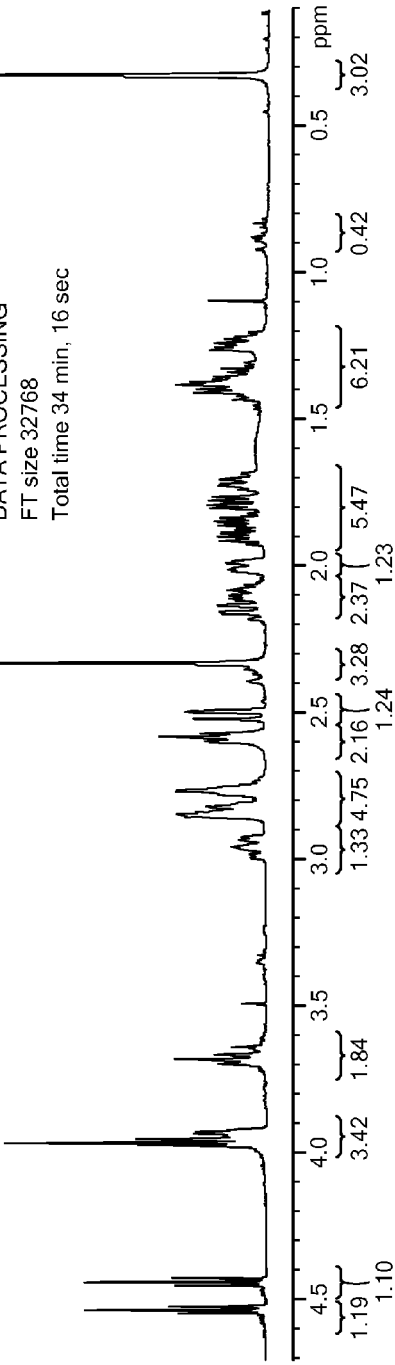
FIG. 21 is an expanded proton NMR spectral region for the N-fluoropropyl derivative.
Figure 23:
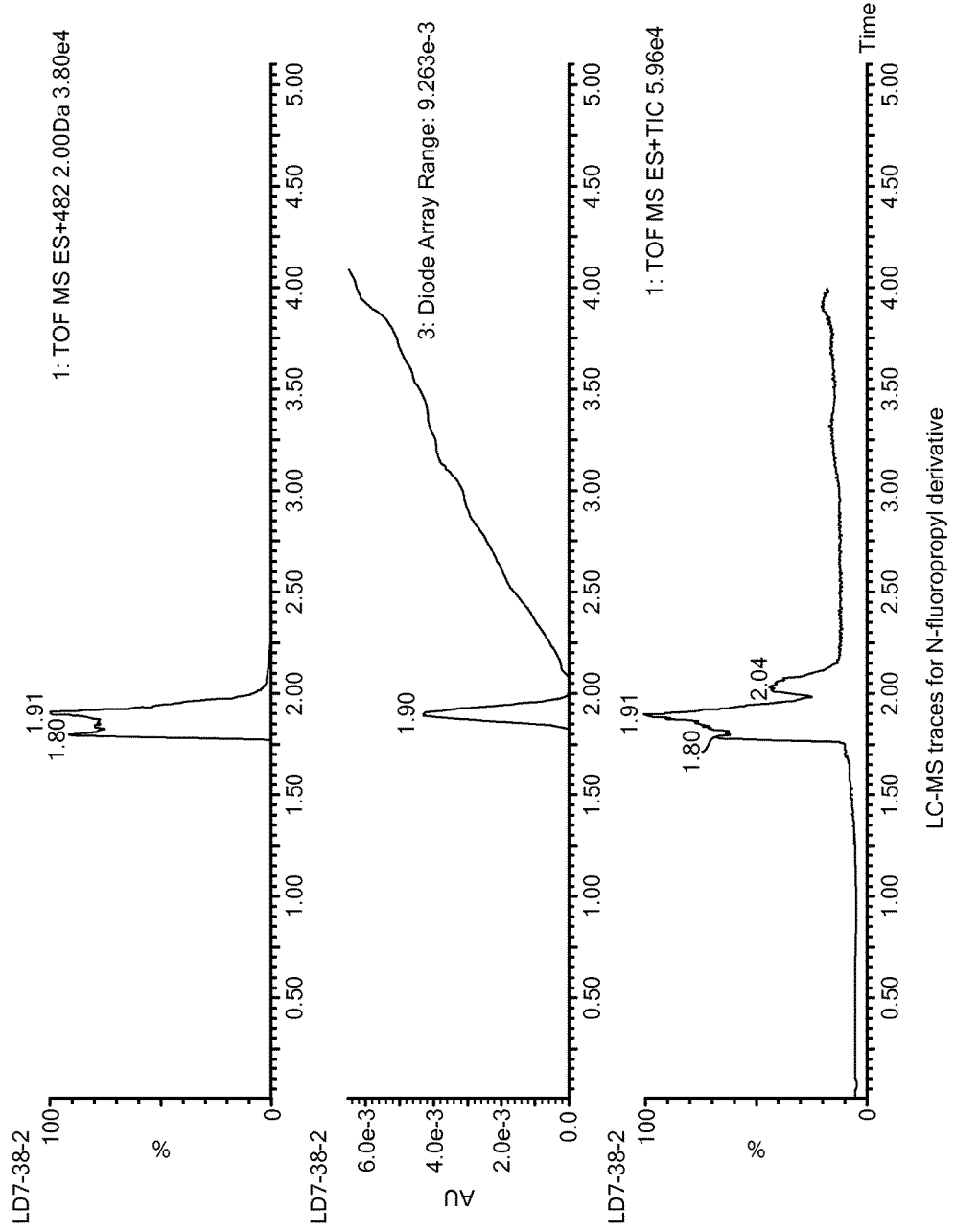
FIG. 23 shows LC-MS traces for the N-fluoropropyl derivative.
Figure 24:
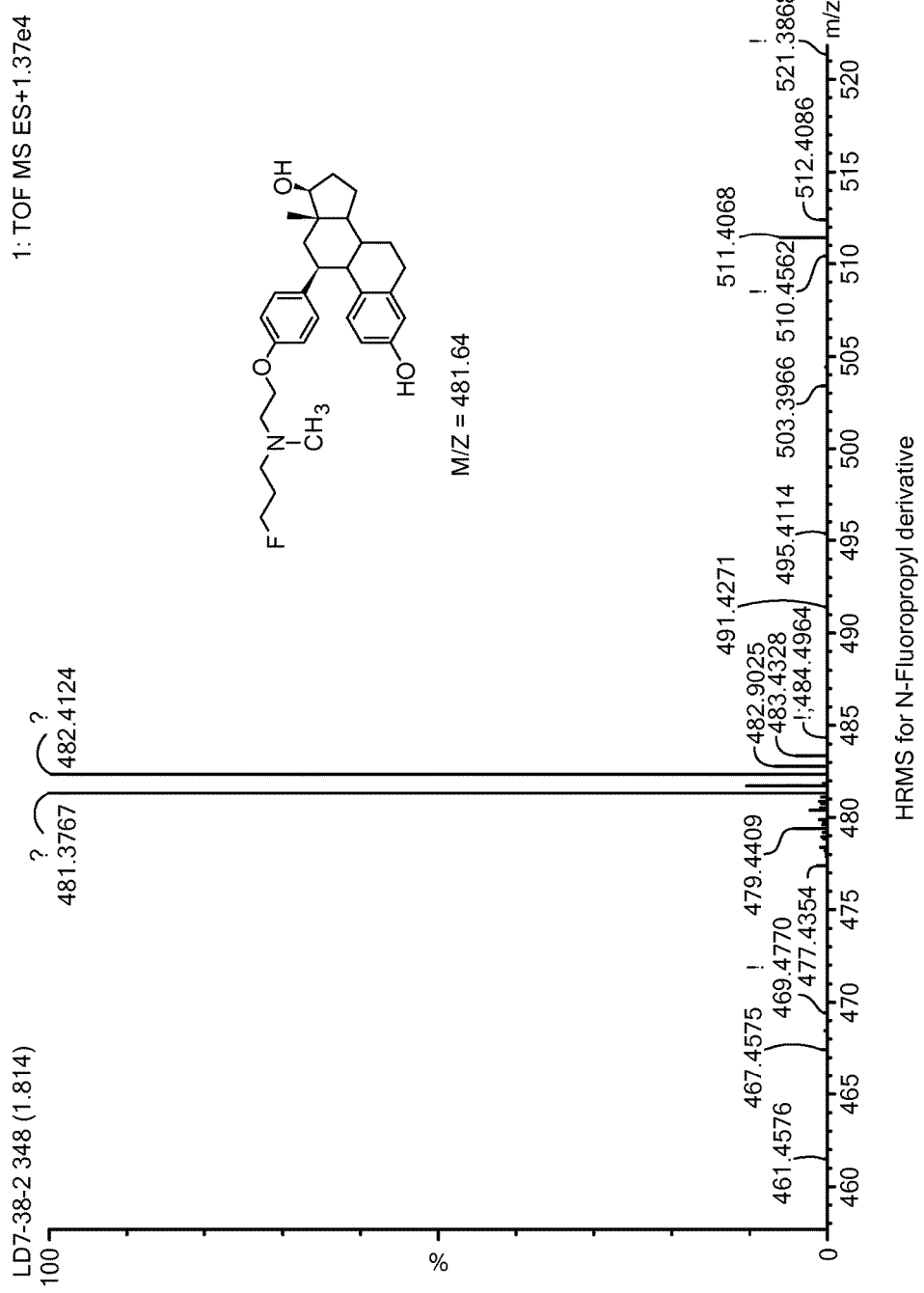
FIG. 24 shows a high resolution mass spectrum for the N-fluoropropyl derivative.
Figure 25:
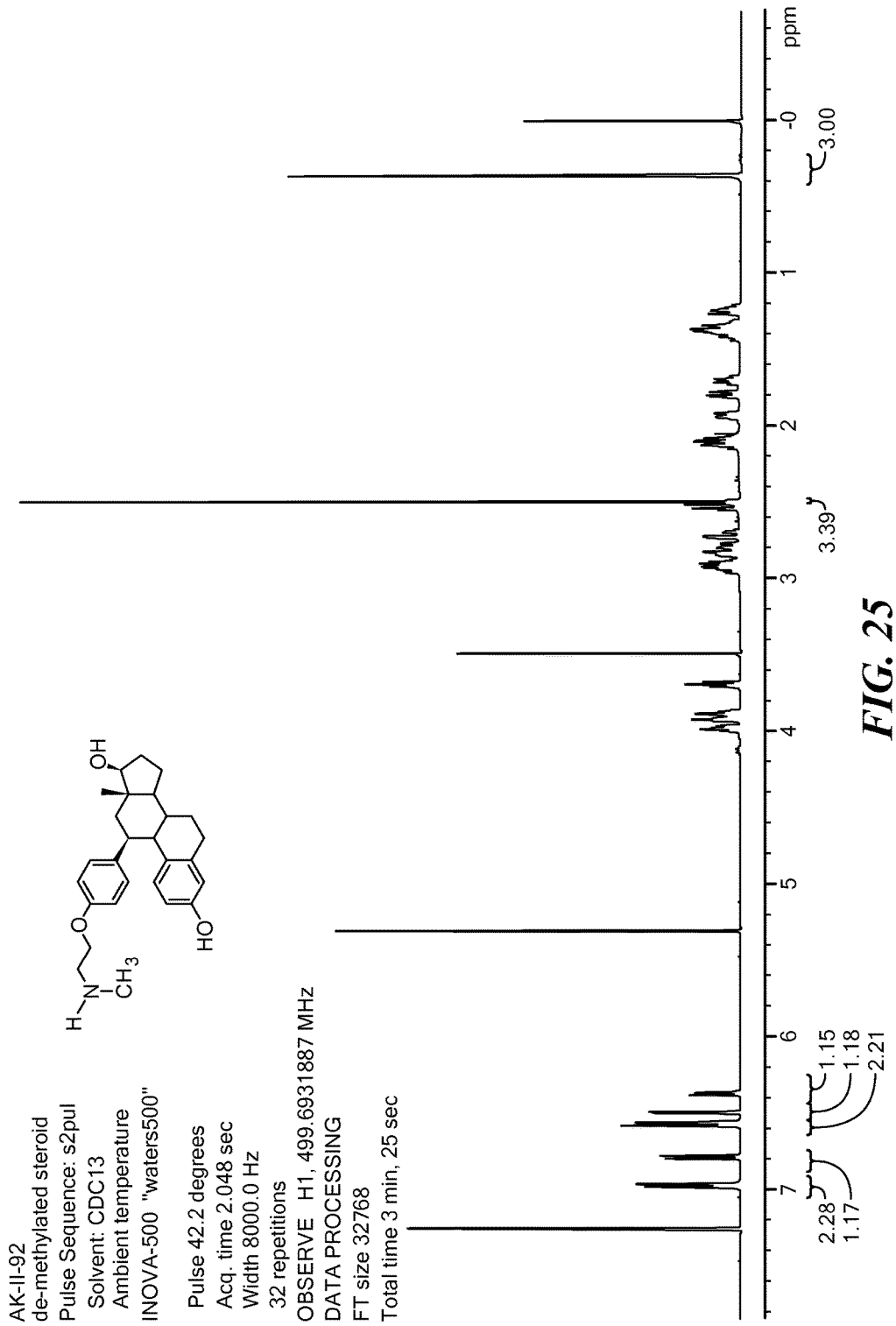
FIG. 25 is a proton NMR spectrum of the depicted N-demethylated antiestrogen.
Figure 26:
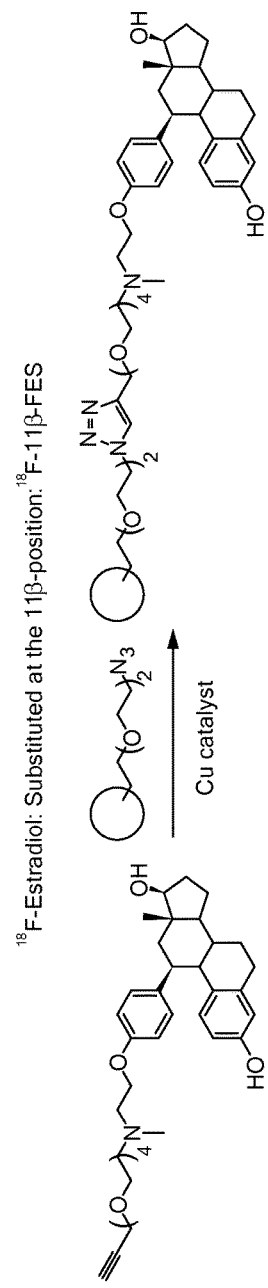
FIG. 26 is a diagram showing the variation in the conditions for synthesizing $^{18}$F-estradiol substituted at the 11β-position.
Figure 27C:
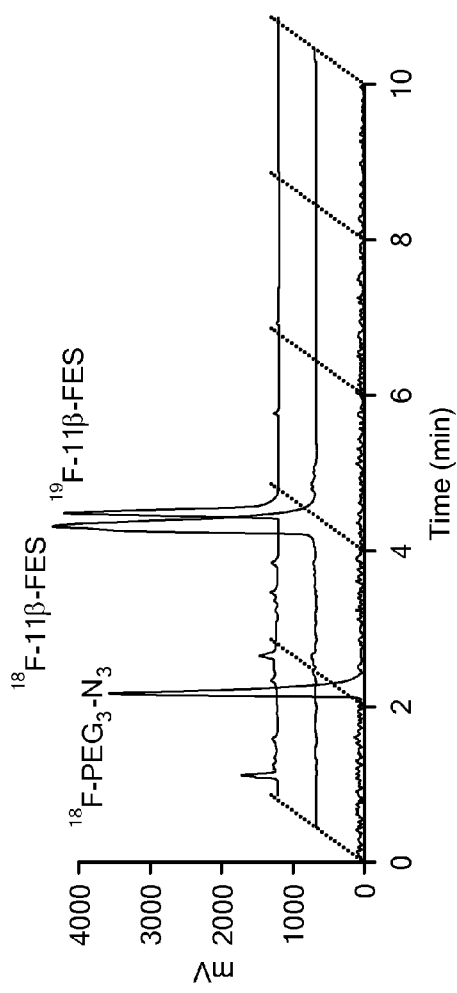
FIG. 27C is an HPLC analysis of the progress of reaction, and shows peaks corresponding to the reactant $^{18}$F-PEG$_3$-N$_3$, and the products $^{18}$F-11β-FES and $^{19}$F-11β-FES.
Figure 27D:
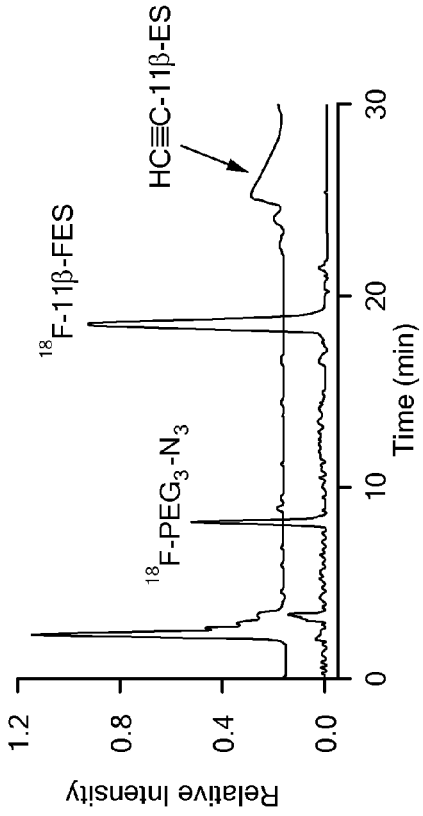
FIG. 27D shows a preparative HPLC purification of the product obtained as a result of the "click" reaction between the reactants $^{18}$F-PEG$_3$-N$_3$ and HC≡C-11β-ES, the alkynyl 11β-antiestrogen precursor. Upper trace shows UV absorption and lower trace shows radioactivity.
Figure 28:
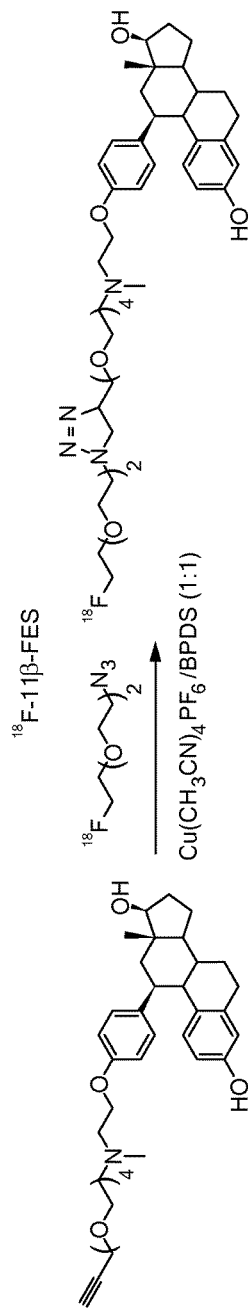
FIG. 28 shows optimization of conditions of the "click" reaction for the synthesis of $^{18}$F radiolabeled 11β antiestrogen using the reactants $^{18}$F-PEG$_3$-N$_3$ and the alkynyl and 11β-antiestrogen precursor of FIG. 2.

In addition to the $^{18}$F oligoethylene glycol azide (12) used to prepare the ER-targeted radioimaging probe $^{18}$F 11β-AE (FIG. 5), a series of reagents that can be used for other imaging modalities (FIG. 8), were coupled ("clicked") to the 11β-AE intermediate described herein (9a) or to other targeting groups. For example, a convergent approach of making a prosthetic metallated $^{99m}$Tc/Re chelate that can be directly clicked on the alkynyl (9a) or the azido (9b) 11-β substituted estradiol (FIG. 2) is described (FIG. 8). The synthesis of the final click product depends on optimal conditions, especially the Cu(I) catalyst ligands and solubility of the reagents in the reaction solvents. The Re(CO)$_3$-11βAE was synthesized and characterized.

It is important to note that the "click" chemistry depicted in FIG. 8 is entirely reversible. That is, any of the labeling moieties depicted can terminate in either an azido group and be reacted with a non-labeled 11β-AE precursor terminating in an alkynyl group, or any of the labeling moieties can terminate in an alkynyl group and be reacted with a non-labeled 11β-AE precursor terminating in an azido group. The invention contemplates each such possible combination, and the corresponding methods of synthesizing an ER imaging agent using each and every such combination.

11β-aryl estradiol-based antiestrogens labeled with Raman active moieties as MI agents are also described herein. Surface-enhanced Raman scattering (SERS) spectroscopy in combination with optical microscopy yields a novel noninvasive and label-free method to assess and image cellular processes based on their biochemical changes (Yigit, M. V. et al., 2011; Qian, X. et al., 2008). The advantage of using Raman spectroscopy over conventional optical imaging method is that it affords minimal sample preparation, high sensitivity to small intracellular fluctuations, as well as high spatial resolution. Raman spectra from within the cell reflect the biochemical composition found within the laser focal volume of approximately 0.3-1.3 m$^3$ in size, which is determined by the diffraction limit of the applied laser light. Using the spectral parameters of a cell's components, it is possible to image cellular organelles such as the nucleus, chromatin, mitochondria, and lipid bodies at the resolution of conventional microscopy without the use of external labels or dyes (Yigit, M. V. et al., 2011; Chernenko, T. et al., 2009; Kneipp, J. et al., 2009).

In general, the technique is based on identification of molecular vibrations that are characteristic of distinct functional group in a molecule. The functional groups used as the Raman active moiety for coupling to 11β-aryl substituted estradiol herein are deteuruated triphenyphosphine (dTPP) and cyano benzyl derivatives (FIG. 8). Vibrational spectra are obtained by illuminating the specimen either with infrared radiation or laser light in the visible range of the spectrum. This method of obtaining vibrational spectra is based upon the inelastic scattering of photons and is known as the Raman effects (Alhasan, M. K. et al., 2012; Pysz, M. A. et al., 2010; Chernenko, T. et al., 2009). The dTPP and azido cyano benzyl labels (FIG. 8) were coupled to the alkynyl and azido 11β-substituted estradiol described herein (FIG. 2) using click conditions to form in vitro Raman imaging probes for ER hormone dependent breast cancer cells. The probes were characterized and results obtained indicate that the Raman labels are nontoxic, stable, do not suffer from photobleaching, and possess a distinctive and specific Raman signature at near 2100 cm$^{-1}$. In the local optical field of the labels SERS also provides sensitive information about the immediate molecular environment of the label, e.g. dTPP in the cell, thereby allowing imaging the native cellular constituents and organelles.

Described herein also is an exemplary traditional fluorescent probe, fluorescein isothiocyanate (FITC), modified with complementary oligo ethoxy glycol (OEG) linker (FIG. 8), which is subsequently attached to 11βAE (9a FIG. 2) to form a fluorescent probe for ER imaging. Such probe is useful in the measurement of cellular binding uptake and/or cellular internalization of the designed ligands by ER.

EXAMPLES

Example 1. Modification of Steroid precursor—(11R,13S)-11-(4-(2-(dimethylamino)ethoxy)phenyl)-13-methyl-7,8,11,12,13,14,15,16-octahydro-1H-cyclopenta[a]phenanthrene-3,17(2H,6H)-dione (intermediate 4; FIG. 2)

Synthesis of 2-(4-bromophenoxy)-N,N-dimethylethanamine

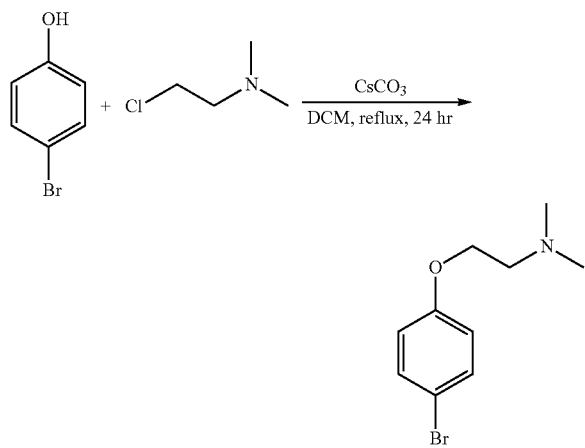

To a solution of 4-bromophenol (6.8 g, 40 mmol) in DCM (150 mL) CsCO$_3$ (19.5 g, 100 mmol) was added, and mixture was allowed to stir at room temperature for about 1 hour. Next, 2-dimethylaminoethyl chloride hydrochloride (5.6 g, 40 mmol) was added to the mixture. The reaction was stirred at reflux for approximately 24 hours. The mixture was then filtered and the filtrate was concentrated to yield a clear oily crude material. The crude material was purified using silica gel chromatography (100% DCM then 1-10% MeOH in DCM) to obtain pure 2-(4-bromophenoxy)-N,N-dimethylethanamine (4 g, 16 mmol, 42% yield). $^1$H NMR (500 MHz, CHLOROFORM-d) δ 7.33 (d, J=8.79 Hz, 2H), 6.78 (d, J=8.79 Hz, 2H), 3.99 (t, J=5.37 Hz, 2H), 2.64-2.88 (m, 2H), 2.31 (br. s., 6H). $^{13}$C NMR (100 MHz, CHLOROFORM-d) δ 158.1, 132.3, 116.6, 66.4, 58.3, 46.1.

Synthesis of (4-(2-(dimethylamino)ethoxy)phenyl)magnesium bromide

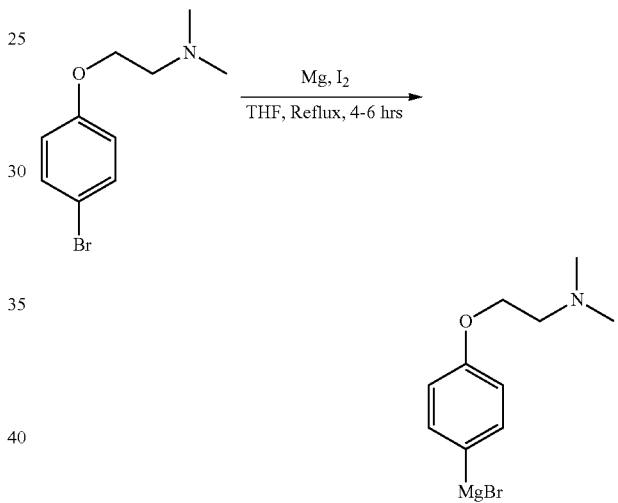

Glassware for the synthesis was rinsed with DCM and acetone, and dried in an oven overnight at 113° C. The apparatus for the reaction was assembled and flame dried with a propane torch. Magnesium turnings (3 g, 125 mmol) were placed into a three-necked flask and kept overnight in an oven heated to 113° C. After it was cooled, the apparatus was placed under argon atmosphere. Distilled anhydrous THF (50 mL) was then added to the three-necked flask followed by the addition of a small granule of iodine which immediately turned the color of the contents of the flask to orange. The mixture was allowed to stir for roughly 12 minutes followed by the addition of 2-(4-bromophenoxy)-N,N-dimethylethanamine (1 ml dissolved in 30 mL of THF) in 5 mL aliquots every 20 minutes until half of the 2-(4-bromophenoxy)-N,N-dimethylethanamine (4 g, 16 mmol) was added to the mixture. The mixture was heated to about 65° C. Next, the remainder of the 2-(4-bromophenoxy)-N,N-dimethylethanamine was added in 0.5 mL aliquots every 20 minutes. As a result, the contents first became greenish yellow, and then went to lighter yellow and finally became greenish smoky grey. The reaction mixture was heated for another hour and then cooled to room temperature.

Synthesis of (11R,13S)-11-(4-(2-(dimethylamino)ethoxy)phenyl)-13-methyl-7,8,11,12,13,14,15,16-octahydro-1H-cyclopenta[a]phenanthrene-3,17(2H,6H)-dione

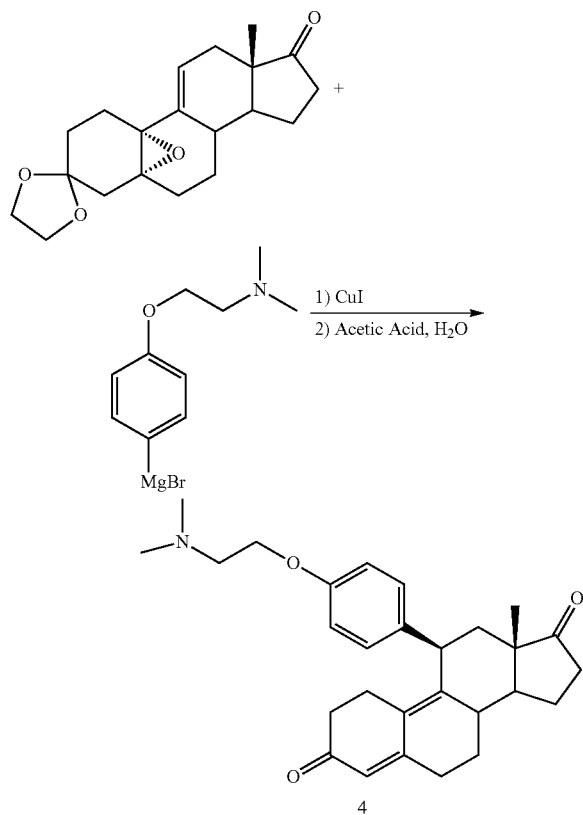

3,3-Ethylenedioxy-5(10)-α-epoxy-estr-9-ene-17-one (2.014 g, 6.1 mmol) was dissolved in anhydrous THF (15 mL) under argon. Copper (I) iodide (0.160 g, 0.840 mmol) was added to the solution at −10° C. and stirred for 15 min Freshly prepared Grignard reagent, (4-(2-(dimethylamino) ethoxy)phenyl)magnesium bromide, was added dropwise in 5.0 mL aliquots. The reaction was gradually warmed to ambient temperature and stirring was continued for 16 hours. The reaction was quenched by the addition of ammonium chloride (0.8 g, 15 mmol) in 35 mL of water and 35 mL of EtOAc at 10° C. The organic layer was washed with water (2×35 mL). The organic solvent was removed under reduced pressure and the resulting residue was dissolved in a mixture of acetic acid (14 mL) and water (6 mL). The resultant mixture was warmed at 50-60° C. for 1.5 hours, after which it was diluted with ethyl acetate (20 mL). The solution was neutralized by the addition of saturated aqueous sodium bicarbonate. The organic layer was separated, washed with brine solution, dried over magnesium sulfate and evaporated to dryness to give a crude, yellow oil. Purification using silica gel column chromatography (70:30 hexane/ethyl acetate) afforded the desired product (2.00 g, 76%) as yellow solid: $^1$H NMR (CDCl$_3$, 400 MHz): δ 0.53 (3H, s), 4.38 (1H, d, J=6.9), 5.78 (1H, s), 6.71 (2H, d), 6.97 (2H, d). $^{13}$C NMR (CDCl$_3$, 100 MHz): δ 14.17, 21.76, 25.99, 27.06, 30.68, 35.02, 36.87, 38.14, 38.34, 39.71, 47.53, 50.77, 115.53, 122.82, 128.30, 129.83, 135.52, 145.62, 155.59, 155.99, 197.54, 217.44; m.p. 248° C.

Example 2. Pharmacokinetics and Biodistribution Analysis of $^{18}$F-11β-FES

Figures 29A, 29B:
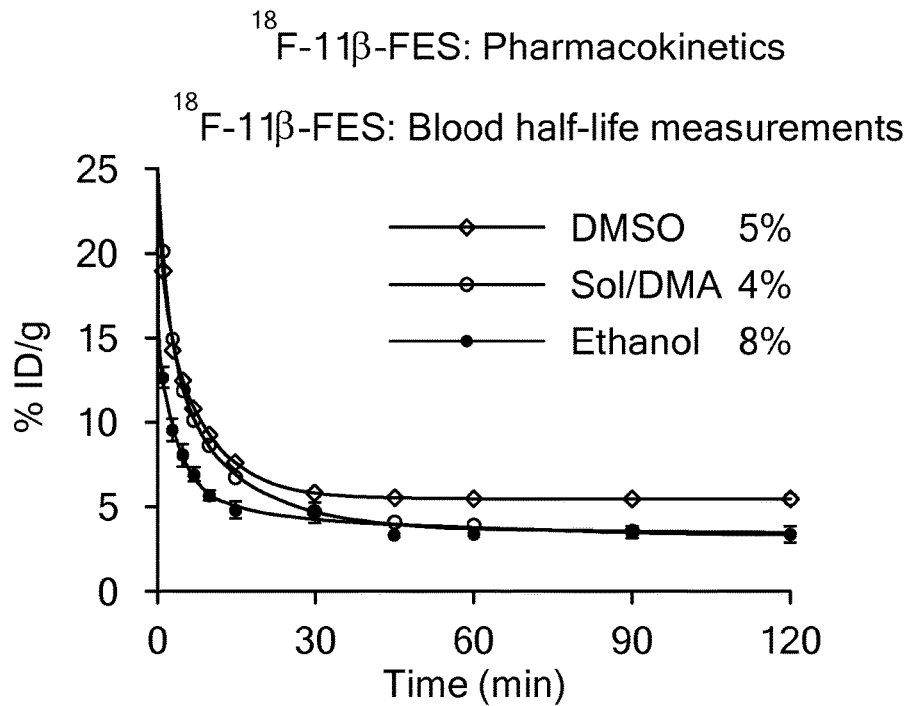
FIG. 29A is a graph of the pharmacokinetics of $^{18}$F radiolabeled 11β antiestrogen ($^{18}$F-11β-FES) showing half-life measurements of the compound in the blood.
FIG. 29B is a table of different formulations used in the pharmacokinetics measurements shown in FIG. 29A.
Figure 29D:
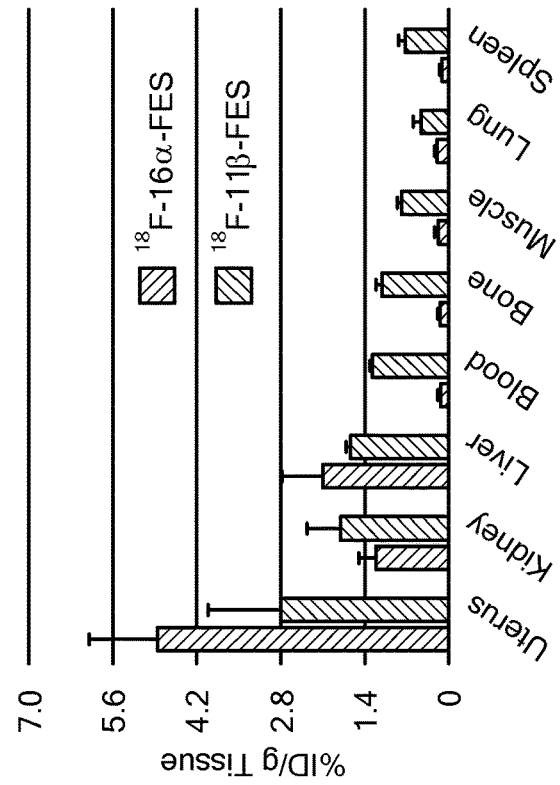
FIG. 29D is a comparison of the biodistribution of $^{18}$F-16α-FES (left bar of each pair, Kiesewetter (1984)) and $^{18}$F-11β-FES of the present invention (right bar of each pair).
Figure 29C:
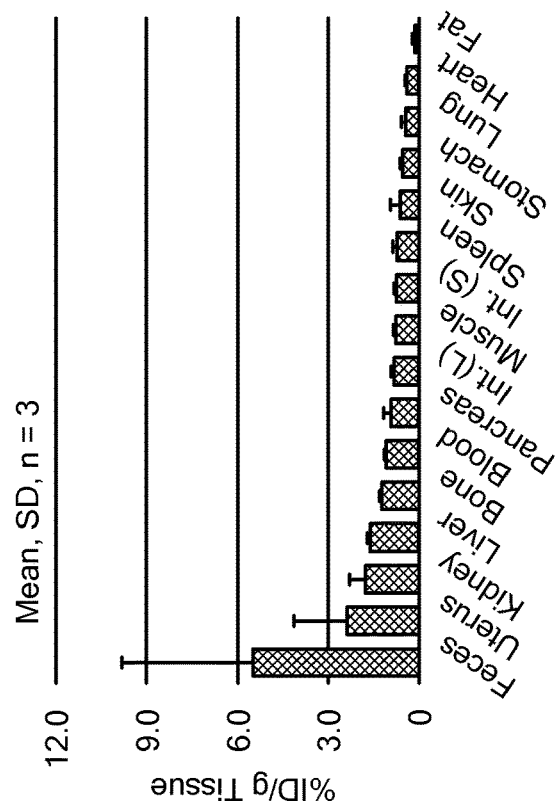
FIG. 29C is a graph of the biodistribution of $^{18}$F-11β-FES.

Pharmacokinetics measurements were carried out after administration of $^{18}$F-11β-FES to C57 BL/6 mice (FIGS. 29 A and B). A number of co-solvents, dimethyl sulfoxide (DMSO, 5%), 4% 1:1 Solutol:dimethyl acetamide (DMA), and ethanol (8%) were tested. A 36% reduction in terminal concentration of $^{18}$F-11β-FES was found when ethanol was used as a co-solvent. Biodistribution measurements showed that other than kidney, liver, blood and feces, which are associated with excretion, the highest concentration of $^{18}$F-11β-FES was found in the uterus (an ER expressing organ) (FIG. 29C). A comparison of the biodistribution of $^{18}$F-11β-FES and $^{18}$F-16α-FES (Kiesewetter, J. Nucl. Med., 1984, vol. 25, 1212) is shown in FIG. 29 D.

Figures 30A, 30B:
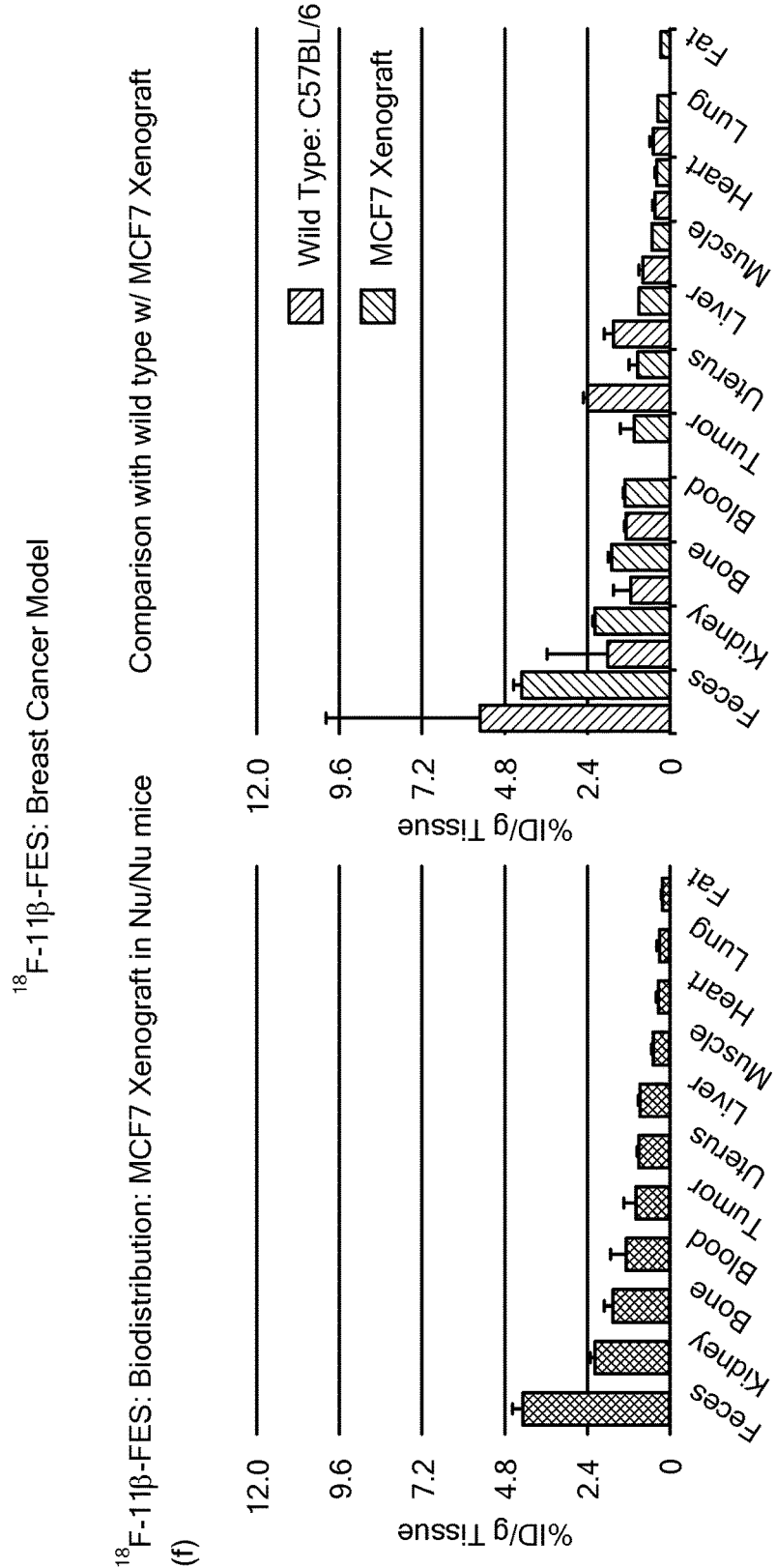
FIG. 30A is a graph of the biodistribution of $^{18}$F-11β-FES in a breast cancer model of a xenograft of MCF7 cells in nu/nu mice.
FIG. 30B is a graph of comparison of the biodistribution of $^{18}$F-11β-FES in wild type mice (left bar of each pair) and mice having the MCF7 xenograft (right bar of each pair).

Example 3. Biodistribution of $^{18}$F-11β-FES in an Animal Model of Breast Cancer Biodistribution of $^{18}$F-11β-FES was also measured in Nu/Nu mice implanted with a xenograft of MCF7 breast cancer cells. ER expressing tumors and uterus were each observed to accumulate substantial amounts of $^{18}$F-11β-FES, which was higher than in any other tissue/material not associated with excretion, with the exception of bone (FIGS. 30 A and C). Similar results were obtained when the biodistribution of $^{18}$F-11β-FES in the tissues of Nu/Nu mice implanted with breast cancer xenograft was compared with that in the tissues of wild type C57BL/6 mice (FIGS. 30 B and C).

Example 4. PET Scan of $^{18}$F-11β-FES in C57BL/6 Mouse

Figure 31:
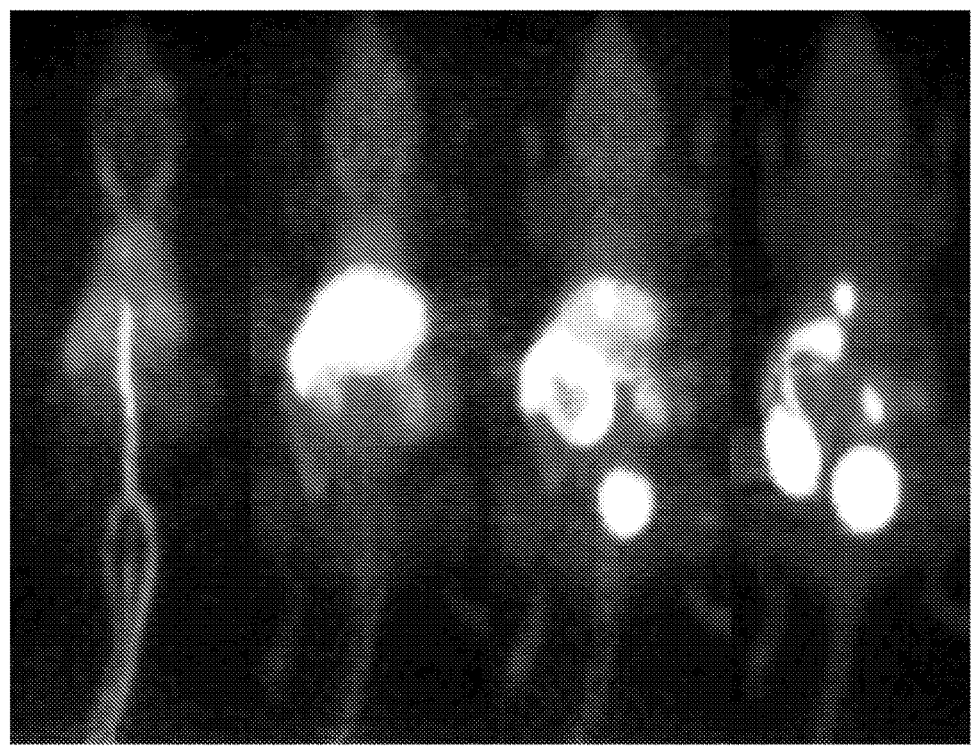
FIG. 31 is an image of a 2 hour dynamic PET scan of a C57B1/6 mouse administered with $^{18}$F-11β-FES. The image shows that within 3 minutes post injection the majority of activity is in the liver ($2^{nd}$ image from left), from which it quickly moves to the intestines ($3^{rd}$ image from left). At approximately 15 minutes post injection (far right image), a significant amount of activity has accumulated in the bladder.

A PET scan was carried out on a C57BL/6 mouse administered with $^{18}$F-11β-FES. A 2 hour dynamic PET scan of the mouse is shown in FIG. 31. Within 3 minutes post injection the majority of activity was found to be localized in the liver (second panel from the left), form which the label was observed to quickly localize to the intestines (third panel from the left). A significant amount of activity was observed to accumulate in the bladder approximately 15 minutes post injection (right panel).

Example 5. F-11β-AE with Optimized N-Linker

An ER-specific MI compound should have high uptake and retention within target tissues (e.g., uterus and tumor), lower concentration in blood and nontarget tissue, and increased renal clearance. The single factor most likely to influence those parameters is the basicity/hydrophobicity of the nitrogen. Unlabeled N-modified F-11-β intermediates shown below (right) are candidate molecules that have modification of the linker to yield reduced values of c Log P.

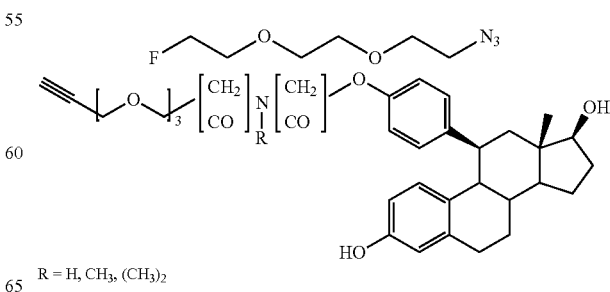

R = H, CH$_3$, (CH$_3$)$_2$

Substitution on the N-group includes secondary to quaternary and carbonyl groups on either side (amide). Synthesis of these unlabeled F-11β-AE derivatives is illustrated below.

Subsequent ligation to fluorotriethylene glycol azide provides the final compounds as the unlabeled derivatives. The final compounds are all more hydrophilic than the F-11β-AE described herein by 0.5-2.5 log units. Analysis of the bind-

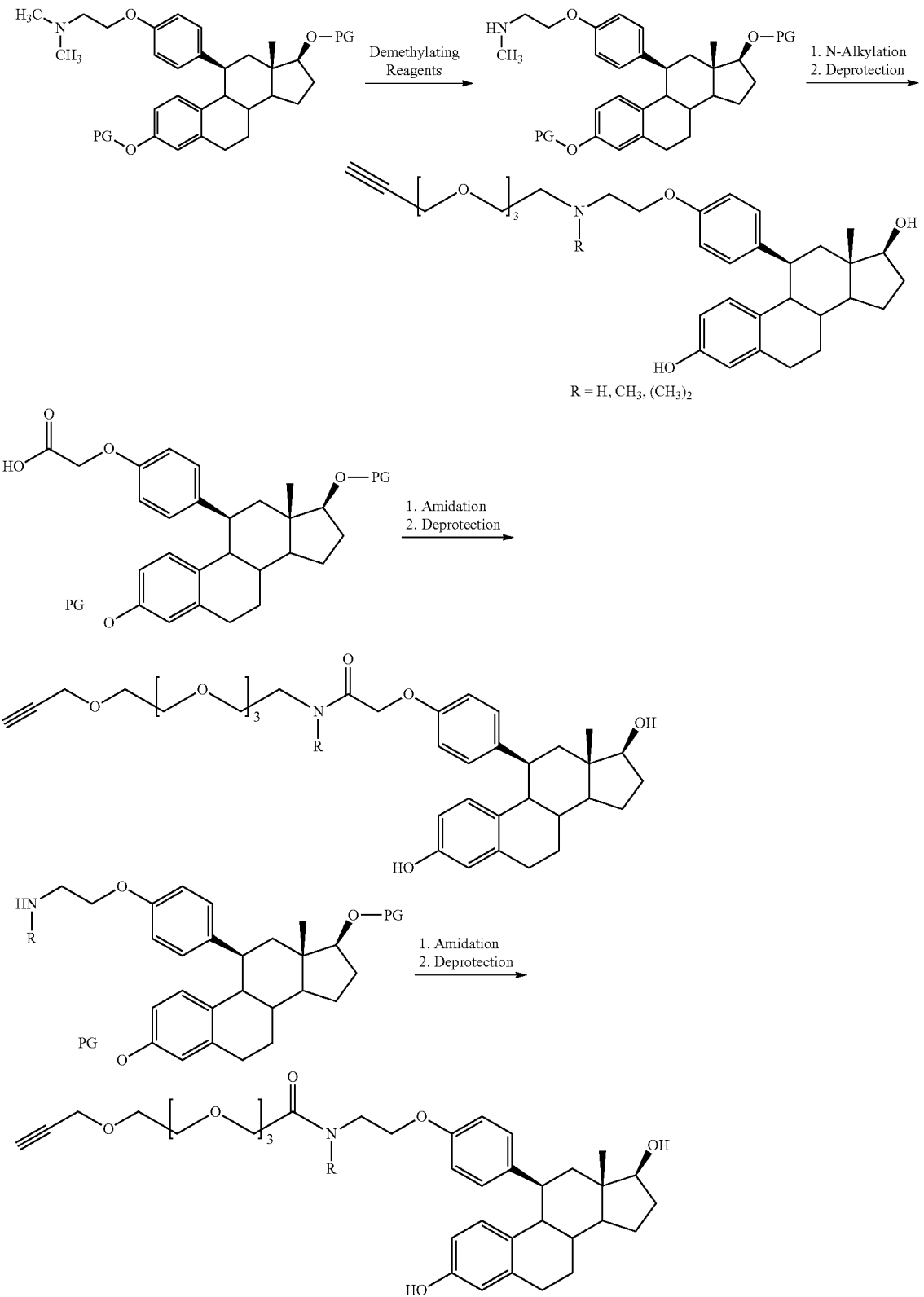

R = H, CH₃, (CH₃)₂ ing, cell penetration and metabolic properties is carried out to indicate the influence various substituents on the nitrogen has on biological properties. Based upon the results, one or more compounds are selected for evaluation as their [$^{18}$F]-analogs.

The relative binding affinity (RBA) of the compounds is determined using a competitive binding assay with the full-length recombinant ER-α and ER-β from PanVera (Madison, Wis.). Because many breast cancer cells express both subtypes, the binding affinity of the alkynyl precursor and final F-11β-AE is determined for both subtypes. F-11β-AE described herein and E2 are used as controls.

Efficacy studies for the synthesized F-11β-AE compounds are performed using a cell-based inhibition ERα transactivation assay. The assay uses heLA, HepG and MCF-7 cells transfected with plasmids encoding ER (or empty vector) using lipofectamine-2000 (Invitrogen). The cells are treated with increasing concentrations of the compounds or controls, followed by harvesting at 20-24 h. Evaluation for luciferase activity using the Luciferase Assay Kit (Promega) provides data from which the efficacy ($IC_{50}$) is determined Compounds having c Log P values in the 1.5-4.5 range are selected for labeling and use as imaging agents.

In vitro metabolic evaluation of representative 18F-11β-AE is performed as follows. In vitro metabolism measurements utilizes the rat hepatocyte culture, as previously described (Jonson et al., 1999). Rodents do not have steroid hormone binding globulin (SHBG) or Human serum albumin (HAS) and conditions are adjusted to account for this. The compounds of interest are labeled using click chemistry (FIG. 2) and added (100 µL, 1.0 mCi) to the cells (3.9 mL). After a brief swirling to initiate the process, an aliquot (0.1 mL) is removed, transferred to a 0.5 mL centrifuge tube containing ethanol (0.1 mL). The T0 sample is vortexed, sonicated, and centrifuged to separate supernatant from the cell pellet. Additional aliquots are removed and processed in a similar fashion at predetermined time intervals. The supernatant (20 µL) is spotted on TLC plates and developed with an appropriate solvent system. Air dried plates are scanned using an automated radio-TLC scanner and the metabolites/parent compound radiotracer peaks are integrated to determine metabolic disposition. The effect of SHBG on metabolism is determined by repeating the previous experiments but adding human SHBG (80 µg, 1 mg/mL in buffer) to the isolated hepatocytes prior to the addition of the 18F-11β-AE derivative. The control is the hepatocyte culture with just addition of the buffer solution. The effects of HSA, for which the antiestrogen may have affinity, are examined similarly.

The in vivo biostribution, pharmacokinetic and metabolic stability measurements of the [18F]-F-11β-AE synthesized in this Example are performed as follows. The labeled compounds are evaluated initially in normal female mice to determine uterine uptake (% ID/g) and selectivity (T/NT). Imaging also provides data regarding non-target disposition and major clearance (hepatic vs renal) pathways. Each compound is compared to $^{18}$F-FES. Uptake of high doses of estradiol demonstrates specific ER binding in target tissues. Based upon the preliminary studies, the compounds with the best uterine uptake values, highest selectivity (uterus to nontarget tissue) and clearance pathway (renal>hepatic) compared to FES is evaluated in implanted breast tumor models. Tissue distribution, selectivity and clearance are determined Procedures for both normal and tumor bearing animal studies are well established. The results are analyzed to evaluate the effect of RBA, c Log P, and other effects of the substituents on each of the biological parameters associated with effective imaging. The compound(s) with the best properties are evaluated more extensively for their in vivo metabolism.

Metabolism in vivo of the [18F]-F-11β-AE is evaluated using normal female rats. Groups of rats are sacrificed at 30, 60 and 120 minutes post administration of the radiotracer. Blood is separated to give protein bound and free components and each is evaluated by radio-TLC to determine the number and type of radiolabeled species. Liver and bladder are examined to determine the number and type of labeled compounds present in both at each time point. The values are compared to results found with FES. In rats, FES is rapidly metabolized to more polar species. By 60 minutes after injection, less than 15% of circulating radioactivity is due to [18F]-FES; the remainder is metabolites. It has been reported that injection of blood from rats obtained 2 hours after injection into different rats showed that the metabolites did not accumulate in ER-rich tissues (Mathias, C. J. et al., 1987). The extent to which the 11β-substituent modifies the metabolism of the radiotracer is determined. The structural modifications is expected to lead to an uptake in the target tissue, comparable to FES (FIG. 4). Reduction of the c Log P values is expected to reduce hepatic uptake and clearance with faster elimination via renal excretion. This produces lower blood levels and less colonic background. Faster blood clearance lowers retention in nontarget tissues, resulting in improved T/NT values. Reduced in vivo metabolism also leads to better pharmacokinetic properties.

REFERENCES

Alhasan, M. K.; Liu, L.; Lewis, M. A.; Magnusson, J.; Mason, R. P.: Comparison of optical and Power Doppler ultrasound imaging for non-invasive evaluation of arsenic trioxide as a vascular disrupting agent in tumors. *PLoS One* 2012, 7, e46106.

Allred, D. C.; Carlson, R. W.; Berry, D. A.; Burstein, H. J.; Edge, S. B.; Goldstein, L. J.; Gown, A.; Hammond, M. E.; Iglehart, J. D.; Moench, S.; Pierce, L. J.; Ravdin, P.; Schnitt, S.

J.; Wolff, A. C. NCCN task force report: estrogen receptor and progesterone receptor testing in breast cancer by immunohistochemistry. *J Natl Comp Cancer Net,* 2009, 7(Suppl. 6), S1-S21.

Antoch, G.; Bockisch, A.: Combined PET/MRI: a new dimension in whole-body oncology imaging? *European Journal of Nuclear Medicine and Molecular Imaging* 2009, 36, 113-120.

Benard, F.; Turcotte, E.: Imaging in breast cancer: Single-photon computed tomography and positron-emission tomography. *Breast Cancer Res.* 2005, 7, 153-162.

Bennink, R. J.; Rijks, L. J.; van, T. G.; Noorduyn, L. A.; Janssen, A. G.; Sloof, G. W.: Estrogen receptor status in primary breast cancer: Iodine 123-labeled cis-11β-methoxy-17α-iodovinyl estradiol scintigraphy. *Radiology* (Oak Brook, Ill., U.S.) 2001, 220, 774-779.

Beyer, T.; Pichler, B.: A decade of combined imaging: from a PET attached to a CT to a PET inside an MR. *European Journal of Nuclear Medicine and Molecular Imaging* 2009, 36, 1-2.

Buck, A. K.; Gaertner, F.; Beer, A.; Hermann, K.; Ziegler, S.; Schwaiger, M.: *Preclinical and clinical tumor imaging with SPECT/CT and PET/CT*. Wiley-VCH Verlag GmbH & Co. KGaA, 2012; Vol. 1; pp 247-288.

Cummins, C. H.: Radiolabeled steroidal estrogens in cancer research. *Steroids* 1993, 58, 245-59.

Czernin J.; Benz M. R; Allen-Auerbach M. S. PET/CT imaging: The incremental value of assessing the glucose metabolic phenotype and the structure of cancers in a single examination. *Eur J Radiol,* 2010, 73, 470-480.

Dao, K.-L.; Sawant, R. R.; Hendricks, J. A.; Ronga, V.; Torchilin, V. P.; Hanson, R. N.: Design, Synthesis, and Initial Biological Evaluation of a Steroidal Anti-Estrogen-Doxorubicin Bioconjugate for Targeting Estrogen Receptor-Positive Breast Cancer Cells. *Bioconjugate Chem.* 2012, 23, 785-795.

Dehdashti, F.; Mortimer, J. E.; Trinkaus, K.; Naughton, M. J.; Ellis, M.; Katzenellenbogen, J. A.; Welch, M. J.; Siegel, B. A. PET-based estradiol challenge as a predictive biomarker of response to endocrine therapy in women with estrogen-receptor-positive breast cancer, *Breast Cancer Res Treat,* 2009, 113, 509-517.

DeMartini W.; Lehman C.; Partridge S. Breast MRI for cancer detection and characterization: a review of evidence-based clinical applications. *Acad Radiology,* 2008, 15, 408-416.

de Vries, E. F. J.; Rots, M. G.; Hospers, G. A. P. Nuclear imaging of hormonal receptor status in breast cancer: a tool for guiding endocrine treatment and drug development. *Curr Cancer Drug Targets,* 2007, 7, 510-519.

Dittmann, H.; Jusufoska, A.; Dohmen, B. M.; Smyczek-Gargya, B.; Fersis, N.; Pritzkow, M.; Kehlbach, R.; Vonthein, R.; Machulla, H. J.; Bares, R. 3'-Deoxy-3'-[18F]fluorothymidine (FLT) uptake in breast cancer cells as a measure of proliferation after doxorubicin and docetaxel treatment, *Nucl Med Biol,* 2009, 36, 163-169.

Dunn, L; DeMichele, A. Genomic predictors of outcome and treatment response in breast cancer. *Molec Diag Ther,* 2009, 13, 73-90.

Gemignani, M. L.; Patil, S.; Seshan, V. E.; Sampsonm, M.; Humm, J L; Lewis, J. S.; Brogi, E.; Larson, S. M.; Morrow, M.; Pandit-Taskar, N. Feasibility and predictability of perioperative PET and estrogen receptor ligand in patients with invasive breast cancer, *J Nucl Med,* 2013, 54, 1697-1702.

Jonson, S. D.; Bobasera, T. A.; Dehdashti, F.; Cristel, M. E.; Katzenellenbogen, J. A.; Welch, M. J. Comparative breast tumor imaging and comparative in vitro metabolism of 16α-[18F]-fluoroestradiol and 16β-[18F]-fluoromoxestrol in isolated hepatocytes. *Nucl Med Biol,* 1999, 26, 123-130.

Hanson, R. N.: Biomedical imaging: advances in radiotracer and radiopharmaceutical chemistry. *RSC Drug Discovery Ser.* 2012, 15, 21-48.

Hanson, R. N.; Hua, E.; Adam, H. J.; Labaree, D.; Hochberg, R. B.: Synthesis and evaluation of 11β-(4-Substituted phenyl) estradiol analogs: Transition from estrogen receptor agonists to antagonists. Bioorg. Med. Chem. 2012, 20, 3768-3780.

Higa, G. M. Breast cancer: beyond the cutting edge. *Exp Op Pharmacother,* 2009, 10, 2479-2498

James, M. L.; Gambhir, S. S.: A molecular imaging primer: modalities, imaging agents, and applications. *Physiol. Rev.* 2012, 92, 897-965.

Keune J. D; Jeffe D. B; Schootman M.; Hoffman A.; Gillanders W. E; Aft R. L. Accuracy of ultrasonography and mammography in predicting pathologic response after neoadjuvant chemotherapy for breast cancer, *Amer J Surgery,* 2010, 199, 477-484.

Khalil, M. M.; Tremoleda, J. L.; Bayomy, T. B.; Gsell, W.: Molecular SPECT Imaging: An Overview. *International Journal of Molecular Imaging,* 2011, 2011.

Kiesewetter, D. O., Katzenellenbogen, J. A., Kilbourn, M. R.; Welch, M. J. Synthesis of 16-fluoroestrogens by unusually facile fluoride ion displacement reactions: prospects for the preparation of fluorine-18 labeled estrogens. *J Org Chem,* 1984, 49, 4900-4905.

Kiesewetter, DO, Kilbourn, M R, et al. Preparation of four fluorine-18-labeled estrogens and their selective uptakes in target tissues of immature rats. *J Nucl Med,* 1984, 25:1212-21.

Knott, K. E.; Graetz, D.; Huebner, S.; Juettler, S.; Zankl, C.; Mueller, M., Simplified and automatic one-pot synthesis of 16α-[18F]fluoroestradiol without high-performance liquid chromatography purification, *J Labelled Comp Radiopharm,* 2011, 54, 749-753.

Kodibagkar, V. D.; Hallac, R. R.; Zhao, D.; Yu, J.-X.; Mason, R. P.: 19F NMR: clinical and molecular imaging applications. *Mol. Med. Med. Chem.* 2012, 6, 461-524.

Koolen, B. B.; Vogel, W. V.; Vrancken, P. M. J. T. F. D.; Loo, C. E.; Rutgers, E. J. T.; Valdes, O. R. A.: Molecular imaging in breast cancer: from whole-body PET/CT to dedicated breast PET. *J. Oncol.* 2012, 438647, 8 pp.

Kumar, P.; Mercer, J.; Doerkson, C.; Tonkin, K.; McEwan, A. J. B. Clinical production, stability studies and PET imaging with 16-α-[18F] fluoroestradiol ([18F] FES) in ER positive breast cancer patients, *J Pharm Pharmaceut Sci,* 2007, 10, 256s-265s.

Kumar, P.; Mercer, J. R. Clinical manufacturing of [18F]-16-α-fluoroestradiol ([18F]FES), *Radiochemical Syntheses,* 2012, 1 (Radiopharmaceuticals for Positron Emission Tomography), 69-80.

Kurland, B. F.; Peterson, L. M.; Lee, J. H.; Linden, H. M.; Schubert, E. K.; Dunnwald, L. K.; Link, J. M.; Krohn, K. A.; Mankoff, D. A. Between-patient and within-patient (site-to-site) variability in estrogen receptor binding, measured in vivo by 18F-fluoroestradiol PET, *J Nucl Med,* 2011, 52, 1541-1549.

Lim, J. L.; Zheng, Lei; Berridge, M. S.; Tewson, T. J., The use of 3-methoxymethyl-16β,17β-epiestriol-O-cyclic sulfone as the precursor in the synthesis of F-18 16α-fluoroestradiol, *Nuclear Medicine and Biology,* 1996, 23(7), 911-915.

Linden, H. M.; Kurland, B. F.; Peterson, L. M.; Schubert, E. K.; Gralow, J. R.; Specht, J. M.; Ellis, G. K.; Lawton, T. J.; Livingston, R. t B.; Petra, P. H.; et al, Fluoroestradiol positron emission tomography reveals differences in pharmacodynamics of aromatase inhibitors, tamoxifen, and fulvestrant in patients with metastatic breast cancer, *Clin Cancer Res,* 2011, 17, 4799-4805.

Mawlawi, O.; Townsend, D.: Multimodality imaging: an update on PET/CT technology. *European Journal of Nuclear Medicine and Molecular Imaging* 2009, 36, 15-29.

Mathias, C J, Welch, M J, et al. Characterization of the uptake of 16α-([18F]fluoro)-17 beta-estradiol in DMBA-induced mammary tumors. *Int J Rad Appl Instrum* 1987, 14:15-25.

Misri, R.; Meier, D.; Yung, A. C.; Kozlowski, P.; Hafeli, U. O.: Development and evaluation of a dual-modality (MRI/SPECT) molecular imaging bioprobe. *Nanomedicine (New York, N.Y., U.S.)* 2012, 8, 1007-1016.

Morales-Avila, E.; Ferro-Flores, G.; Ocampo-Garcia, B. E.; De, L.-R. L. M.; Santos-Cuevas, C. L.; Garcia-Becerra, R.; Medina, L. A.; Gomez-Olivan, L.: Multimeric System of 99mTc-Labeled Gold Nanoparticles Conjugated to c[RGDfK(C)] for Molecular Imaging of Tumor α(v)β(3) Expression. *Bioconjugate Chem.* 2011, 22, 913-922.

Moss, J. A.; Vavere, A. L.; Azhdarinia, A.: Design of peptide imaging agents for whole-body and intraoperative molecular imaging. *Curr. Med. Chem.* 2012, 19, 3255-3265.

Oh, S. J.; Chi, D. Y.; Mosdzianowski, C.; Kil, H. S.; Ryu, J. S.; Moon, D. H. The automatic production of 16α-[18F]fluoroestradiol using a conventional [18F]EDG module with a disposable cassette system, *Appl Radiat Isot,* 2007, 65, 676-681.

Pantaleo M A; Nannini M; Maleddu A; Fanti S; Ambrosini V; Nanni C; Boschi S; Biasco G. Conventional and novel PET tracers for imaging in oncology in the era of molecular therapy. *Cancer Treat Rev,* 2008, 34, 103-121.

Pavlik, E. J.; Nelson, K.; Gallion, H. H.; Van, N. J. R., Jr.; Donaldson, E. S.; Shih, W. J.; Spicer, J. A.; Preston, D. F.; Baranczuk, R. J.; Kenady, D. E.: Characterization of high specific activity [16α-123I]iodo-17β-estradiol as an estrogen receptor-specific radioligand capable of imaging estrogen receptor-positive tumors, *Cancer Res.* 1990, 50, 7799-805.

Peterson, L. M.; Kurland, B. F.; Link, J. M.; Schubert, E. K.; Stekhova, S.; Linden, H. M.; Mankoff, D. A. Factors influencing the uptake of 18F-fluoroestradiol in patients with estrogen receptor positive breast cancer, *Nucl Med Biol,* 2011, 38, 969-978.

Pomper, M. G.; VanBrocklin, H.; Thieme, A. M.; Thomas, R. D.; Kiesewetter, D. O.; Carlson, K. E.; Mathias, C. J.; Welch, M. J.; Katzenellenbogen, J. A.: 11β-Methoxy-, 11β-ethyl, and 17α-ethynyl-substituted 16α-fluoroestradiols: receptor-based imaging agents with enhanced uptake efficiency and selectivity. *J. Med. Chem.* 1990, 33, 3143-55.

Pysz, M. A.; Gambhir, S. S.; Willmann, J. K.: Molecular imaging: current status and emerging strategies. *Clin Radiol* 2010, 65, 500-16.

Ribeiro-Barras, M. J.; Foulon, C.; Baulieu, J. L.; Guilloteau, D.; Bougnoux, P.; Lansac, J.; Besnard, J. C.: Estrogen receptor imaging with 17 alpha-[123I]iodovinyl-11 beta-methoxyestradiol (MIVE2)—Part II, Preliminary results in patients with breast carcinoma, *Int J Rad Appl Instrum B* 1992, 19, 263-7.

Rijks, L. J. M.; Boer, G. J.; Endert, E.; De, B. K.; Janssen, A. G. M.; Van, R. E. A.: The Z-isomer of 11β-methoxy-17α-[123I]iodovinylestradiol is a promising radioligand for estrogen receptor imaging in human breast cancer, *Nucl. Med. Biol.* 1997, 24, 65-75.

Romer, J.; Fuchtner, F.; Steinbach, J.; Johannsen, B. Automated production of 16alpha-[18F]fluoroestradiol for breast cancer imaging, *Nucl Med Biol.* 1999, 26, 473-9.

Schiff, R.; Massarweh, S. A.; Shou, J.; Bharwani, L.; Arpino, G.; Rimawi, M.; Osborne, C. K. Advanced concepts in estrogen receptor biology and breast cancer endocrine resistance: implicated role of growth factor signaling and estrogen receptor coregulators. *Cancer Chemo Pharmacol,* 2005, 56(Suppl. 1), s10-s20.

Schroeder, C. P.; Hospers, G. A. P.; Willemse, P. H. B.; Perik, P. J.; de Vries, E. F. J.; Jager, P. L.; van der Graaf, W. T. A.; Lub-de Hooge, M. N.; de Vries, E. G. E. Molecular imaging in metastatic breast cancer, *Cancer Metas—Biol Treat,* 2007, 11, 307-319.

Seimbille, Y.; Rousseau, J.; Benard, F.; Morin, C.; Ali, H.; Avvakumov, G.; Hammond, G. L.; van, L. J. E.: 18F-labeled difluoroestradiols: preparation and preclinical evaluation as estrogen receptor-binding radiopharmaceuticals. *Steroids* 2002, 67, 765-775.

Sundararajan, L; Linden H. M.; Link, J. M.; Krohn, K. A.; Mankoff, D. A. 18F-Fluoroestradiol. *Semin Nucl Med,* 2007, 37:470-476.

van de Ven S M W Y; Elias S G; van den Bosch M A A J; Luijten P; Mali W P Th M. Optical imaging of the breast, *Cancer Imaging,* 2008, 8, 206-215.

VanBrocklin, H. F.; Carlson, K. E.; Katzenellenbogen, J. A.; Welch, M. J.: 16β-([18F]Fluoro)estrogens: systematic investigation of a new series of fluorine-18-labeled estrogens as potential imaging agents for estrogen-receptor-positive breast tumors. *J. Med. Chem.* 1993, 36, 1619-29.

VanBrocklin, H. F.; Liu, A.; Welch, M. J.; O'Neil, J. P.; Katzenellenbogen, J. A.: The synthesis of 7α-methyl-substituted estrogens labeled with fluorine-18: potential breast tumor imaging agents. *Steroids* 1994, 59, 34-45.

Varghese, C. The significance of oestrogen and progesterone receptors in breast cancer. *J Clin Diagnostic Res.,* 2007, 1, 198-203.

Vavere, A. L.; Rossin, R.: Molecular imaging of cancer with radiolabeled peptides and PET. *Anti-Cancer Agents Med. Chem.* 2012, 12, 462-475.

Yager, J. D.; Davidson, N. E.: Estrogen carcinogenesis in breast cancer. *N. Engl. J. Med.* 2006, 354, 270-282.

Yu E. Y; Mankoff D. A. Positron emission tomography imaging as a cancer biomarker. *Exp Rev Molec Diag,* 2007, 7, 659-672.

What is claimed is:

1. A compound according to formula (I)

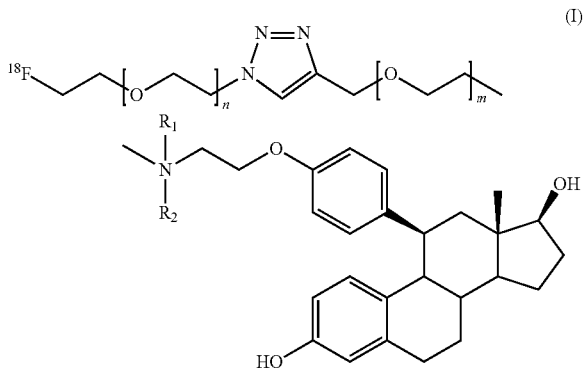

wherein n is a number in the range of 1-10; m is a number in the range of 4-10; $R^1$ is H or a $C_{1-3}$ alkyl group; and $R^2$ is either absent, or selected from the group consisting of H and a $C_{1-3}$ alkyl group.

2. A compound according to formula (II)

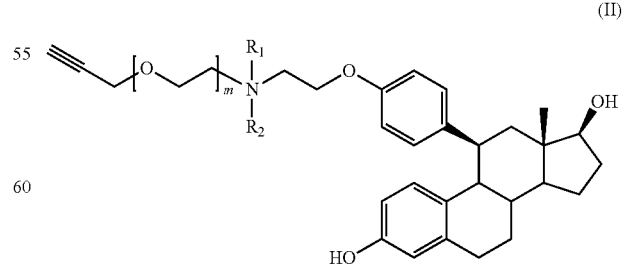

wherein m is a number in the range of 4-10; and $R^1$ is H or a $C_{1-3}$ alkyl group; and $R^2$ is either absent, or selected from the group consisting of H and a $C_{1-3}$ alkyl group.

3. A compound according to formula (III)

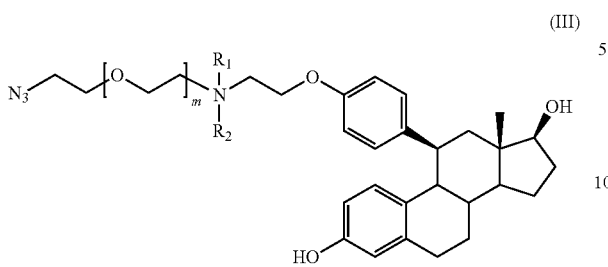

(III)

wherein m is a number in the range of 4-10; $R^1$ is H or a $C_{1-3}$ alkyl group; and $R^2$ is either absent, or selected from the group consisting of H and a C, 1-3 alkyl group.

4. A process for the preparation of a compound according to formula (I) comprising the step of reacting a compound according to formula (II) with a compound according to formula (IV) using a Huisgen [3+2] cycloaddition reaction,

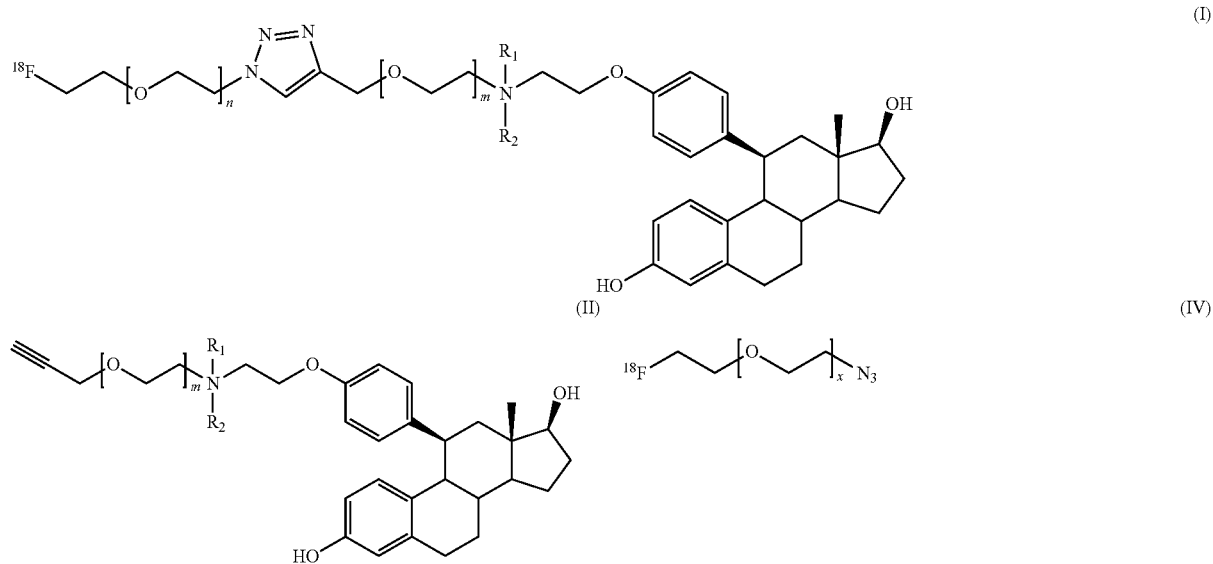

wherein n is a number in the range of 1-10; m is a number in the range of 4-10; $R^1$ is H or a $C_{1-3}$ alkyl group; and $R^2$ is either absent, or selected from the group consisting of H and a $C_{1-3}$ alkyl group, and wherein x is a number in the range of 1-10.

5. A pharmaceutical composition comprising the compound according to claim 1 and a pharmaceutically effective carrier or diluent.

6. A method of diagnosing a disease characterized by overexpression of estrogen receptors in a subject, the method comprising detecting a cell of the subject expressing estrogen receptors by contacting the compound according to claim 1 with the cell, imaging the cell with positron emission tomography (PET) or single photon emission computed tomography (SPECT), and determining from the imaging whether estrogen receptors are overexpressed in the cell compared to a normal cell, wherein the subject is diagnosed as having the disease if overexpression of estrogen receptors is detected in the cell, wherein the disease is breast cancer or endometrial cancer.

7. A method of determining effectiveness of an anticancer treatment of a subject with breast cancer or endometrial cancer, the method comprising providing an anti-cancer treatment to the subject followed by detecting cells of the subject expressing estrogen receptors by contacting the compound according to claim 1 with the cells, imaging the cells by positron emission tomography (PET) or single photon emission computed tomography (SPECT), and determining from the imaging whether estrogen receptors are overexpressed in the cells compared to normal cells, wherein the treatment is considered effective if overexpression of estrogen receptors is decreased in the cells compared to before the treatment.

8. A process for the preparation of a compound according to formula (XVIII)

comprising the steps of transforming estra-5(10),9(11)-diene-3,17-dione 3-ethylenedioxy ketal (1) into 11β-(4-Hydroxy-phenyl)-estra-4,9-diene-3,17-dione (3) by reacting (1) initially with a peroxide reagent to give an epoxide, treating the product obtained with the Grignard reagent derived from trimethylsilyloxyphenyl bromide to obtain compound (3), alkylating (3) with dimethylaminoethyl chloride to obtain compound (4), aromatizing (4) with acetyl bromide and acetic anhydride to obtain compound (5), reducing and saponifying (5) to obtain compound (6), demethylating (6) with alpha chloroethyl chloroformate to obtain compound (7), and reacting (7) with reagent (8a),

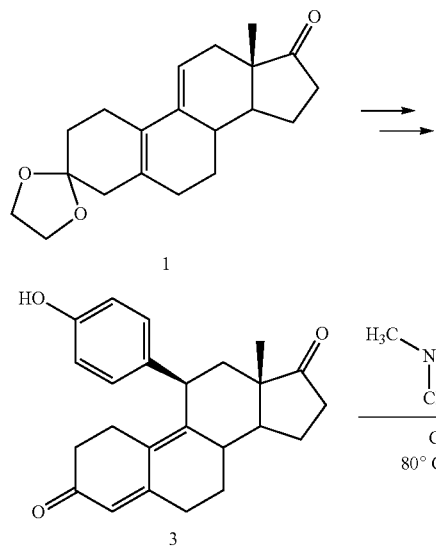

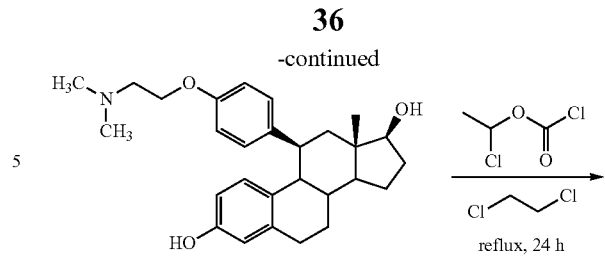

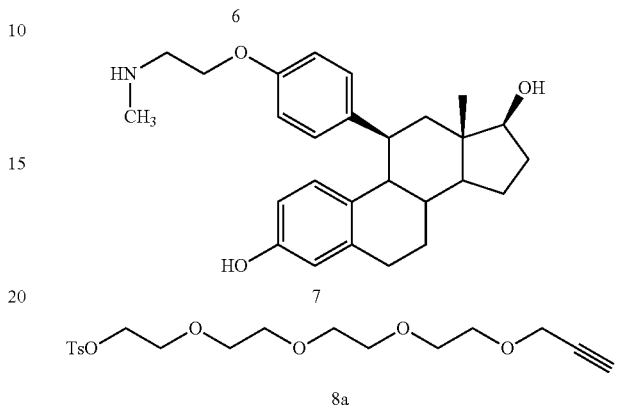

thereby obtaining the compound according to formula (XVIII).

9. A process for the preparation of a compound according to formula (XIX)

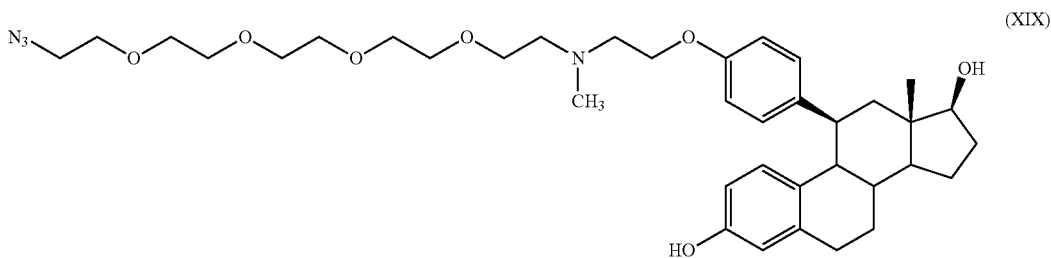 [SMILES: CN(CCOCCOCCOCCOCCN=[N+]=[N-])CCOc1ccc([C@H]2C[C@@]3(C)C(CC[C@@H]3O)C3CCc4cc(O)ccc4C32)cc1]

-continued

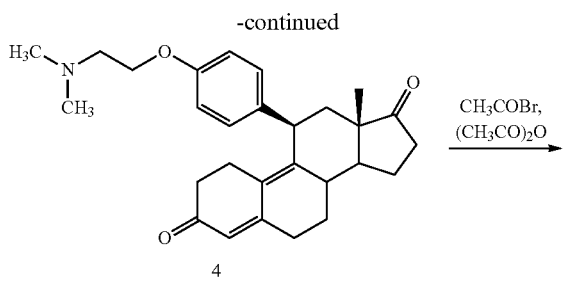

comprising the steps of transforming estra-5(10),9(11)-diene-3,17-dione 3-ethylenedioxy ketal (1) into 11β-(4-Hydroxy-phenyl)-estra-4,9-diene-3,17-dione (3), by reacting (1) initially with a peroxide reagent to give an epoxide, treating the product obtained with the Grignard reagent derived from trimethylsilyloxyphenyl bromide to obtain compound (3), alkylating (3) with dimethylaminoethyl chloride to obtain compound (4), aromatizing (4) with acetyl bromide and acetic anhydride to obtain compound (5), reducing and saponifying (5) to obtain compound (6), demethylating (6) with alpha chloroethyl chloroformate to obtain compound (7), and reacting (7) with reagent (8b)

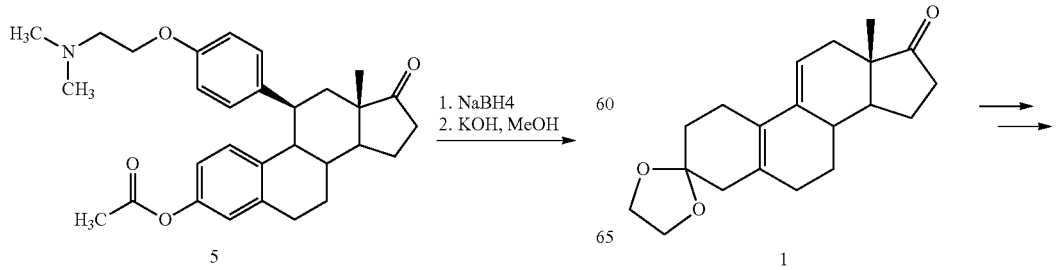

-continued

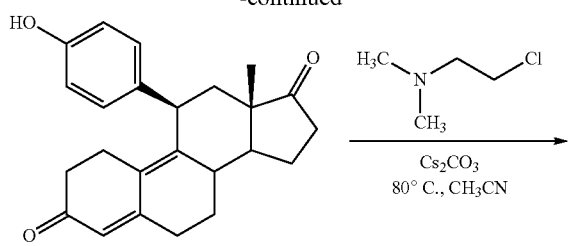

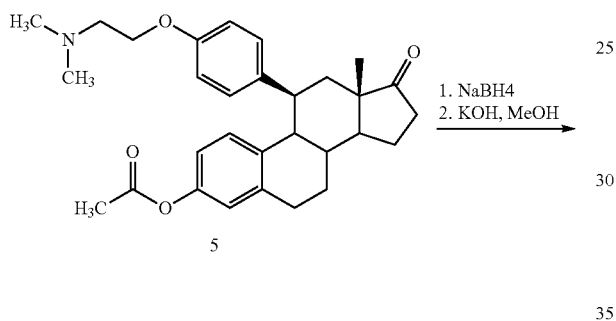

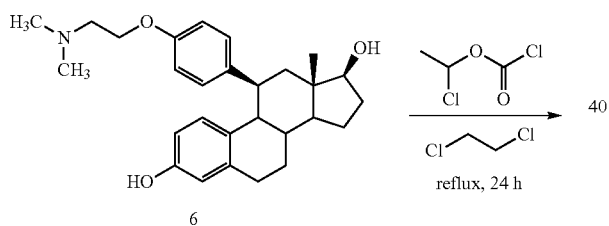

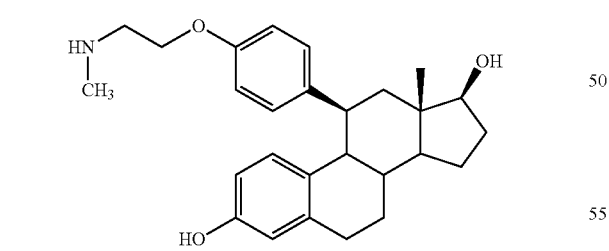

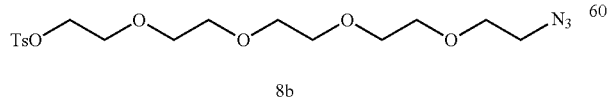

thereby obtaining the compound according to formula (XIX).

10. A process for the preparation of a compound according to formula (XX)

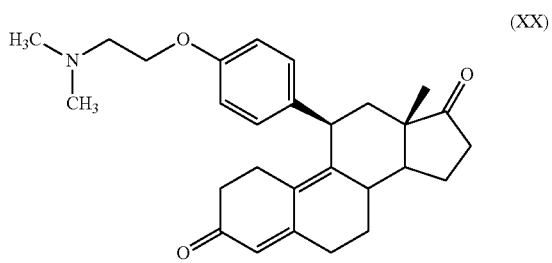 [SMILES: CN(C)CCOc1ccc([C@H]2C[C@]3(C)C(=O)CCC3C3CCC4=CC(=O)CCC4=C32)cc1]

comprising the steps of: preparing 2-(4-bromophenoxy)-N,N-dimethylethanamine (1) by reacting 4-bromophenol with 2-dimethylaminoethyl chloride, converting (1) to (4-(2-(dimethylamino)ethoxy)phenyl)magnesium bromide (2) by treating with reagents comprising Mg, and iodine, and reacting (2) with 3,3-Ethylenedioxy-5(10)-α-epoxy-estr-9-ene-17-one (3) in the presence of CuI and acetic acid

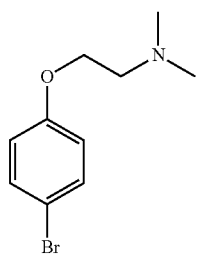

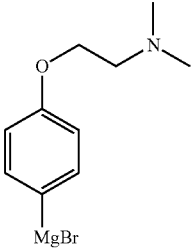

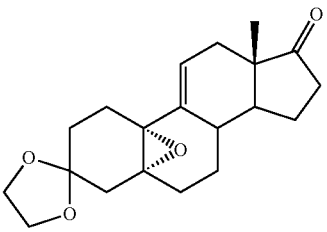

thereby obtaining the compound according to formula (XX).

11. A kit comprising a compound according to Formula (II)

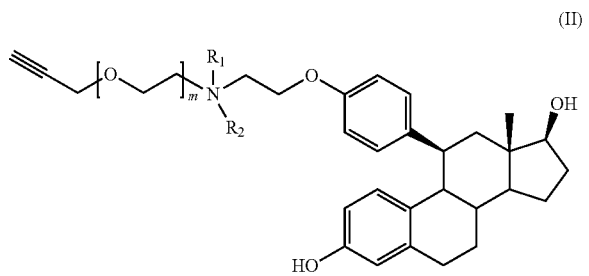
(II)

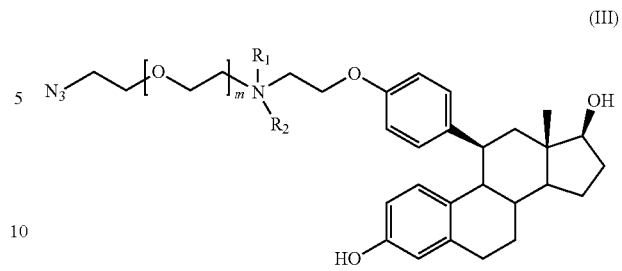
(III)

wherein m is a number in the range of 4-10; and $R^1$ is H or a $C_{1-3}$ alkyl group; and $R^2$ is either absent, or selected from the group consisting of H and a $C_{1-3}$ alkyl group, a labeling moiety, and instructions for reacting the compound and the labeling moiety to provide a compound according to claim 1, wherein the labeling moiety is a compound of formula (IV)

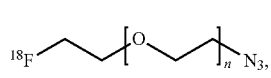
IV wherein, n is a number in the range of 1-10.

12. A kit comprising a compound according to Formula (III)

wherein m is a number in the range of 4-10; $R^1$ is H or a $C_{1-3}$ alkyl group; and $R^2$ is either absent, or selected from the group consisting of H and a $C_{1-3}$ alkyl group, a labeling moiety, and instructions for reacting the compound and the labeling moiety to provide a compound according to claim 1, wherein the labeling moiety is a compound of formula (XXI)

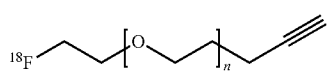
XXI wherein n is a number in the range of 1-10.

* * * * *

UNITED STATES PATENT AND TRADEMARK OFFICE
CERTIFICATE OF CORRECTION

PATENT NO. : 10,385,093 B2  
APPLICATION NO. : 14/649702  
DATED : August 20, 2019  
INVENTOR(S) : Robert N. Hanson and Kinh-Luan Dao Page 1 of 1

It is certified that error appears in the above-identified patent and that said Letters Patent is hereby corrected as shown below:

In the Specification

Column 1, Line 14, insert the following:
--STATEMENT REGARDING FEDERALLY SPONSORED RESEARCH OR DEVELOPMENT
This invention was made with government support under Grant Number DE-SC0001781 awarded by the Department of Energy. The government has certain rights in the invention.--

Signed and Sealed this
Twenty-third Day of November, 2021

Drew Hirshfeld
*Performing the Functions and Duties of the*
*Under Secretary of Commerce for Intellectual Property and*
*Director of the United States Patent and Trademark Office*